United States Patent [19]

Jacobson

[11] Patent Number: 5,798,311
[45] Date of Patent: Aug. 25, 1998

[54] N-ARYL-3-ARYL-4-SUBSTITUTED-4,5-DIHYDRO-1H-PYRAZOLE-1-CARBOXAMIDES AND METHODS OF THEIR PRODUCTION

[75] Inventor: Richard Martin Jacobson, Chalfont, Pa.

[73] Assignee: Rohm and Haas Company, Phila., Pa.

[21] Appl. No.: 468,284

[22] Filed: Jun. 6, 1995

Related U.S. Application Data

[63] Continuation-in-part of Ser. No. 415,117, Mar. 29, 1995, abandoned, which is a continuation of Ser. No. 49,891, Apr. 19, 1993, abandoned, which is a division of Ser. No. 713,692, Jun. 17, 1991, abandoned, which is a continuation-in-part of Ser. No. 553,220, Jul. 13, 1990, abandoned.

[51] Int. Cl.$^6$ ............................ A01N 43/56; C07D 231/40; C07D 403/04
[52] U.S. Cl. ........................ 504/282; 514/403; 548/371.7
[58] Field of Search ..................... 548/371.7; 514/403; 504/282

[56] References Cited

U.S. PATENT DOCUMENTS

| | | | |
|---|---|---|---|
| 4,070,365 | 1/1978 | Van Daalen et al. | 548/379 |
| 4,156,007 | 5/1979 | Van Daalen et al. | 424/273 |
| 4,174,393 | 11/1979 | Van Daalen et al. | 424/250 |
| 4,407,813 | 10/1983 | Ozawa et al. | 424/273 |
| 4,439,440 | 3/1984 | Van Hee et al. | 424/273 |
| 4,464,386 | 8/1984 | Ozawa et al. | 424/273 |
| 4,663,341 | 5/1987 | Jacobson | 514/403 |
| 4,863,947 | 9/1989 | Jacobson | 514/403 |

FOREIGN PATENT DOCUMENTS

| | | |
|---|---|---|
| 113213 | 7/1984 | European Pat. Off. . |
| 3545786 | 6/1987 | Germany . |

*Primary Examiner*—Johann Richter
*Assistant Examiner*—Laura L. Stockton
*Attorney, Agent, or Firm*—Clark R. Carpenter

[57] ABSTRACT

This invention relates to novel N-aryl-3-aryl-4-substituted-4,5-dihydro-1H-pyrazole-1-carboxamide compounds which are useful as pesticides, compositions containing those compounds, methods of controlling pests and processes for preparing these compounds.

22 Claims, No Drawings

N-ARYL-3-ARYL-4-SUBSTITUTED-4,5-DIHYDRO-1H-PYRAZOLE-1-CARBOXAMIDES AND METHODS OF THEIR PRODUCTION

This application is a continuation-in-part of application Ser. No. 08/415,117, filed Mar. 29, 1995 now abandoned, which is a continuation of Ser. No. 08/049,891, filed Apr. 19, 1993, now abandoned, which is a divisional application of Ser. No. 07/713,692, filed Jun. 17, 1991, now abandoned, which is a continuation-in-part of Ser. No. 07/553,220, filed Jul. 13, 1990, now abandoned.

This invention relates to novel N-aryl-3-aryl-4-substituted-4,5-dihydro-1H-pyrazole-1-carboxamides which are useful as pesticides, compositions containing those compounds, methods of controlling pests and processes for preparing the compounds of the present invention.

The search for pesticides which have a combination of excellent pesticidal activity and essentially no other toxicity is a continuing one due to recognition of the possible toxicity to animals and humans of many known pesticides.

Presently known dihydropyrazole insecticides, such as those disclosed in U.S. Pat. Nos. 4,863,947, 4,070,365, 4,174,393, 4,439,440, 4,407,813, and 4,156,007, are believed to be subject to problems with photostability and/or biodegradability. These compounds tend to degrade faster than is desirable when applied to the external parts of plants due to the action of sunlight on these compounds. Moreover, when known compounds are applied to the soil, they exhibit poor biodegradability causing an undesirable residue to remain in the soil.

This invention relates to N-aryl-3-aryl-4-substituted-4,5-dihydro-1H-pyrazole-1-carboxamides substituted at the 4 position by a substituent which is attached to the pyrazoline ring by a heteroatom.

It is believed this substitution may sufficiently alter metabolic pathway transformations in plants and insects to provide the necessary differentiation which allows for high insect toxicity and low mammalian toxicity. It is further believed to permit appropriate biodegradation.

It is therefore an object of the invention to provide novel compounds, and compositions containing the compounds, which possess pesticidal activity. It is another object of the present invention to provide compounds which demonstrate improved differentiation between insecticidal activity and mammalian toxicity. It is a further object of the invention to provide methods for the synthesis of 1-substituted-4-substituted-4,5-dihydro-1H-pyrazoles. It is still another object of the present invention to provide methods for controlling pests and insects using the novel compounds.

These and other objects of the invention will become apparent to those skilled in the art from the following description.

In accordance with the present invention, there are provided compounds having the formula:

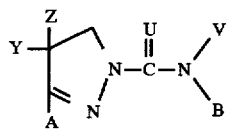

wherein

A is aryl or aromatic heterocycyl;

B is aryl or aromatic heterocycyl;

U is oxygen (O) or sulfur (S);

V is hydrogen, alkyl, alkoxyalkyl, alkylthioalkyl, formyl, alkylcarbonyl, alkylaminocarbonyl, carboxy, alkoxycarbonyl, alkenyloxycarbonyl, alkynyloxycarbonyl, phenyloxycarbonyl, alkoxycarbonylcarbonyl, alkoxy, phenyloxy, alkoxycarbonylalkoxy, alkoxycarbonyloxy, alkylthio, alkylsulfonyl, phenylthio, alkoxycarbonylalkylthio or alkoxycarbonylthio;

Y is isothiocyanato (—NCS), isocyano (—NC), amino (—NR$^1$R$^2$), alkanoyloxy, alkoxy, phenyloxy, alkylthio, alkylsulfonyl or phenylthio;

wherein R$^1$ and R$^2$ are independently hydrogen, cyano, alkyl, alkenyl, alkynyl, phenylalkyl, formyl, alkylcarbonyl, alkenylcarbonyl, alkynylcarbonyl, alkoxyalkylcarbonyl, phenylcarbonyl, phenylalkylcarbonyl, phenylalkenylcarbonyl, phenylalkynylcarbonyl, alkoxycarbonyl, alkoxyalkoxycarbonyl, alkenyloxycarbonyl, alkynyloxycarbonyl, alkanoylalkoxycarbonyl, alkoxycarbonylcarbonyl, alkoxycarbonylalkoxycarbonyl, carboxyalkoxycarbonyl, phenyloxycarbonyl, phenylalkoxycarbonyl, alkylthiocarbonyl, alkenylthiocarbonyl, alkynylthiocarbonyl, alkanoylalkylthiocarbonyl, alkoxycarbonylalkylthiocarbonyl, alkylthiocarbonylalkoxycarbonyl, alkylthiocarbonylalkylthiocarbonyl, carbonylalkylthiocarbonyl, phenylthiocarbonyl, phenylalkylthiocarbonyl, N-alkylaminocarbonyl, N,N-dialkylaminocarbonyl, N-phenyl-N-alkylaminocarbonyl, N-(phenylcarbonyl)aminocarbonyl, dialkylphosphoryl (—P(O)(OR)$_2$), dialkylthiophosphoryl (—P(S)(OR)$_2$), alkylsulfonyl, alkenylsulfonyl, alkynylsulfonyl, phenylsulfonyl, N-alkylaminosulfonyl, N,N-dialkylaminosulfonyl, phenylsulfonyl, or heterocyclyl; or R$^1$ and R$^2$ together with the nitrogen to which they are attached form a 5- or 6-membered ring; and Z is hydrogen or alkyl; or agronomically acceptable salts thereof.

Alkyl means straight and branched alkyl groups, for example (C$_1$–C$_6$)alkyl such as methyl, ethyl, n-propyl, isopropyl, n-butyl, isobutyl, s-butyl, t-butyl or n-pentyl. An alkyl portion of any one of the substituents listed above for V, Y and Z or of the substituents on the aryl rings listed below is optionally substituted by one to eight halogens to form groups such as trifluoromethyl, bromodifluoromethyl, 1,1,2,2,2-pentafluoroethyl, 1,1,2,2-tetrafluoroethyl, chloromethyl, dichloromethyl, trichloromethyl, difluoromethyl, 2-bromoethyl, 2-chloroethyl, 3-bromopropyl, 2-chloro-1,1,2-trifluoroethyl, 2-bromo-1,1,2,2-tetrafluoroethyl, or 1,1,2,3,3,3-hexafluoropropyl; or optionally substituted by cyano to form groups such as 3-cyanopropyl.

Alkenyl is, for example, (C$_2$–C$_6$)alkenyl such as vinyl and allyl.

Alkynyl is, for example, (C$_3$–C$_6$)alkynyl such as propargyl.

Alkoxyalkyl is, for example (C$_1$–C$_6$)alkoxy(C$_1$–C$_6$)alkyl such as methoxymethyl and methoxyethyl.

Alkylthioalkyl is, for example, (C$_1$–C$_6$)alkylthio(C$_1$–C$_6$)alkyl.

Phenylalkyl is, for example, phenyl(C$_1$–C$_6$)alkyl such as benzyl and 2-phenylethyl.

Alkylcarbonyl is, for example, (C$_1$–C$_6$)alkylcarbonyl such as methylcarbonyl (acetyl), ethylcarbonyl, n-propylcarbonyl, isopropylcarbonyl, n-butylcarbonyl, isobutylcarbonyl, t-butylcarbonyl, n-pentylcarbonyl, chloromethylcarbonyl, trichloromethylcarbonyl, trifluoromethylcarbonyl, 3-chloropropylcarbonyl, 4-chlorobutylcarbonyl, pentafluoroethylcarbonyl and heptafluoropropylcarbonyl.

Alkenylcarbonyl is, for example, ($C_2$–$C_6$)alkenylcarbonyl such as vinylcarbonyl, 1-methylvinylcarbonyl, 2-methylvinylcarbonyl, 2,2-dimethylvinylcarbonyl and 1,2,2-trichlorovinylcarbonyl.

Alkynylcarbonyl is, for example, ($C_2$–$C_6$) alkynylcarbonyl.

Alkoxyalkylcarbonyl is, for example, ($C_1$–$C_6$)alkoxy($C_1$–$C_6$)alkylcarbonyl such as methoxymethylcarbonyl.

Phenylalkylcarbonyl is, for example, phenyl($C_1$–$C_6$) alkylcarbonyl.

Phenylalkenylcarbonyl is, for example, phenyl($C_2$–$C_6$) alkenylcarbonyl such as phenylvinylcarbonyl (cinnamoyl).

Phenylalkynylcarbonyl is, for example, phenyl($C_2$–$C_6$) alkynyl.

Alkylaminocarbonyl is, for example, mono($C_1$–$C_6$) alkylaminocarbonyl, such as methylaminocarbonyl, or di($C_1$–$C_6$)alkylaminocarbonyl such as dimethylaminocarbonyl.

Alkoxycarbonyl is for example, ($C_1$–$C_6$)alkoxycarbonyl such as methoxycarbonyl (carbomethoxy), ethoxycarbonyl (carboethoxy), n-propyloxycarbonyl, isopropyloxycarbonyl, n-butyloxycarbonyl, isobutyloxycarbonyl, t-butyloxycarbonyl, n-pentyloxycarbonyl, cyanomethoxycarbonyl, 2-cyanoethoxycarbonyl, 2-bromoethoxycarbonyl, 2-chloroethoxycarbonyl, 2,2,2-trifluoroethoxycarbonyl, 2,2,2-trichloroethoxycarbonyl, 3-bromopropyloxycarbonyl, 3-chloropropyloxycarbonyl and 4-chlorobutyloxycarbonyl.

Alkoxycarbonylcarbonyl is, for example, ($C_1$–$C_6$) alkoxycarbonylcarbonyl such as methoxycarbonylcarbonyl.

Alkenyloxycarbonyl is, for example, ($C_2$–$C_6$) alkenyloxycarbonyl such as vinyloxycarbonyl and allyloxycarbonyl.

Alkynyloxycarbonyl is, for example, ($C_3$–$C_6$) alkynyloxycarbonyl such as propargyloxycarbonyl.

Alkoxyalkoxycarbonyl is, for example, ($C_1$–$C_6$)alkoxy ($C_1$–$C_6$)alkoxycarbonyl such as methoxyethoxycarbonyl.

Alkanoylalkoxycarbonyl is, for example, ($C_1$–$C_6$) alkanoyl($C_1$–$C_6$)alkoxycarbonyl such as methylcarbonylmethoxycarbonyl.

Alkoxycarbonylalkoxycarbonyl is, for example, ($C_1$–$C_6$) alkoxycarbonyl($C_1$–$C_6$)alkoxycarbonyl such as ethoxycarbonylmethoxycarbonyl and ethoxycarbonylethoxycarbonyl.

Carboxyalkoxycarbonyl is, for example, carboxy($C_1$–$C_6$) alkoxycarbonyl such as carboxyethoxycarbonyl and carboxypropoxycarbonyl.

Phenylalkoxycarbonyl is, for example, phenyl($C_1$–$C_6$) alkoxycarbonyl such as benzyloxycarbonyl and 2-phenylethoxycarbonyl.

(Alkylthio)carbonyl is, for example, (($C_1$–$C_6$)alkylthio) carbonyl such as (methylthio)carbonyl, (ethylthio)carbonyl, (n-propylthio)carbonyl, and (n-butylthio)carbonyl.

(Alkenylthio)carbonyl is, for example, (($C_3$–$C_6$)alkylthio) carbonyl.

(Alkynylthio)carbonyl is, for example, (($C_3$–$C_6$) alkynylthio)carbonyl.

Alkylcarbonyl(alkylthio)carbonyl is, for example, ($C_1$–$C_6$)alkylcarbonyl($C_1$–$C_6$)alkylthio)carbonyl.

Alkoxycarbonyl(alkylthio)carbonyl is, for example, ($C_1$–$C_6$)alkoxycarbonyl($C_1$–$C_6$)alkylthio)carbonyl.

(Alkylthio)carbonylalkoxycarbonyl is, for example, (($C_1$–$C_6$)alkylthio)carbonyl($C_1$–$C_6$)alkoxycarbonyl.

(Alkylthio)carbonyl(alkylthio)carbonyl is, for example, (($C_1$–$C_6$)alkylthio)carbonyl(($C_1$–$C_6$)alkylthio)carbonyl.

Carboxy(alkylthio)carbonyl is, for example, carboxy( ($C_1$–$C_6$)-alkylthio)carbonyl.

(Phenylalkylthio)carbonyl is, for example, (phenyl ($C_1$–$C_6$)alkylthio)carbonyl.

N-alkylaminocarbonyl is, for example, N-($C_1$–$C_6$) alkylaminocarbonyl such as methylaminocarbonyl.

N,N-dialkylaminocarbonyl is, for example, N,N-di ($C_1$–$C_6$)alkylaminocarbonyl such as dimethylaminocarbonyl.

N-phenyl-N-alkylaminocarbonyl is, for example, N-phenyl-N-($C_1$–$C_6$)alkylaminocarbonyl such as N-methyl-N-(phenyl)aminocarbonyl.

N-(phenylcarbonyl)aminocarbonyl is, for example, N-(2, 6-difluorophenylcarbonyl)aminocarbonyl.

Dialkylphosphoryl is, for example, di($C_1$–$C_6$) alkylphosphoryl such as diethylphosphoryl.

Dialkylthiophosphoryl is, for example, di($C_1$–$C_6$) alkylthiophosphoryl such as diethylthiophosphoryl.

Alkylsulfonyl is, for example, ($C_1$–$C_6$)alkylsulfonyl such as methylsulfonyl, n-butylsulfonyl, chloromethylsulfonyl, trifluoromethylsulfonyl and 2,2,2-trifluoroethylsulfonyl.

Alkenylsulfonyl is, for example, ($C_2$–$C_6$)alkenylsulfonyl such as vinylsulfonyl.

Alkynylsulfonyl is, for example, ($C_3$–$C_6$)alkynylsulfonyl.

N,N-dialkylaminosulfonyl is, for example, N,N-di ($C_1$–$C_6$)alkylaminosulfonyl such as dimethylaminosulfonyl.

Alkoxy is, for example, ($C_1$–$C_6$)alkoxy such as methoxy, ethoxy, n-propyloxy, n-butyloxy, isobutyloxy, n-pentyloxy, trifluoromethoxy, difluoromethoxy, 1,1,2,2-tetrafluoroethoxy and 1,1,2,3,3,3-hexafluoropropyloxy.

Alkylthio is, for example, ($C_1$–$C_6$)alkylthio such as methylthio, n-propylthio, n-butylthio and 3-cyanopropylthio.

Alkoxycarbonylthio is, for example ($C_1$–$C_6$) alkoxycarbonylthio such as methoxycarbonylthio.

Phenylthio includes, for example, phenylthio and 2-nitrophenylthio.

Alkoxycarbonylalkylthio is, for example, ($C_1$–$C_6$) alkoxycarbonyl($C_1$–$C_6$)alkylthio such as 1-(methoxycarbonyl)prop-2-ylthio.

Heterocyclyl means five or six membered heterocyclic ring containing one, two or three heteroatoms such as oxygen, nitrogen or sulfur and includes saturated and aromatic rings, for example tetrahydrofuryl, furyl, pyridyl, pyrazinyl, oxazolyl, piperidyl, triazolyl, thienyl, thiazolyl or piperazyl. The heterocycyl ring is optionally substituted by one or two independently choses substituents, for example, nitro, ($C_1$–$C_6$)alkyl such as methyl and trifluoromethyl and halo such as chloro.

Aryl is an aromatic carbocyclic structure, for example, phenyl or naphthyl.

Naphthyl is optionally substituted by one or two independently chosen substituents, for example, nitro, ($C_1$–$C_6$)alkyl such as methyl and trifluoromethyl and halo such as chloro.

Phenyl is optionally substituted by one to three independently chosen substituents, for example, ($C_1$–$C_6$)alkyl, halo, hydroxy, ($C_1$–$C_6$)alkoxy, ($C_3$–$C_6$)alkenyloxy, ($C_3$–$C_6$) alkynyloxy, ($C_1$–$C_6$)alkoxy($C_1$–$C_6$)alkoxy, phenyl($C_1$–$C_6$) alkoxy, phenyloxy, pyridyloxy, mono($C_1$–$C_6$) alkylaminocarbonyloxy, di($C_1$–$C_6$)alkylaminocarbonyloxy, ($C_1$–$C_6$)alkanoyloxy, ($C_1$–$C_6$)alkoxycarbonyloxy, ($C_1$–$C_6$) alkylsulfonyloxy, ($C_1$–$C_6$)alkylthio, ($C_1$–$C_6$)alkoxy($C_1$–$C_6$) alkyl, ($C_1$–$C_6$)alkanoyl, ($C_1$–$C_6$)alkoxycarbonyl, nitro, ($C_1$–$C_6$)alkylsulfonyl, phenyl, cyano, isocyano (—NC), amino, mono($C_1$–$C_6$)alkylamino, di($C_1$–$C_6$)alkylamino, formylamino (—NHCHO), ($C_1$–$C_6$)alkanoylamino, phenylcarbonylamino, mono($C_1$–$C_6$)- alkylaminocarbonylamino, and di($C_1$-$C_6$) alkylaminocarbonylamino, such as 4-methyl, 4-ethyl, 4-propyl, 4-t-butyl, 4-trifluoromethyl, 4-dichloromethyl, 4-trichloromethyl, 4-fluoro, 4-bromo, 4-chloro, 4-iodo, 4-hydroxy, 4-methoxy, 4-ethoxy, 4-n-propyloxy, 4-isopropyloxy, 4-sec-butyloxy, 4-n-butyloxy, 4-isobutyloxy, 4-n-pentyloxy, 4-difluoromethoxy, 4-trifluoromethoxy, 4-(1,1,2,2-tetrafluoroethoxy), 4-bromodifluoromethoxy, 4-(1,1,2,3,3,3-hexafluoropropyloxy), 4-allyloxy, 4-propargyloxy, 4-methoxymethoxy, 4-benzyloxy, 4-(2-phenylethoxy), 4-phenyloxy, 4-(2-chloro-4-trifluoromethylphenyloxy), 4-(5-chloro-2-pyridyloxy), 4-(5-(trifluoromethyl)-2-pyridyloxy), 4-(3-chloro-5-(trifluoromethyl)-2-pyridyloxy), 4-methylaminocarbonyloxy, 4-(N,N-dimethylaminocarbonyloxy), 4-acetoxy, 4-methoxycarbonyloxy, 4-methylsulfonyloxy, 4-trifluoromethylsulfonyloxy, 4-methylthio, 4-(1,1,2,2,tetrafluoroethylthio), 4-(2-ethoxyethyl), 4-acetyl (methylcarbonyl), 4-ethylcarbonyl, 4-isopropylcarbonyl, 4-methoxycarbonyl, 4-ethoxycarbonyl, 4-isopropyloxycarbonyl, 4-nitro, 4-methylsulfonyl, 4-(1,1,2,2-tetrafluoroethylsulfonyl), 4-phenyl, 4-cyano, 4-isocyano, 4-amino, 4-methylamino, 4-dimethylamino, 4-formylamino, 4-acetamido, 4-trifluoroacetamido, 4-phenylcarbonylamino, 4-(4-chlorophenylcarbonylamino), 4-methylaminocarbonylamino, and 4-(di-n-propylaminocarbonylamino).

Halo means fluoro, chloro, bromo and iodo.

Agronomically acceptable salts include those known in the art, for example, metal salts such as sodium, potassium, calcium and magnesium; ammonium salts such as isopropylammonium; and trialkylsulfonium salts such as trimethylsulfonium.

Also encompassed by the invention are compounds of the structure

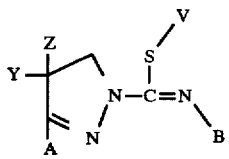

wherein A, B, V, Y and Z are as defined above. More preferably, A is 4-chlorophenyl or 4-n-propyloxyphenyl; B is 4-trifluoromethylphenyl; Y is N-methyl-N-methoxycarbonylamino; Z is hydrogen; and V is methyl, ethyl, n-propyl, isopropyl or benzyl.

Further, in accordance with the present invention, there are provided compositions containing compounds of the present invention and processes for preparing 1-substituted-4-substituted-4,5-dihydro-1H-pyrazoles of the present invention.

Further, in accordance with the invention are intermediates useful in making the compounds of the invention having the structure

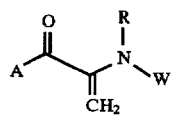

wherein A is as defined above, R is hydrogen or ($C_1$-$C_6$) alkyl and W is ($C_1$-$C_6$)alkylcarbonyl, halo($C_1$-$C_6$) alkylcarbonyl, ($C_1$-$C_6$)alkoxycarbonyl or ($C_1$-$C_6$) alkylsulfonyl.

These compounds also have fungicidal and biocidal activity.

In a preferred embodiment of the invention are compounds of Formula I

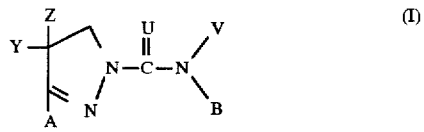

wherein

A and B are pyridyl, furyl, thiazolyl or naphthyl, each of which is optionally substituted by one or two independently chosen substituents selected from nitro, ($C_1$-$C_6$) alkyl, halo($C_1$-$C_6$)alkyl and halo;

phenyl or phenyl substituted by one to three substituents independently selected from ($C_1$-$C_6$)alkyl; halo ($C_1$-$C_6$)alkyl; halo; ($C_1$-$C_6$)alkoxy; halo($C_1$-$C_6$) alkoxy; ($C_3$-$C_6$)alkenyloxy; ($C_3$-$C_6$)alkynyloxy; ($C_1$-$C_6$)alkoxy($C_1$-$C_6$)alkoxy; phenyl($C_1$-$C_6$)alkoxy; phenyloxy; pyridyloxy; mono($C_1$-$C_6$) alkylaminocarbonyloxy; di($C_1$-$C_6$) alkylaminocarbonyloxy; ($C_1$-$C_6$)alkanoyloxy; ($C_1$-$C_6$) alkoxycarbonyloxy; ($C_1$-$C_6$)alkylsulfonyloxy; ($C_1$-$C_6$)alkylthio; halo($C_1$-$C_6$)alkylthio; ($C_1$-$C_6$) alkoxy($C_1$-$C_6$)alkyl; ($C_1$-$C_6$)alkanoyl; ($C_1$-$C_6$) alkoxycarbonyl; nitro; ($C_1$-$C_6$)alkylsulfonyl; halo ($C_1$-$C_6$)alkylsulfonyl; phenyl; hydroxy; cyano; isocyano; amino; mono($C_1$-$C_6$)alkylamino; di($C_1$-$C_6$) alkylamino; formylamino; ($C_1$-$C_6$)alkanoylamino; halo($C_1$-$C_6$)alkanoylamino; phenylcarbonylamino; mono($C_1$-$C_6$)alkylaminocarbonylamino; and di($C_1$-$C_6$)alkylaminocarbonylamino;

U is oxygen or sulfur;

V is hydrogen, ($C_1$-$C_6$)alkyl, ($C_1$-$C_6$)alkoxy($C_1$-$C_6$) alkyl, formyl, ($C_1$-$C_6$)alkylcarbonyl, ($C_1$-$C_6$) alkylaminocarbonyl, ($C_1$-$C_6$)alkoxycarbonyl, ($C_3$-$C_6$) alkenyloxycarbonyl, phenyloxycarbonyl, ($C_1$-$C_6$) alkoxycarbonylcarbonyl, cyano($C_1$-$C_6$)alkylthio, ($C_1$-$C_6$)alkylthio, phenylthio, ($C_1$-$C_6$)alkoxycarbonyl ($C_1$-$C_6$)alkylthio or ($C_1$-$C_6$)alkoxycarbonylthio;

Y is isothiocyanato, isocyano, —$NR^1R^2$, ($C_1$-$C_6$) alkanoyloxy, ($C_1$-$C_6$)alkoxy, phenyloxy, ($C_1$-$C_6$) alkylthio, ($C_1$-$C_6$)alkylsulfonyl or phenylthio;

wherein $R^1$ and $R^2$ are independently hydrogen, cyano, ($C_1$-$C_6$)alkyl, halo($C_1$-$C_6$)alkyl, cyano($C_1$-$C_6$)alkyl, phenyl($C_1$-$C_6$)alkyl, ($C_3$-$C_6$)alkenyl, halo($C_3$-$C_6$) alkenyl, ($C_3$-$C_6$)alkynyl, phenyl, halophenyl, formyl, ($C_1$-$C_6$)alkylcarbonyl, halo($C_1$-$C_6$)alkylcarbonyl, ($C_2$-$C_6$)alkenylcarbonyl, halo($C_2$-$C_6$)alkenylcarbonyl, ($C_1$-$C_6$)alkoxy($C_1$-$C_6$)alkylcarbonyl, phenylcarbonyl, phenyl($C_2$-$C_6$)alkenylcarbonyl, carboxy, ($C_1$-$C_6$) alkoxycarbonyl, halo($C_1$-$C_6$)alkoxycarbonyl, cyano ($C_1$-$C_6$)alkoxycarbonyl, ($C_2$-$C_6$)alkenyloxycarbonyl, ($C_3$-$C_6$)alkynyloxycarbonyl, ($C_1$-$C_6$)alkanoyl($C_1$-$C_6$) alkoxycarbonyl, ($C_1$-$C_6$)alkoxycarbonyl($C_1$-$C_6$) alkoxycarbonyl, carboxy($C_1$-$C_6$)alkoxycarbonyl, phenyloxycarbonyl, phenyl($C_1$-$C_6$)alkoxycarbonyl, (($C_1$-$C_6$)alkylthio)carbonyl, N-($C_1$-$C_6$) alkylaminocarbonyl, N,N-di($C_1$-$C_6$) alkylaminocarbonyl, N-phenyl-N-($C_1$-$C_6$) alkylaminocarbonyl, N-(phenylcarbonyl) aminocarbonyl, di($C_1$-$C_6$)alkylphosphoryl, ($C_1$-$C_6$) alkylsulfonyl, ($C_2$-$C_6$)alkenylsulfonyl, N,N-di($C_1$-$C_6$) alkylaminosulfonyl, phenylsulfonyl, pyridyl or pyrazinyl; or R¹ and R² together with the nitrogen to which they are attached form a 5- or 6-membered ring selected from 2-oxazolidonyl, pyrrolidinonyl, piperidonyl and succinimidyl; and Z is hydrogen or alkyl; and agronomically acceptable salts thereof.

In one class of the preferred embodiment of the invention are compounds of Formula I wherein Y is —NR¹R², isocyano or isothiocyano; V is hydrogen and the remaining substituents are as defined above.

In an embodiment of this class are compounds of the structure

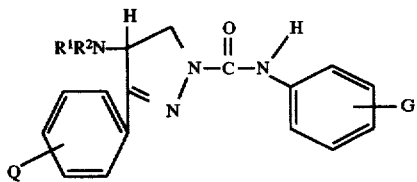

wherein

Q is hydrogen, halo, hydroxy, halo($C_1$–$C_6$)alkyloxy or ($C_1$–$C_6$)alkoxy;

G is halo, halo($C_1$–$C_6$)alkyl, ($C_1$–$C_6$)alkoxycarbonyl or halo($C_1$–$C_6$)alkoxy;

R¹ is ($C_1$–$C_6$)alkyl, ($C_3$–$C_6$)alkenyl, ($C_3$–$C_6$)alkynyl, phenyl($C_1$–$C_6$)alkyl, phenyl or halophenyl;

R² is cyano, ($C_1$–$C_6$)alkyl, ($C_1$–$C_6$)alkylsulfonyl, ($C_1$–$C_6$)alkoxycarbonyl, (($C_1$–$C_6$)alkylthio)carbonyl, halo ($C_1$–$C_6$)alkoxycarbonyl, formyl, ($C_1$–$C_6$)alkylcarbonyl, halo($C_1$–$C_6$)alkylcarbonyl, ($C_1$–$C_6$)alkoxy($C_1$–$C_6$)alkylcarbonyl, ($C_2$–$C_6$)alkenylcarbonyl, halo($C_2$–$C_6$)alkenylcarbonyl, di($C_1$–$C_6$)alkylaminocarbonyl, phenylcarbonyl, di($C_1$–$C_6$)alkylphosphoryl or di($C_1$–$C_6$)alkylthiophosphoryl; or R¹ and R² together with the nitrogen to which they are attached form 2-oxazolidonyl, isomorpholin-2-onyl, pyrrolidinonyl, piperidonyl or succinimidyl.

More preferred are compounds of the embodiment wherein Q is hydrogen, 4-halo, 4-($C_1$–$C_6$)alkoxy or 4-halo ($C_1$–$C_6$)alkoxy;

G is 4-halo, 4-halo($C_1$–$C_6$)alkyl or 4-halo($C_1$–$C_6$)alkoxy;

R¹ is ($C_1$–$C_6$)alkyl, ($C_3$–$C_6$)alkenyl, ($C_3$–$C_6$)alkynyl, phenyl or 4-halophenyl; and R² is ($C_1$–$C_6$)alkoxycarbonyl, halo($C_1$–$C_6$) alkoxycarbonyl, formyl, ($C_1$–$C_6$)alkylcarbonyl, di($C_1$–$C_6$)alkylaminocarbonyl or phenylcarbonyl.

Even more preferred are compounds of the embodiment wherein

Q is hydrogen, 4-chloro, 2,4-dichloro, 3,4-dichloro, 4-n-butyloxy, 4-n-propyloxy or 4-difluoromethoxy;

G is 4-trifluoromethyl, 4-difluoromethoxy, 4-trifluoromethoxy, 4-(1,1,2,2-tetrafluoroethoxy), 4-(1,1,2,3,3,3-hexafluoropropyloxy) or 4-isopropyloxycarbonyl;

R¹ is methyl, ethyl, n-propyl, n-butyl, allyl or propargyl; and

R² is formyl, methylcarbonyl, ethylcarbonyl, dimethylaminocarbonyl, methoxycarbonyl, ethoxycarbonyl or isopropyloxycarbonyl. Most preferred are compounds wherein Q is 4-chloro, G is 4-trifluoromethyl, R¹ is methyl and R² is formyl, methylcarbonyl, ethylcarbonyl, dimethylaminocarbonyl, methoxycarbonyl, ethoxycarbonyl or isopropyloxycarbonyl;

Q is 4-chloro, G is 4-trifluoromethyl, R² is methoxycarbonyl and R¹ is ethyl, propyl or propargyl;

Q is 4-chloro, G is 4-trifluoromethoxy, R² is methoxycarbonyl and R¹ is methyl, ethyl, propyl, allyl or propargyl;

Q is 4-chloro, G is 4-difluoromethoxy, R¹ is methyl and R² is methoxycarbonyl;

Q is 4-chloro, G is 4-(1,1,2,2-tetrafluoroethoxy), R² is methoxycarbonyl and R¹ is methyl, ethyl or propargyl;

Q is 4-chloro, G is 4-(1,1,2,3,3,3-hexafluoropropyloxy), R¹ is methyl and R² is methoxycarbonyl;

Q is 4-ethoxy, G is 4-trifluoromethoxy, R¹ is methyl and R² is methoxycarbonyl;

Q is 4-n-propyloxy, G is 4-trifluoromethoxy, R¹ is methyl and R² is methoxycarbonyl;

Q is 4-n-butyloxy, G is 4-trifluoromethoxy, R¹ is methyl and R² is methoxycarbonyl;

Q is 4-difluoromethoxy, R¹ is methyl, R² is methoxycarbonyl and G is 4-chloro, 4-trifluoromethyl, 4-difluoromethoxy, 4-trifluoromethoxy, 4-(1,1,2,2-tetrafluoroethoxy), 4-(1,1,2,3,3,3-hexafluoropropyloxy), or 4-isopropyloxycarbonyl; or Q is hydrogen, R¹ is methyl, R² is methoxycarbonyl and G is 4-trifluoromethyl or 4-trifluoromethoxy.

In another embodiment of this class are compounds of the structure

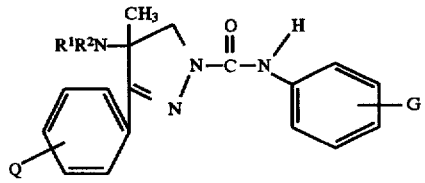

wherein

Q is hydrogen, halo or halo($C_1$–$C_6$)alkoxy;

G is halo, halo($C_1$–$C_6$)alkyl or halo($C_1$–$C_6$)alkoxy;

R¹ is ($C_1$–$C_6$)alkyl, ($C_3$–$C_6$)alkenyl, ($C_3$–$C_6$)alkynyl, phenyl($C_1$–$C_6$)alkyl, phenyl or halophenyl;

R² is ($C_1$–$C_6$)alkyl, ($C_1$–$C_6$)alkylsulfonyl, ($C_1$$C_6$)alkoxy ($C_1$–$C_6$)alkyl, ($C_1$–$C_6$)alkoxycarbonyl, halo($C_1$–$C_6$) alkoxycarbonyl, formyl, ($C_1$–$C_6$)alkylcarbonyl, di($C_1$–$C_6$)alkylaminocarbonyl or phenylcarbonyl; or R¹ and R² together with the nitrogen to which they are attached form 2-oxazolidonyl, isomorpholin-2-onyl, pyrrolidinonyl, piperidonyl or succinimidyl.

More preferred compounds of this embodiment are those wherein Q is 4-halo, G is 4-halo($C_1$–$C_6$)alkyl or 4-halo. R¹ is ($C_1$–$C_6$)alkyl or benzyl, R² is ($C_1$–$C_6$)alkyl, ($C_1$–$C_6$) alkylsulfonyl, ($C_1$–$C_6$)alkylcarbonyl or ($C_1$–$C_6$) alkoxycarbonyl; or R¹ and R² together with the nitrogen to which they are attached form 2-oxazolidonyl, isomorpholin-2-onyl, pyrrolidinonyl, piperidonyl or succinimidyl.

Most preferred are compounds wherein Q is 4-chloro, G is 4-trifluoromethyl, R¹ is methyl and R² is methyl or methoxycarbonyl; or Q is chloro, G is 4-trifluoromethyl, R¹ is ethyl and R² is methoxycarbonyl.

In yet another embodiment of this class are compounds of the formula

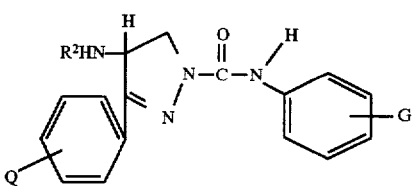

wherein

Q is hydrogen, halo, halo($C_1$–$C_6$)alkoxy or ($C_1$–$C_6$)alkoxy;

G is halo, halo($C_1$–$C_6$)alkyl or halo($C_1$–$C_6$)alkoxy; and $R^2$ is hydrogen, ($C_1$–$C_6$)alkyl, phenyl($C_1$–$C_6$)alkyl, cyano, ($C_1$–$C_6$)alkoxycarbonyl, halo($C_1$–$C_6$)alkoxycarbonyl, (($C_1$–$C_6$)alkylthio)carbonyl, halo($C_1$–$C_6$)alkoxycarbonyl, cyano($C_1$–$C_6$)alkoxycarbonyl, ($C_1$–$C_6$)alkoxy($C_1$–$C_6$)alkoxycarbonyl, ($C_1$–$C_6$)alkoxycarbonyl($C_1$–$C_6$)alkoxycarbonyl, phenoxycarbonyl, phenyl($C_1$–$C_6$)alkoxycarbonyl, ($C_3$–$C_6$)alkenyloxycarbonyl, ($C_3$–$C_6$)alkynyloxycarbonyl, formyl, ($C_1$–$C_6$)alkylcarbonyl, halo($C_1$–$C_6$)alkylcarbonyl, carboxy($C_1$–$C_6$)alkylcarbonyl, phenylcarbonyl, phenyl($C_1$–$C_6$)alkylcarbonyl, phenyl($C_2$–$C_6$)alkenylcarbonyl, mono($C_1$–$C_6$)alkylaminocarbonyl, di($C_1$–$C_6$)alkylaminocarbonyl, phenylaminocarbonyl, ($C_1$–$C_6$)alkoxycarbonyl($C_1$–$C_6$)alkylaminocarbonyl, phenyl(($C_1$–$C_6$)alkyl)aminocarbonyl, di($C_1$–$C_6$)alkylphosphoryl, di($C_1$–$C_6$)alkylthiophosphoryl, ($C_1$–$C_6$)alkylsulfonyl, ($C_2$–$C_6$)alkenylsulfonyl, halo($C_1$–$C_6$)alkylsulfonyl, phenylsulfonyl, di($C_1$–$C_6$)alkylaminosulfonyl, 2-pyridyl or 2-pyrazinyl.

More preferred are compounds wherein Q is hydrogen, 4-halo($C_1$–$C_6$)alkoxy or 4-halo; G is 4-halo($C_1$–$C_6$)alkyl or 4-halo($C_1$–$C_6$)alkoxy and $R^2$ is hydrogen, ($C_1$–$C_6$)alkoxycarbonyl, halo($C_1$–$C_6$)alkoxycarbonyl, formyl, ($C_1$–$C_6$)alkylcarbonyl, halo($C_1$–$C_6$)alkylcarbonyl, ($C_1$–$C_6$)alkylcarbonyl and ($C_1$–$C_6$)alkylsulfonyl.

Most preferred are the compounds wherein Q is hydrogen, G is 4-trifluoromethyl and $R^2$ is methoxycarbonyl; Q is 4-chloro, G is 4-trifluoromethyl and $R^2$ is methoxycarbonyl; Q is 4-chloro, G is 4-trifluoromethoxy and $R^2$ is methoxycarbonyl; and Q is 4-chloro, 4-n-butyloxy, 4-n-propyloxy or 4-difluoromethoxy, G is 4-trifluoromethyl, 4-trifluoromethoxy or 4-(1,1,2,2-tetrafluoroethoxy), and $R^2$ is n-propyl.

In another embodiment of this class are compounds of the formula

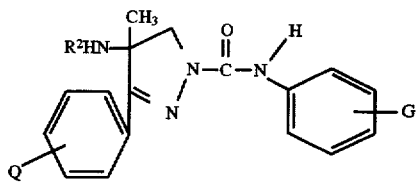

wherein

Q is hydrogen, halo or ($C_1$–$C_6$)alkoxy;

G is halo, halo($C_1$–$C_6$)alkyl or halo($C_1$–$C_6$)alkoxy; and $R^2$ is hydrogen, ($C_1$–$C_6$)alkyl, phenyl($C_1$–$C_6$)alkyl, cyano, ($C_1$–$C_6$)alkoxycarbonyl, halo($C_1$–$C_6$)alkoxycarbonyl, (($C_1$–$C_6$)alkylthio)carbonyl, halo($C_1$–$C_6$)alkoxycarbonyl, cyano($C_1$–$C_6$)alkoxycarbonyl, ($C_1$–$C_6$)alkoxy($C_1$–$C_6$)alkoxycarbonyl, ($C_1$–$C_6$)alkoxycarbonyl($C_1$–$C_6$)alkoxycarbonyl, phenoxycarbonyl, phenyl($C_1$–$C_6$)alkoxycarbonyl, ($C_3$–$C_6$)alkenyloxycarbonyl, ($C_3$–$C_6$)alkynyloxycarbonyl, formyl, ($C_1$–$C_6$)alkylcarbonyl, halo($C_1$–$C_6$)alkylcarbonyl, carboxy($C_1$–$C_6$)alkylcarbonyl, phenylcarbonyl, phenyl($C_1$–$C_6$)alkylcarbonyl, phenyl($C_2$–$C_6$)alkenylcarbonyl, mono($C_1$–$C_6$)alkylaminocarbonyl, di($C_1$–$C_6$)alkylaminocarbonyl, phenylaminocarbonyl, ($C_1$–$C_6$)alkoxycarbonyl($C_1$–$C_6$)alkylaminocarbonyl, phenyl(($C_1$–$C_6$)alkyl)aminocarbonyl, di($C_1$–$C_6$)alkylphosphoryl, di($C_1$–$C_6$)alkylthiophosphoryl, ($C_1$–$C_6$)alkylsulfonyl, ($C_2$–$C_6$)alkenylsulfonyl, halo($C_1$–$C_6$)alkylsulfonyl, phenylsulfonyl, di($C_1$–$C_6$)alkylaminosulfonyl, 2-pyridyl or 2-pyrazinyl.

More preferred are compounds wherein Q is 4-halo or 4-($C_1$–$C_6$)alkoxy; G is 4-halo($C_1$–$C_6$)alkyl; and $R^2$ is hydrogen, ($C_1$–$C_6$)alkoxycarbonyl, halo($C_1$–$C_6$)alkoxycarbonyl, ($C_3$–$C_6$)alkynyloxycarbonyl, ($C_1$–$C_6$)alkylcarbonyl, phenylcarbonyl or (($C_1$–$C_6$)alkylthio)carbonyl.

Most preferred are compounds wherein Q is 4-chloro, G is 4-trifluoromethyl and $R^2$ is hydrogen, methoxycarbonyl, ethoxycarbonyl, n-propyloxycarbonyl, isopropyloxycarbonyl, t-butyloxycarbonyl, 2-chloroethoxycarbonyl, propargyloxycarbonyl, methylcarbonyl, phenylcarbonyl or (ethylthio)carbonyl; and Q is 4-n-propyloxy, G is 4-trifluoromethyl and $R^2$ is methoxycarbonyl or ethoxycarbonyl.

In another class of the preferred embodiment of the invention is the compound of Formula I wherein V is ($C_1$–$C_6$)alkyl, ($C_1$–$C_6$)alkoxy($C_1$–$C_6$)alkyl, formyl, ($C_1$–$C_6$)alkylcarbonyl, ($C_1$–$C_6$)alkylaminocarbonyl, ($C_1$–$C_6$)alkoxycarbonyl, ($C_3$–$C_6$)alkenyloxycarbonyl, phenyloxycarbonyl, ($C_1$$C_6$)alkoxycarbonylcarbonyl, cyano($C_1$–$C_6$)alkylthio, ($C_1$–$C_6$)alkylthio, phenylthio, ($C_1$–$C_6$)alkoxycarbonyl($C_1$–$C_6$)alkylthio or ($C_1$–$C_6$)alkoxycarbonylthio;

Y is isothiocyanato, isocyano, —$NR^1R^2$, ($C_1$–$C_6$)alkanoyloxy, ($C_1$–$C_6$)alkoxy, phenyloxy, ($C_1$–$C_6$)alkylthio, ($C_1$–$C_6$)alkylsulfonyl or phenylthio; and the remaining substituents are as defined above.

Preferred are compounds of the structure

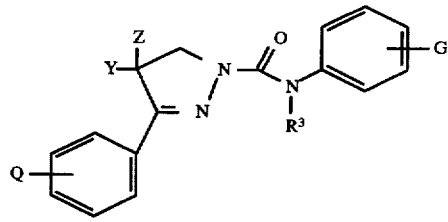

wherein

Q is halo;

G is halo or halo($C_1$–$C_6$)alkyl;

Y is $NR^1R^2$;

$R^1$ is hydrogen or ($C_1$–$C_6$)alkyl;

$R^2$ is ($C_1$–$C_6$)alkoxycarbonyl;

$R^3$ is ($C_1$–$C_6$)alkyl; and

Z is hydrogen or ($C_1$–$C_6$)alkyl.

More preferred are compounds wherein Q is 4-halo, G is 4-halo or 4-halo($C_1$–$C_6$)alkyl; $R^1$ is hydrogen or ($C_1$–$C_6$)alkyl $R^2$ is ($C_1$–$C_6$)alkoxycarbonyl; $R^3$ is ($C_1$–$C_6$)alkyl and Z is hydrogen.

Most preferred are compounds wherein Q is 4-chloro, G is 4-chloro, R¹ is methyl, R² is methoxycarbonyl, R³ is methyl and Z is hydrogen; Q is 4-chloro, G is 4-trifluoromethyl, R¹ is hydrogen, R² is methoxycarbonyl, R³ is methyl and Z is hydrogen; and Q is 4-chloro, G is 4-trifluoromethyl, R¹ is methyl, R² is methoxycarbonyl, R³ is methyl and Z is hydrogen.

In yet another class of the preferred embodiment of the invention is the compound of Formula I wherein Y is $(C_1-C_6)$alkanoyloxy, $(C_1-C_6)$alkoxy or phenyloxy and the remaining substituents are as defined above.

More preferred are compounds of the structure

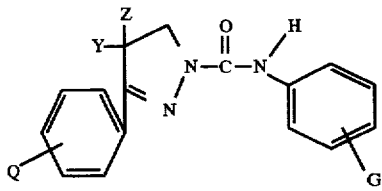

wherein

Q is halo;

G is halo$(C_1-C_6)$alkyl;

Z is hydrogen or methyl; and

Y is $(C_1-C_6)$alkoxy, phenyloxy, halophenyloxy or $(C_1-C_6)$alkanoyloxy.

In one embodiment of this class, more preferred are compounds wherein Q is 4-halo; G is 4-halo$(C_1-C_6)$alkyl; Z is hydrogen; and Y is $(C_1-C_6)$alkoxy, phenyloxy, 4-halophenyloxy or $(C_1-C_6)$alkanoyloxy.

Most preferred is the compound wherein Q is 4-chloro; G is 4-trifluoromethyl; Z is methyl; and Y is methoxy.

In another embodiment of this class are compounds wherein Q is 4-halo; G is 4-halo$(C_1-C_6)$alkyl; Z is methyl; and Y is methoxy, n-propyloxy, phenyloxy, 4-chlorophenyloxy or acetoxy.

Most preferred are the compounds wherein Q is 4-chloro; G is 4-trifluoromethyl; Z is methyl; and Y is methoxy, n-propyloxy or acetoxy.

In another class of the preferred embodiment of the invention is the compound of Formula I wherein Y is $(C_1-C_6)$alkylthio, $(C_1-C_6)$alkylsulfonyl or phenylthio and the remaining substituents are as defined above.

Preferred are compounds of the structure

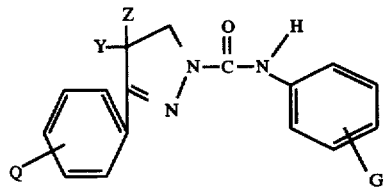

wherein

Q is halo;

G is halo$(C_1-C_6)$alkyl;

Z is hydrogen or methyl; and

Y is $(C_1-C_6)$alkylthio or $(C_1-C_6)$alkylsulfonyl.

More preferred are compounds wherein Q is 4-halo, G is 4-halo$(C_1-C_6)$alkyl, Z is hydrogen and Y is $(C_1-C_6)$alkylthio or $(C_1-C_6)$alkylsulfonyl.

Most preferred are the compounds wherein Q is 4-chloro, G is 4-trifluoromethyl, Z is hydrogen and Y is methylthio or methylsulfonyl.

In yet another class of the preferred embodiment of the invention is a compound of the formula

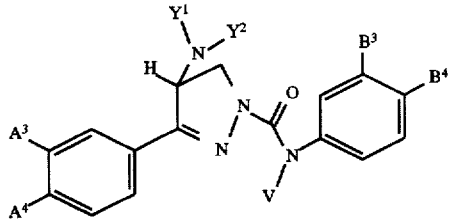

wherein $A^3$ and $A^4$ are each independently a hydrogen atom, alkyl, halo, haloalkyl, polyhaloalkyl, alkoxy, haloalkoxy, polyhaloalkoxy, alkoxyalkoxy, alkoxycarbonyl or nitro;

$B^3$ is a hydrogen atom, halo, haloalkyl, polyhaloalkyl, haloalkoxy or polyhaloalkoxy;

$B^4$ is halo, haloalkyl, polyhaloalkyl, haloalkoxy or polyhaloalkoxy;

V is a hydrogen atom, alkyl, alkylcarbonyl, alkoxycarbonyl or formyl;

$Y^1$ is a hydrogen atom, alkyl, alkenyl, alkynyl, phenyl, halophenyl, alkoxyalkyl, alkoxycarbonylalkyl or cyanoalkyl;

$Y^2$ is a hydrogen atom, alkyl, alkoxycarbonyl, phenalkoxycarbonyl, phenoxycarbonyl, haloalkoxycarbonyl, polyhaloalkoxycarbonyl, alkoxyalkoxycarbonyl, alkenyloxycarbonyl, alkynyloxycarbonyl, formyl, alkylcarbonyl, haloalkylcarbonyl, polyhaloalkylcarbonyl, benzoyl, alkenylcarbonyl, polyhaloalkenylcarbonyl, alkylcarbonylcarbonyl, alkoxycarbonylcarbonyl, alkylthiocarbonyl, alkylsulfonyl, phenylsulfonyl, halophenylsulfonyl, phenylaminocarbonyl, polyhaloalkoxyphenylaminocarbonyl, cyano, monoalkylaminocarbonyl or dialkylaminocarbonyl, dialkylphosphoryl or dialkylthiophosphoryl wherein the alkyl groups are the same or different; or agronomically acceptable salts thereof.

Preferred compounds of this embodiment are those wherein $A^3$ and $A^4$ are each independently a hydrogen atom, $(C_1-C_6)$alkyl, fluoro, chloro, bromo, polyhalo$(C_1-C_2)$ alkyl wherein the halo is independently selected from fluoro, chloro or bromo, $(C_1-C_6)$alkoxy, polyhalo $(C_1-C_4)$alkoxy wherein the halo is independently selected from fluoro, chloro or bromo, $(C_1-C_2)$alkoxy $(C_1-C_6)$alkoxy, $(C_1-C_4)$alkoxycarbonyl or nitro;

$B^3$ is a hydrogen atom, chloro, fluoro, bromo, polyhalo $(C_1-C_2)$alkyl wherein the halo is independently selected from fluoro, chloro or bromo, or polyhalo $(C_1-C_4)$alkoxy wherein the halo is independently selected from fluoro, chloro or bromo;

$B^4$ is chloro, bromo, polyhalo$(C_1-C_2)$alkyl wherein the halo is independently selected from fluoro, chloro or bromo, or polyhalo$(C_1-C_4)$alkoxy wherein the halo is independently selected from fluoro, chloro or bromo;

V is a hydrogen atom, $(C_1-C_2)$alkyl, $(C_1-C_2)$ alkylcarbonyl, $(C_1-C_2)$alkoxycarbonyl or formyl;

$Y^1$ is a hydrogen atom, $(C_1-C_6)$alkyl, $(C_2-C_4)$alkenyl, $(C_2-C_4)$alkynyl, phenyl, 4-halophenyl, $(C_1-C_4)$alkoxy $(C_1-C_4)$alkyl or cyano$(C_1-C_3)$alkyl; and $Y^2$ is a hydrogen atom, $(C_1-C_6)$alkyl, $(C_1-C_6)$ alkoxycarbonyl, phen$(C_1-C_2)$alkoxycarbonyl, phenoxycarbonyl, halo($C_1$-$C_4$)alkoxycarbonyl wherein the halo is fluoro, chloro or bromo, polyhalo ($C_1$-$C_3$)alkoxycarbonyl wherein the halo is independently selected from fluoro, chloro or bromo, ($C_1$-$C_2$) alkoxy($C_1$-$C_3$)alkoxycarbonyl, ($C_2$-$C_4$) alkenyloxycarbonyl, ($C_2$-$C_4$)alkynyloxycarbonyl, formyl, ($C_1$-$C_6$)alkylcarbonyl, polyhalo($C_1$-$C_2$) alkylcarbonyl wherein the halo is independently selected from fluoro, chloro or bromo, benzoyl, ($C_2$-$C_4$)alkenylcarbonyl, polyhalo($C_2$-$C_4$) alkenylcarbonyl, ($C_1$-$C_2$)alkylcarbonylcarbonyl, ($C_1$-$C_3$)alkylthiocarbonyl, ($C_1$-$C_3$)alkylsulfonyl, phenylsulfonyl, 4-halophenylsulfonyl, phenylaminocarbonyl, 4-(polyhalo($C_1$-$C_2$)alkoxy) phenylaminocarbonyl, cyano, mono($C_1$-$C_2$) alkylaminocarbonyl or di($C_1$-$C_2$)alkylaminocarbonyl, di($C_1$-$C_2$)alkylphosphoryl or di($C_1$-$C_2$) alkylthiophosphoryl wherein the alkyl groups are the same or different.

More preferred compounds are those wherein $A^3$ and $A^4$ are each independently a hydrogen atom, methyl, ethyl, n-propyl, n-butyl, fluoro, chloro, bromo, trifluoromethyl, methoxy, ethoxy, n-propoxy, n-butoxy, trifluoromethoxy, difluoromethoxy, 1,1,2,2-tetrafluoroethoxy, 1,1,2,3,3,3-hexafluoropropoxy, 2-chloro-1,1,2-trifluoroethoxy, bromodifluoromethoxy, 2-bromo-1,1,2,2-tetrafluoroethoxy, 2-methoxyethoxy, methoxycarbonyl, ethoxycarbonyl or nitro;

$B^3$ is a hydrogen atom, chloro, fluoro, bromo, trifluoromethyl, trifluoromethoxy, difluoromethoxy or 1,1,2,2-tetrafluoroethoxy;

$B^4$ is chloro, bromo, trifluoromethyl, trifluoromethoxy, difluoromethoxy, 1,1,2,2-tetrafluoroethoxy, 1,1,2,3,3,3-hexafluoropropoxy, 2-chloro-1,1,2-trifluoroethoxy, bromodifluoromethoxy or 2-bromo-1,1,2,2-tetrafluoroethoxy;

V is a hydrogen atom, methyl, methylcarbonyl, methoxycarbonyl or formyl;

$Y^1$ is a hydrogen atom, methyl, ethyl, n-propyl, isopropyl, n-butyl, allyl or propargyl; and $Y^2$ is a hydrogen atom, methoxycarbonyl, ethoxycarbonyl, n-propoxycarbonyl, isopropoxycarbonyl, tert-butoxycarbonyl, benzyloxycarbonyl, phenoxycarbonyl, chloromethoxycarbonyl, bromomethoxycarbonyl, 2-chloroethoxycarbonyl, 2-bromoethoxycarbonyl, 3-chloro-1-propoxycarbonyl, 3-bromo-1-propoxycarbonyl, 2,2,2-trifluoroethoxycarbonyl, 2-methoxyethoxycarbonyl, allyloxycarbonyl, propargyloxycarbonyl, formyl, methylcarbonyl, ethylcarbonyl, isopropylcarbonyl, tert-butylcarbonyl, trifluoromethylcarbonyl, benzoyl, vinylcarbonyl, isopropenylcarbonyl, methylcarbonylcarbonyl, methylthiocarbonyl, ethylthiocarbonyl, methylsulfonyl, ethylsulfonyl, phenylsulfonyl, methylaminocarbonyl, dimethylaminocarbonyl, diethylphosphoryl or diethylthiophosphoryl.

Even more preferred compounds are those wherein $A^3$ is a hydrogen atom, chloro, methoxy, difluoromethoxy, ethoxy, n-propoxy, methyl or n-propyl;

$A^4$ is chloro, trifluoromethyl, difluoromethoxy, n-propoxy or n-propyl;

$B^3$ is a hydrogen atom or chloro;

$B^4$ is trifluoromethyl, trifluoromethoxy or 1,1,2,2-tetrafluoroethoxy;

V is a hydrogen atom;

$Y^1$ is a hydrogen atom, methyl or n-propyl; and $Y^2$ is a hydrogen atom, methoxycarbonyl, formyl or methylcarbonyl.

A process for preparing many of the compounds of the invention starts from compounds disclosed in U.S. Pat. No. 4,863,947 according to the following general synthesis shown in Scheme 1.

More particularly, in the case where Y is attached to the pyrazoline ring by a nitrogen, the starting pyrazoline (III), wherein R is alkyl and A, B, U, V and Z are as defined above, contains a carboxylic acid ester at the Y-position. The ester is saponified to yield the corresponding carboxylic acid (IV) under normal saponification conditions. Preferred solvents are protic solvents such as methanol or solvent mixtures such as methanol and tetrahydrofuran at temperatures between about 0° C. and about 100° C., more preferably between about 25° and about 75°.

The acid is then converted to the acid chloride (V) by known means, for example, treatment with thionyl chloride. Preferred solvents are toluene and chloroform.

The acid chloride is reacted with azide anion, for example, sodium azide, to yield the azidocarbonyl compound (VI). Preferred solvents are acetonitrile and dimethylformamide.

The azidocarbonyl compound is then converted to the corresponding isocyanate (VII) by heating in an appropriate solvent until gas evolution ceases. Preferred solvents are toluene, benzene, and chlorobenzene.

Scheme 1

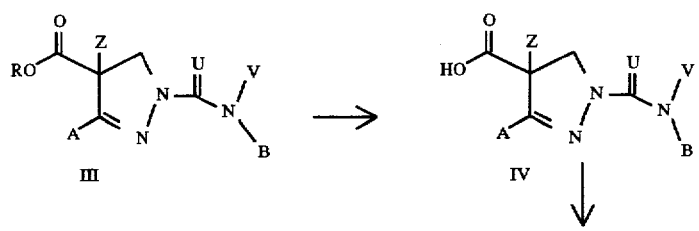

-continued
Scheme 1

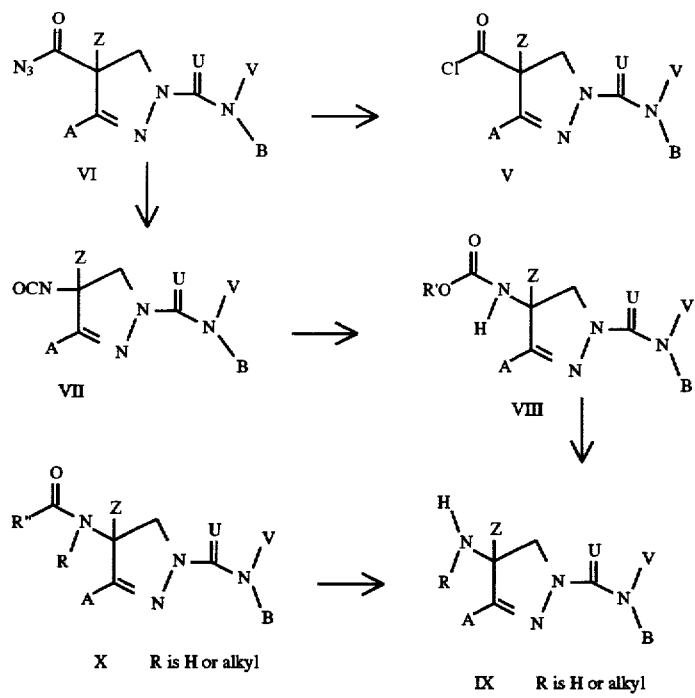

The carboalkoxyamino compounds of the invention (VIII) are obtained by reacting the isocyanato compounds with the appropriate alcohol. The alcohol can be used as the solvent, for example methanol or ethanol, or alternatively a slight excess of the alcohol along with a base is used in a inert solvent. Preferred solvents are benzene and toluene.

In the case where the compound (VIII) is a t-butyloxycarbonylamino compound and the like, the carboalkoxyamino compound can then be decarbalkoxylated to yield the corresponding amino compound (IX; R=H) by heating in an inert solvent in the presence of acid. Preferred solvents include halogenated solvents such as chloroform and methylene chloride. Preferred acids include, for example, trifluoroacetic acid and toluenesulfonic acid.

Compounds IX where R=H can be converted to the corresponding compounds where R=alkyl by standard means known to those skilled in the art. For example by treatment with and alkyl halide such as methyl iodide or benzyl bromide in a solvent. Preferred solvents include ethanol, acetonitrile, and dimethylformamide. Alternatively, treatment with an aldehyde and sodium cyanoborohydride under acidic conditions can also effect alkylation. Preferred solvents include methanol and ethanol. Preferred acids include acetic acid.

The corresponding carboxamide compounds (X), and the like, are prepared from the amino compound (IX) by treatment with the appropriate acid chloride in the presence of base. Preferred solvents are methylene chloride and tetrahydrofuran. Preferred bases include pyridine and triethylamine.

Alternatively, the amino-substituted compounds are prepared using the synthesis shown in Scheme 2.

Scheme 2

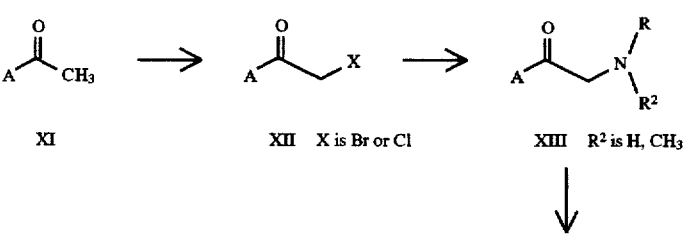

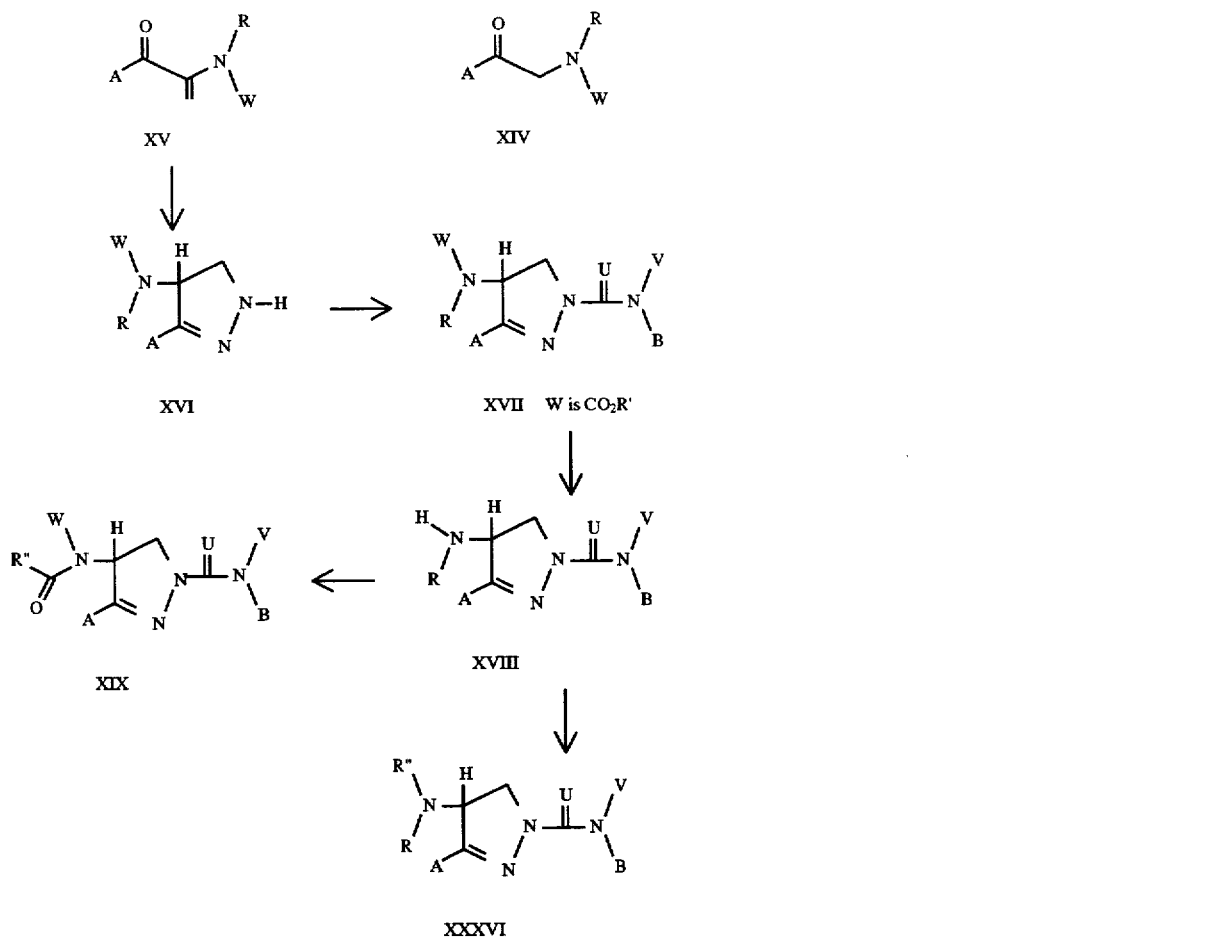

More particularly, a methyl ketone (XI) is halogenated using conditions known in the art. The halo compound (XII) is reacted with a mono- or di-alkylamine under known conditions to obtain the resulting alkylaminomethyl ketone (XIII). The reaction is typically carried out at a temperature between about −50° C. and 20° C. in a non-protic solvent, for example, methylene chloride.

The alkylaminomethyl ketone is acylated with an acylating agent, for example, with an alkyl chloroformate such as methyl chloroformate, ethyl chloroformate, propyl chloroformate, or isopropyl chloroformate or an alkanoyl chloride or anhydride such as propionyl chloride, propionic anhydride, acetic anhydride, acetyl chloride, butyryl chloride, isobutyryl chloride, trifluoroacetic anhydride, methane sulfonyl chloride, valeryl chloride, 2-methylbutyryl chloride, 3-methylbutyryl chloride or hexanoyl chloride, to produce the substituted compound (XIV) where W is acyl. Preferred solvents are aprotic solvents such as methylene chloride at a temperature between about −25° C. and about 50° C., more preferably between about 0° C. and about 20° C.

The acyl compound is then treated with formaldehyde to obtain the corresponding prop-2-enone (XV). Preferred solvents are protic solvents such as propanol or 2-methoxyethanol at temperatures between about 0° C. and about 140° C., preferably at about the reflux temperature of the solvent used. Preferably catalytic amounts of a base such as piperidine and an acid such as acetic acid are also present in the reaction mixture.

The resulting prop-2-enone is then converted to the corresponding dihydropyrazole (XVI) by treatment with hydrazine. Preferred solvents are protic solvents such as methanol at temperatures between about 0° C. and about 100° C., preferably between about 25° C. and about 70° C. The resulting dihydropyrazole is generally reacted with an appropriate isocyanate as described in U.S. Pat. No. 4,863,947 to obtain the corresponding carboxamide (XVII).

When W is carboalkoxy, the carboxamide (XVII) can be decarboxylated by known means to obtain the disubstituted amino compound (XVIII). Preferred, when R' is 2,2,2-trichloroethoxycarbonyl, are reagents such as acetic acid and zinc dust in protic solvents such as methanol at temperatures from about 0° C. to about 100° C., more preferably from about 20° C. to about 70° C.

The amino dihydropyrazole (XVIII) is then acylated under standard conditions to yield the corresponding acylated amino compound XIX. Preferred solvents are aprotic solvents such as ethyl acetate at temperatures between about −25° C. and about 50° C., more preferably between about 0° C. and about 20° C.

Alternatively, the amino dihydropyrazole (XVIII) can be alkylated with either an alkyl halide or an aldehyde/sodium cyanoborohydride as described above yielding Compound XXXVI.

When R is hydrogen, hexamethylenetetramine is used as the amine to yield, after hydrolysis, the amino compound (XVIII) wherein R and R2 are both hydrogen. The amino compound is subsequently acylated and treated with formaldehyde to give the corresponding prop-2-enone (XV) wherein R is hydrogen.

The reaction with hexamethylenetetramine is generally carried out in a solvent such as acetonitrile at temperatures between 0° C. and 100° C. and preferably at temperatures between 20° C. and 70° C. The hydrolysis of the resulting quaternary salt is generally carried out in a solvent such as methanol or ethanol with aqueous acids such as hydrochloric acid at temperatures between 0° C. and 100° C. and preferably at temperatures between 20° C. and 50° C.

The S-alkyl compounds of the formula

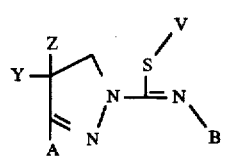

are prepared by alkylating the corresponding thiocarboxamide with the appropriate alkyl halide according to known procedures.

The corresponding oxygen and sulfur compounds are prepared as shown in Schemes 3, 4, 5, and 6 starting from the halomethylketone XII which is alkoxylated or alkylthiolated under known conditions to yield the corresponding oxygen (XX) or sulfur (XXIX) compounds. Alternatively, the alkoxyacetonitrile (XXIII) can be reacted with reagents such as 4-chlorophenylmagnesium bromide by known methods to yield, after hydrolysis, the appropriate alkoxy acetophenone (XXIV). The sulfur compound (XXIX) is optionally oxidized to the corresponding sulfone (XXXIII) using standard conditions and reagents. Preferably, oxidating agents such as peracetic acid or m-chloroperbenzoic acid are used in aprotic solvents such as methylene chloride at temperatures between about −50° C. and about 50° C., more preferably between about −10° C. and about 10° C. These keto compounds are then converted to compounds of the invention using the steps analagous to the preparation of the amino compounds discussed above.

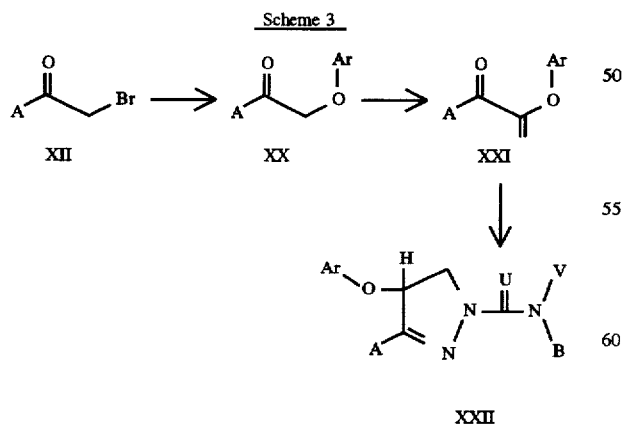

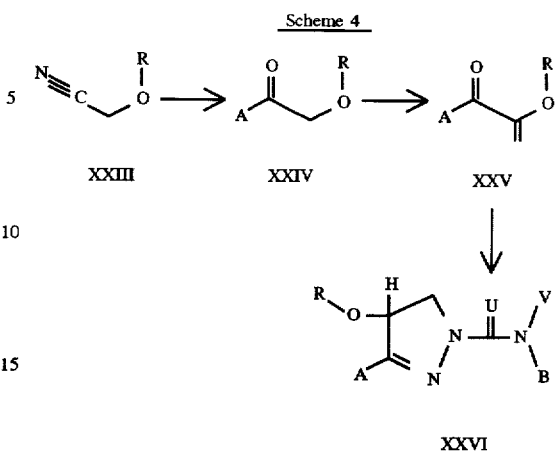

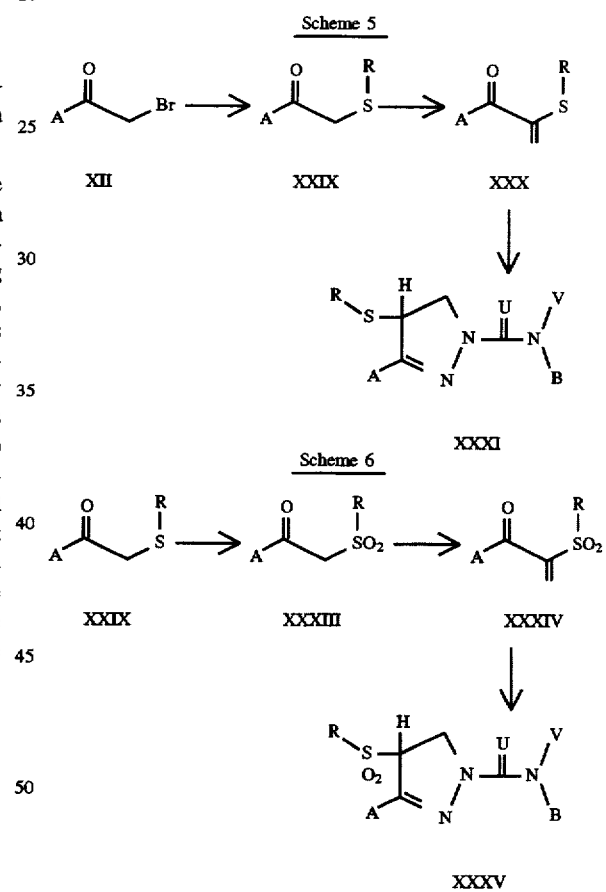

The following examples will further illustrate this invention but are not intended to limit it in any way. In Table I, typical 1-substituted-4-substituted-4,5-dihydro-1H-pyrazoles of the present invention are listed. Structures were confirmed by NMR and in some cases by IR and/or elemental analysis. Table II contains NMR data for those examples of Table I which were oils. Specific illustrative preparations of compounds of the invention are described. It will be appreciated by those skilled in the art that the Y and Z substituents can be interchanged without departing from the spirit or scope of the present invention.

TABLE I

| EX. | Q | G | Y | Z | V | mp °C. |
|---|---|---|---|---|---|---|
| 1. | 4-Cl | 4-CF₃ | NHCO₂CH₃ | CH₃ | H | 179–181 |
| 2. | 4-Cl | 4-CF₃ | NHCO₂C(CH₃)₃ | CH₃ | H | 205–206 |
| 3. | 4-Cl | 4-CF₃ | NH₂ | CH₃ | H | 165–167 |
| 4. | 4-Cl | 4-CF₃ | NHCONHCH₃ | CH₃ | H | 145–157 |
| 5. | 4-Cl | 4-CF₃ | NHSO₂CH₃ | CH₃ | H | 215–217 |
| 6. | 4-Cl | 4-CF₃ | NHCOCH₃ | CH₃ | H | 232–235 |
| 7. | 4-Cl | 4-CF₃ | NHCOC₆H₅ | CH₃ | H | 241–246 |
| 8. | 4-Cl | 4-CF₃ | NHCO₂CH₂CH₃ | CH₃ | H | 173–175 |
| 9. | 4-Cl | 4-CF₃ | NHCO₂CH₂CH₂CH₃ | CH₃ | H | 130–133 |
| 10. | 4-Cl | 4-CF₃ | NHCO₂CH(CH₃)₂ | CH₃ | H | 120–125 |
| 11. | 4-Cl | 4-CF₃ | NHCO₂CH₂C₆H₅ | CH₃ | H | oil |
| 12. | 4-Cl | 4-CF₃ | NHCON(CH₃)₂ | CH₃ | H | 208–210 |
| 13. | 4-Cl | 4-CF₃ | O(C=O)CH₃ | CH₃ | H | 92–96 |
| 14. | 4-Cl | 4-CF₃ | NHCO₂(CH₂)₃CH₃ | CH₃ | H | 99–103 |
| 15. | 4-Cl | 4-CF₃ | NHCO₂(CH₂)₄CH₃ | CH₃ | H | oil |
| 16. | 4-Cl | 4-CF₃ | NHCO₂CH₂CH₂OCH₃ | CH₃ | H | 85–88 |
| 17. | 4-Cl | 4-CF₃ | NHCO₂CH₂CH₂Cl | CH₃ | H | 100–102 |
| 18. | 4-Cl | 4-CF₃ | NHCO₂C₆H₅ | CH₃ | H | 194–196 |
| 19. | 4-Cl | 4-CF₃ | NHCO₂CH₂COCH₃ | CH₃ | H | 152–154 |
| 20. | 4-Cl | 4-CF₃ | NHCO₂CH₂C≡CH | CH₃ | H | 165–166 |
| 21. | 4-Cl | 4-CF₃ | NHCO₂CH₂CF₃ | CH₃ | H | 110–140 |
| 22. | 4-Cl | 4-CF₃ | NHCOSCH₂CH₃ | CH₃ | H | 190–191 |
| 23. | 4-Cl | 4-CF₃ | NHCO₂CH₂CH=CH₂ | CH₃ | H | 143–145 |
| 24. | 4-Cl | 4-CF₃ | NHCOCH₂CH₃ | CH₃ | H | 208–209 |
| 25. | 4-Cl | 4-CF₃ | NHCOCH₂CH₂CH₃ | CH₃ | H | 198–191 |
| 26. | 4-Cl | 4-CF₃ | NHSO₂C₆H₅ | CH₃ | H | 204–206 |
| 27. | 4-Cl | 4-CF₃ | NHCONHC₆H₅ | CH₃ | H | 125–135 |
| 28. | 4-Cl | 4-CF₃ | NHCOCF₃ | CH₃ | H | 219–220 |
| 29. | 4-Cl | 4-CF₃ | NHCOCH(CH₃)₂ | CH₃ | H | 213–216 |
| 30. | 4-Cl | 4-CF₃ | NHCOC(CH₃)₃ | CH₃ | H | 210–212 |
| 31. | 4-Cl | 4-CF₃ | N(CH₃)CO₂CH₃ | CH₃ | H | 193–194 |
| 32. | 4-Cl | 4-CF₃ | N(CH₃)CO₂CH₃ | CH₃ | CH₃ | 128–130 |
| 33. | 4-Cl | 4-CF₃ | NHCO₂CH₃ | CH₃ | CH₃ | oil |
| 34. | 4-Cl | 4-Cl | NHCO₂CH₃ | CH₃ | H | 126–128 |
| 35. | 4-Cl | 4-Cl | NHCO₂CH₂CH₃ | CH₃ | H | 156–158 |
| 36. | 4-Cl | 4-Cl | NHCO₂CH₂CH₂CH₃ | CH₃ | H | 149–154 |
| 37. | 4-Cl | 4-Cl | NHCO₂CH(CH₃)₂ | CH₃ | H | 145–148 |
| 38. | 4-Cl | 4-CF₃ | N(CH₃)₂ | CH₃ | H | 189–191 |
| 39. | 4-Cl | 4-CF₃ | NHCOCH₂C₆H₅ | CH₃ | H | 172–174 |
| 40. | 4-Cl | 4-CF₃ | NHCOCH₂CH₂C₆H₅ | CH₃ | H | 174–175 |
| 41. | 4-Cl | 4-CF₃ | NHCOCH=CHC₆H₅ | CH₃ | H | 174–181 |
| 42. | 4-Cl | 4-CF₃ | N(CH₂CH₃)₂ | CH₃ | H | oil |
| 43. | 4-Cl | 4-CF₃ | NHCH₂CH₃ | CH₃ | H | oil |
| 44. | 4-O(CH₂)₂CH₃ | 4-CF₃ | NHCO₂CH₃ | CH₃ | H | 165–166 |
| 45. | 4-O(CH₂)₂CH₃ | 4-CF₃ | NHCO₂CH₂CH₃ | CH₃ | H | 103–105 |
| 46. | 4-O(CH₂)₂CH₃ | 4-CF₃ | NHCO₂CH₂CH₂CH₃ | CH₃ | H | 184–186 |
| 47. | 4-O(CH₂)₂CH₃ | 4-CF₃ | NHCO₂CH(CH₃)₂ | CH₃ | H | 170–173 |
| 48. | 4-Cl | 4-CF₃ | N(CH₂CH₃)C(=O)CH₃ | CH₃ | H | 108–110 |
| 49. | 4-Cl | 4-CF₃ | N(CH₂CH₃)CO₂CH₃ | CH₃ | H | 162–163 |
| 50. | 4-Cl | 4-CF₃ | 2-(NH)-pyridyl | CH₃ | H | 130–140 |
| 51. | 4-Cl | 4-CF₃ | 2-(NH)-pyridyl | CH₃ | H | 135–142 |
| 52. | 4-O(CH₂)₂CH₃ | 4-CF₃ | NHCO₂CH₂CO₂CH₂CH₃ | CH₃ | H | 95–97 |
| 53. | 4-O(CH₂)₂CH₃ | 4-CF₃ | NHCO₂CH₂CN | CH₃ | H | 193–195 |
| 54. | 4-Cl | 4-CF₃ | NHCO₂CH₂CO₂CH₂CH₃ | CH₃ | H | 120–122 |
| 55. | 4-Cl | 4-CF₃ | NHCO₂CH₂CH₂Br | CH₃ | H | 94–97 |
| 56. | 4-Cl | 4-CF₃ | NHCONHCH₂CO₂CH₃ | CH₃ | H | 206–211 |
| 57. | 4-Cl | 4-Cl | N(CH₃)CO₂CH₃ | CH₃ | H | 150–152 |

TABLE I-continued

| EX. | Q | G | Y | Z | V | mp °C. |
|---|---|---|---|---|---|---|
| 58. | 4-Cl | 4-Cl | N(CH₃)CO₂CH₃ | CH₃ | CH₃ | 142–144 |
| 59. | 4-Cl | 4-CF₃ | NCS | CH₃ | H | 99–101 |
| 60. | 4-Cl | 4-CF₃ | 2-oxo-oxazolidin-3-yl | CH₃ | H | 233–235 |
| 61. | 4-Cl | 4-CF₃ | NHCO₂CH₂CH₂CH₂Br | CH₃ | H | 70–90 |
| 62. | 4-Cl | 4-CF₃ | 2-oxo-3-methyl-1,3-oxazinan-3-yl | CH₃ | H | 239–241 |
| 63. | 4-Cl | 4-CF₃ | NHCH(CH₃)₂ | CH₃ | H | oil |
| 64. | 4-Cl | 4-CF₃ | NHCHO | CH₃ | H | 208–210 |
| 65. | 4-Cl | 4-CF₃ | N(CH(CH₃)₂)CO₂CH₃ | CH₃ | H | oil |
| 66. | 4-Cl | 4-CF₃ | NHCH₂C₆H₅ | CH₃ | H | 104–107 |
| 67. | 4-Cl | 4-CF₃ | NHCON(CH₃)C₆H₅ | CH₃ | H | 155–157 |
| 68. | 4-Cl | 4-CF₃ | NHPO(OCH₂CH₃)₂ | CH₃ | H | 75–80 |
| 69. | 4-Cl | 4-CF₃ | NC | CH₃ | H | 171–173 |
| 70. | 4-Cl | 4-CF₃ | NHCN | CH₃ | H | 192–193 |
| 71. | 4-Cl | 4-CF₃ | NHCOCH₂CH₂CH₂Cl | CH₃ | H | 179–181 |
| 72. | 4-Cl | 4-CF₃ | 2-oxo-pyrrolidin-1-yl | CH₃ | H | 204–206 |
| 73. | 4-Cl | 4-CF₃ | NHCO(CH₂)₃CH₂Cl | CH₃ | H | 94–98 |
| 74. | 4-Cl | 4-CF₃ | 2-oxo-piperidin-1-yl | CH₃ | H | 196–198 |
| 75. | 4-Cl | 4-CF₃ | N(CH₂C₆H₅)CO₂CH₃ | CH₃ | H | 169–174 |
| 76. | 4-Cl | 4-CF₃ | OC₆H₅ | H | H | 153–155 |
| 77. | 4-Cl | 4-CF₃ | O-(4-chlorophenyl) | H | H | 195–198 |
| 78. | 4-Cl | 4-CF₃ | NHCOCH₂CH₂CO₂H | CH₃ | H | 150–160 |
| 79. | 4-Cl | 4-CF₃ | NHCO(CH₂)₃CO₂H | CH₃ | H | 110–120 |
| 80. | 4-Cl | 4-CF₃ | 2,5-dioxo-pyrrolidin-1-yl | CH₃ | H | 203–205 |
| 81. | 4-Cl | 4-CF₃ | NHCON(CH₃)CH₂CO₂C₂H₅ | CH₃ | H | 122–125 |
| 82. | 4-Cl | 4-CF₃ | N(CH₃)SO₂CH₃ | CH₃ | H | 105–112 |
| 83. | 4-OCF₂H | 4-OCF₃ | N(CH₃)CHO | H | H | 118–122 |
| 84. | 4-Cl | 4-CF₃ | NHCOCH₂CH(CH₃)₂ | CH₃ | H | 213–215 |
| 85. | 4-Cl | 4-CF₃ | NHCOSCH₂(CH₂)₂CH₃ | CH₃ | H | 228–229 |
| 86. | 4-Cl | 4-CF₃ | NHCOCH₂(CH₂)₂CH₃ | CH₃ | H | 175–177 |
| 87. | 4-Cl | 4-CF₃ | NHCO(CH₂)₄CH₃ | CH₃ | H | 189–192 |
| 88. | 4-Cl | 4-CF₃ | NHCOCF₂CF₃ | CH₃ | H | 163–165 |
| 89. | 4-Cl | 4-CF₃ | NHCOCF₂CF₂CF₃ | CH₃ | H | 172–174 |
| 90. | 4-Cl | 4-CF₃ | NHCOSCH₃ | CH₃ | H | 197–199 |

TABLE I-continued

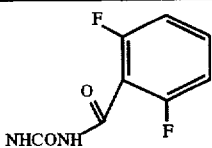

| EX. | Q | G | Y | Z | V | mp °C. |
|---|---|---|---|---|---|---|
| 91. | 4-Cl | 4-CF$_3$ | (2,6-difluorophenyl with NHCONH-C(O)- group) | CH$_3$ | H | 233–234 |
| 92. | 4-Cl | 4-CF$_3$ | N(CH$_3$)CO$_2$CH$_3$ | H | H | 169–171 |
| 93. | 4-Cl | 4-CF$_3$ | N(C$_6$H$_5$)CO$_2$CH$_3$ | H | H | 201–203 |
| 94. | 4-Cl | 4-CF$_3$ | N(4-Cl-C$_6$H$_4$)CO$_2$CH$_3$ | H | H | 199–201 |
| 95. | H | 4-CF$_3$ | NHCO$_2$CH$_3$ | H | H | 189–191 |
| 96. | 4-Cl | 4-CF$_3$ | OCH$_2$CH$_2$CH$_3$ | CH$_3$ | H | 135–138 |
| 97. | 4-Cl | 4-CF$_3$ | NHSO$_2$CH$_2$CH$_3$ | CH$_3$ | H | ~140 |
| 98. | 4-Cl | 4-CF$_3$ | NHSO$_2$CH$_2$CF$_3$ | CH$_3$ | H | ~145 |
| 99. | 4-Cl | 4-CF$_3$ | NHSO$_2$CH$_2$Cl | CH$_3$ | H | ~165 |
| 100. | 4-Cl | 4-CF$_3$ | NHSO$_2$CH=CH$_2$ | CH$_3$ | H | ~165 |
| 101. | 4-Cl | 4-CF$_3$ | NHSO$_2$CH$_2$(CH$_2$)$_2$CH$_3$ | CH$_3$ | H | 181–183 |
| 102. | 4-Cl | 4-CF$_3$ | NHSO$_2$N(CH$_3$)$_2$ | CH$_3$ | H | ~163 |
| 103. | 4-Cl | 4-CF$_3$ | NHSO$_2$CF$_3$ | CH$_3$ | H | ~165 |
| 104. | 4-Cl | 4-CF$_3$ | OCH$_3$ | H | H | 185–186.5 |
| 105. | 4-Cl | 4-CF$_3$ | OCH$_2$CH$_2$CH$_3$ | H | H | 174–175.5 |
| 106. | 4-Cl | 4-CF$_3$ | N(CH$_3$)CO$_2$CH$_2$CH$_3$ | H | H | 144–147 |
| 107. | 4-Cl | 4-CF$_3$ | N(CH$_3$)CO$_2$CH$_2$CH$_2$CH$_3$ | H | H | 135–138 |
| 108. | 4-Cl | 4-CF$_3$ | N(CH$_3$)CO$_2$CH(CH$_3$)$_2$ | H | H | 154–158 |
| 109. | 4-Cl | 4-OCF$_2$CF$_2$H | N(CH$_3$)CO$_2$CH$_3$ | H | H | 191–193 |
| 110. | 4-Cl | 4-OCF$_2$CFHCF$_3$ | N(CH$_3$)CO$_2$CH$_3$ | H | H | 178–180 |
| 111. | 4-Cl | 4-CO$_2$CH$_2$CH$_3$ | N(CH$_3$)CO$_2$CH$_3$ | H | H | 179–180 |
| 112. | 4-Cl | 4-CO$_2$CH(CH$_3$)$_2$ | N(CH$_3$)CO$_2$CH$_3$ | H | H | 155–157 |
| 113. | 4-Cl | 4-OCF$_2$H | N(CH$_3$)CO$_2$CH$_3$ | H | H | 150–151 |
| 114. | 4-Cl | 4-OCF$_3$ | N(CH$_3$)CO$_2$CH$_3$ | H | H | 157–159 |
| 115. | 4-Cl | 4-CF$_3$ | N(CH$_3$)CO$_2$CH$_2$CCl$_3$ | H | H | 169–170 |
| 116. | 4-Cl | 4-CF$_3$ | NHCH$_3$ | H | H | 148–149 |
| 117. | 4-Cl | 4-CF$_3$ | N(CH$_3$)COCH$_3$ | H | H | 219–221 |
| 118. | 4-Cl | 4-CF$_3$ | N(CH$_3$)COC$_6$H$_5$ | H | H | 202–203 |
| 119. | 4-Cl | 4-CF$_3$ | N(CH$_3$)COCH$_2$CH$_3$ | H | H | 213–214 |
| 120. | 4-Cl | 4-CF$_3$ | N(CH$_3$)COCO$_2$CH$_3$ | H | H | 198–199 |
| 121. | 4-Cl | 4-CF$_3$ | N(CH$_3$)CON(CH$_3$)$_2$ | H | H | 197–199 |
| 122. | 4-Cl | 4-CF$_3$ | N(CH$_3$)CHO | H | H | 190–192 |
| 123. | H | 4-CF$_3$ | N(CH$_3$)CO$_2$CH$_3$ | H | H | 175–178 |
| 124. | H | 4-OCF$_3$ | N(CH$_3$)CO$_2$CH$_3$ | H | H | 115–117 |
| 125. | 4-OCF$_2$H | 4-CF$_3$ | N(CH$_3$)CO$_2$CH$_3$ | H | H | 162–163 |
| 126. | 4-OCF$_2$H | 4-OCF$_3$ | N(CH$_3$)CO$_2$CH$_3$ | H | H | 125–126 |
| 127. | 4-OCF$_2$H | 4-Cl | N(CH$_3$)CO$_2$CH$_3$ | H | H | 135–137 |
| 128. | 4-OCF$_2$H | 4-OCF$_2$CFHCF$_3$ | N(CH$_3$)CO$_2$CH$_3$ | H | H | 132–135 |
| 129. | 4-OCF$_2$H | 4-OCF$_2$CF$_2$H | N(CH$_3$)CO$_2$CH$_3$ | H | H | 132–134 |
| 130. | 4-OCF$_2$H | 4-OCF$_2$H | N(CH$_3$)CO$_2$CH$_3$ | H | H | 112–114 |
| 131. | 4-OCF$_2$H | 4-CO$_2$CH(CH$_3$)$_2$ | N(CH$_3$)CO$_2$CH$_3$ | H | H | 144–146 |
| 132. | 4-Cl | 4-Cl | N(CH$_2$CH$_2$CH$_3$)CO$_2$CH$_3$ | H | H | 243–244 |
| 133. | 4-Cl | 4-CF$_3$ | N(CH$_2$CH$_2$CH$_3$)CO$_2$CH$_3$ | H | H | 217–219 |
| 134. | 4-Cl | 4-OCF$_3$ | N(CH$_2$CH$_2$CH$_3$)CO$_2$CH$_3$ | H | H | 184–186 |
| 135. | 4-Cl | 4-OCF$_2$H | N(CH$_2$CH$_2$CH$_3$)CO$_2$CH$_3$ | H | H | 184–186 |
| 136. | 4-Cl | 4-CF$_3$ | N(CH$_2$CH$_3$)CO$_2$CH$_3$ | H | H | 180–181 |
| 137. | 4-Cl | 4-OCF$_3$ | N(CH$_2$CH$_3$)CO$_2$CH$_3$ | H | H | 176–178 |
| 138. | 4-Cl | 4-OCF$_2$CF$_2$H | N(CH$_2$CH$_3$)CO$_2$CH$_3$ | H | H | 194–195 |
| 139. | 4-Cl | 4-CF$_3$ | N(CH$_2$CH=CH$_2$)CO$_2$CH$_3$ | H | H | 192–193 |
| 140. | 4-Cl | 4-OCF$_3$ | N(CH$_2$CH=CH$_2$)CO$_2$CH$_3$ | H | H | 172–174 |
| 141. | 4-Cl | 4-OCF$_2$CF$_2$H | N(CH$_2$CH=CH$_2$)CO$_2$CH$_3$ | H | H | 160–162 |
| 142. | 4-Cl | 4-Cl | N(CH$_2$CH=CH$_2$)CO$_2$CH$_3$ | H | H | 215–218 |
| 143. | 4-Cl | 4-Br | N(CH$_2$CH=CH$_2$)CO$_2$CH$_3$ | H | H | 210–213 |
| 144. | 4-Cl | 4-CF$_3$ | N(CH$_2$C≡CH)CO$_2$CH$_3$ | H | H | 179–180 |

TABLE I-continued

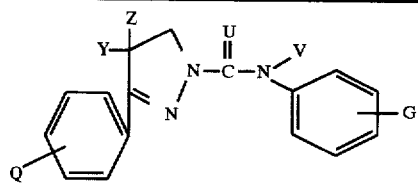

| EX. | Q | G | Y | Z | V | mp °C. |
|---|---|---|---|---|---|---|
| 145. | 4-Cl | 4-OCF$_3$ | N(CH$_2$C|CH)CO$_2$CH$_3$ | H | H | 184–185 |
| 146. | 4-Cl | 4-OCF$_2$CF$_2$H | N(CH$_2$C|CH)CO$_2$CH$_3$ | H | H | 174–175 |
| 147. | 4-Cl | 4-Cl | N(CH$_2$C|CH)CO$_2$CH$_3$ | H | H | 198–200 |
| 148. | 4-Cl | 4-CF$_3$ | NHCO$_2$CH$_3$ | H | H | 226–227 |
| 149. | 4-Cl | 4-OCF$_3$ | NHCO$_2$CH$_3$ | H | H | 216–217 |
| 150. | 4-OCF$_2$CF$_2$H | 4-Cl | N(CH$_3$)CO$_2$CH$_3$ | H | H | 183–184 |
| 151. | 4-OCF$_2$CF$_2$H | 4-CF$_3$ | N(CH$_3$)CO$_2$CH$_3$ | H | H | 167–168 |
| 152. | 4-OCF$_2$CF$_2$H | 4-OCF$_3$ | N(CH$_3$)CO$_2$CH$_3$ | H | H | 140–141 |
| 153. | 4-OCF$_2$CF$_2$H | 4-OCF$_2$CF$_2$H | N(CH$_3$)CO$_2$CH$_3$ | H | H | 155–156 |
| 154. | 4-Cl | 4-CF$_3$ | NHCO$_2$CH$_2$CCl$_3$ | H | H | 121–122 |
| 155. | 4-Cl | 4-CF$_3$ | NH$_2$ | H | H | 144–146 |
| 156. | 4-Cl | 4-CF$_3$ | NHSO$_2$CH$_3$ | H | H | 261–262 |
| 157. | 4-Cl | 4-CF$_3$ | NHCOCH$_2$CH$_3$ | H | H | 256–257 |
| 158. | 4-Cl | 4-CF$_3$ | NHCOCH$_3$ | H | H | 261–262 |
| 159. | 4-Cl | 4-CF$_3$ | NHCO$_2$CH$_2$CH$_3$ | H | H | 214–215 |
| 160. | 4-Cl | 4-CF$_3$ | NHCOCF$_3$ | H | H | 259–260 |
| 161. | 4-Cl | 4-CF$_3$ | NHCHO | H | H | 258–259 |
| 162. | 4-Cl | 4-CF$_3$ | N(CH$_3$)SO$_2$CH$_3$ | H | H | 263–265 |
| 163. | 4-Cl | 4-CF$_3$ | N(CH$_3$)COCF$_3$ | H | H | 215–216 |
| 164. | 4-Cl | 4-CF$_3$ | N(CH$_3$)COCH$_2$CH$_2$CH$_3$ | H | H | 190–192 |
| 165. | 4-Cl | 4-CF$_3$ | N(CH$_3$)COCH(CH$_3$)$_2$ | H | H | 180–182 |
| 166. | 4-Cl | 4-CF$_3$ | N(CH$_3$)PO(OCH$_2$CH$_3$)$_2$ | H | H | 134–136 |
| 167. | 4-Cl | 4-CF$_3$ | N(CH$_3$)PS(OCH$_2$CH$_3$)$_2$ | H | H | 128–132 |
| 168. | 4-Cl | 4-CF$_3$ | N(CH$_3$)CONHCH$_3$ | H | H | 254–256 |
| 169. | 4-Cl | 4-CF$_3$ | N(CH$_3$)$_2$ | H | H | 163–164 |
| 170. | 4-Cl | 4-CF$_3$ | N(CH$_3$)COCH$_2$Cl | H | H | 229–230 |
| 171. | 4-Cl | 4-CF$_3$ | SCH$_3$ | H | H | 185–186 |
| 172. | 4-Cl | 4-CF$_3$ | SO$_2$CH$_3$ | H | H | 238–239 |
| 173. | H | 4-OCF$_3$ | NHCO$_2$CH$_2$CCl$_3$ | H | H | 212–216 |
| 174. | H | 4-OCF$_3$ | NH$_2$ | H | H | 117–119 |
| 175. | H | 4-OCF$_3$ | NHCOCH$_3$ | H | H | 229–230 |
| 176. | H | 4-OCF$_3$ | NHCOCH$_2$CH$_3$ | H | H | 217–219 |
| 177. | H | 4-OCF$_3$ | NHCOCH$_2$CH$_2$CH$_3$ | H | H | 197–198 |
| 178. | H | 4-OCF$_3$ | NHCOCF$_3$ | H | H | 276–278 |
| 179. | H | 4-OCF$_3$ | NHCO$_2$CH$_3$ | H | H | 185–187 |
| 180. | H | 4-OCF$_3$ | NHCO$_2$CH$_2$CH$_3$ | H | H | 186–188 |
| 181. | H | 4-OCF$_3$ | NHCO$_2$CH$_2$CH$_2$CH$_3$ | H | H | 166–168 |
| 182. | H | 4-OCF$_3$ | NHCO$_2$CH(CH$_3$)$_2$ | H | H | 230–235 |
| 183. | H | 4-OCF$_3$ | NHCOSCH$_2$CH$_3$ | H | H | 183–185 |
| 184. | H | 4-OCF$_3$ | NHSO$_2$CH$_3$ | H | H | 216–219 |
| 185. | 4-OCF$_2$H | 4-OCF$_3$ | N(CH$_3$)CO$_2$CH$_2$CCl$_3$ | H | H | 123–125 |
| 186. | 4-OCF$_2$H | 4-OCF$_3$ | NHCH$_3$ | H | H | 96–97 |
| 187. | 4-OCF$_2$H | 4-OCF$_3$ | N(CH$_3$)COCH$_2$CH$_2$CH$_3$ | H | H | 127–128 |
| 188. | 4-OCF$_2$H | 4-OCF$_3$ | N(CH$_3$)COCH$_2$CH$_3$ | H | H | 162–163 |
| 189. | 4-OCF$_2$H | 4-OCF$_3$ | N(CH$_3$)COCH$_3$ | H | H | 135–137 |
| 190. | 4-OCF$_2$H | 4-OCF$_3$ | N(CH$_3$)CO$_2$CH$_2$CH$_3$ | H | H | 130–131 |
| 191. | 4-OCF$_2$H | 4-OCF$_3$ | N(CH$_3$)COSCH$_2$CH$_3$ | H | H | 141–142 |
| 192. | 4-OCF$_2$H | 4-OCF$_3$ | N(CH$_3$)CO$_2$CH(CH$_3$)$_2$ | H | H | 122–123 |
| 193. | 4-OCF$_2$H | 4-OCF$_3$ | N(CH$_3$)CON(CH$_3$)$_2$ | H | H | 140–141 |
| 194. | 4-OCF$_2$H | 4-OCF$_3$ | NHCO$_2$CH$_2$CCl$_3$ | H | H | 169–172 |
| 195. | 4-OCF$_2$H | 4-OCF$_3$ | NH$_2$ | H | H | 112–114 |
| 196. | 4-OCF$_2$H | 4-OCF$_3$ | NHCOCH(CH$_3$)$_2$ | H | H | 217–218 |
| 197. | 4-OCF$_2$H | 4-OCF$_3$ | NHCOCH$_2$CH$_3$ | H | H | 221–222 |
| 198. | 4-OCF$_2$H | 4-OCF$_3$ | NHCOCH$_2$CH$_3$ | H | H | 216–217 |
| 199. | 4-OCF$_2$H | 4-OCF$_3$ | NHCOCF$_3$ | H | H | 203–204 |
| 200. | 4-OCF$_2$H | 4-OCF$_3$ | NHCO$_2$CH$_2$CH$_3$ | H | H | 204–205 |
| 201. | 4-OCF$_2$H | 4-OCF$_3$ | NHCO$_2$CH$_3$ | H | H | 185–187 |
| 202. | 4-OCF$_2$H | 4-OCF$_3$ | NHCOSCH$_2$CH$_3$ | H | H | 194–195 |
| 203. | H | 4-CF$_3$ | NH$_2$ | H | H | 138–139 |
| 204. | 4-OCF$_2$H | 4-OCF$_3$ | NHCO$_2$CH$_2$CHCl$_2$ | H | H | 169–171 |
| 205. | H | 4-CF$_3$ | NHCOCH(CH$_3$)$_2$ | H | H | 226–228 |
| 206. | H | 4-CF$_3$ | NHCOCH$_2$CH$_3$ | H | H | 201–202 |
| 207. | H | 4-CF$_3$ | NHCOCH$_2$CH$_3$ | H | H | 229–230 |
| 208. | H | 4-CF$_3$ | NHCOCF$_3$ | H | H | 147–148 |
| 209. | H | 4-CF$_3$ | NHCO$_2$CH$_2$CH$_3$ | H | H | 188–189 |
| 210. | H | 4-CF$_3$ | NHCOSCH$_2$CH$_3$ | H | H | 169–171 |
| 211. | H | 4-CF$_3$ | NHCO$_2$CH(CH$_3$)$_2$ | H | H | 193–194 |

TABLE I-continued

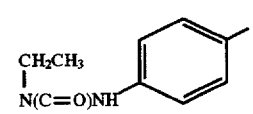

| EX. | Q | G | Y | Z | V | mp °C. |
|---|---|---|---|---|---|---|
| 212. | H | 4-CF$_3$ | NHSO$_2$CH$_3$ | H | H | 209–211 |
| 213. | H | 4-CF$_3$ | NHCO$_2$CH$_2$CCl$_3$ | H | H | 190–193 |
| 214. | 4-OCF$_2$H | 4-OCF$_3$ | N(CH$_2$CH$_3$)CO$_2$CH$_2$CCl$_3$ | H | H | 134–137 |
| 215. | 4-OCF$_2$H | 4-CF$_3$ | N(CH$_2$CH$_3$)CO$_2$CH$_2$CCl$_3$ | H | H | 138–140 |
| 216. | 4-Cl | 4-CF$_3$ | N(CH$_2$CH$_3$)CO$_2$CH$_2$CCl$_3$ | H | H | 181–184 |
| 217. | 4-Cl | 4-OCF$_3$ | N(CH$_2$CH$_3$)CO$_2$CH$_2$CCl$_3$ | H | H | 177–179 |
| 218. | H | 4-CF$_3$ | N(CH$_2$CH$_3$)CO$_2$CH$_2$CCl$_3$ | H | H | 135–137 |
| 219. | H | 4-OCF$_3$ | N(CH$_2$CH$_3$)CO$_2$CH$_2$CCl$_3$ | H | H | 151–152 |
| 220. | 4-OCF$_2$H | 4-OCF$_3$ | NHCH$_2$CH$_3$ | H | H | 97–99 |
| 221. | 4-OCF$_2$H | 4-OCF$_3$ | N(CH$_2$CH$_3$)CO$_2$CH$_3$ | H | H | 167–168 |
| 222. | 4-OCF$_2$H | 4-OCF$_3$ | N(CH$_2$CH$_3$)CO$_2$CH$_2$CH$_3$ | H | H | 139–140 |
| 223. | 4-OCF$_2$H | 4-OCF$_3$ | N(CH$_2$CH$_3$)CO$_2$(CH$_2$)$_2$CH$_3$ | H | H | 142–143 |
| 224. | 4-OCF$_2$H | 4-OCF$_3$ | N(CH$_2$CH$_3$)CO$_2$CH(CH$_3$)$_2$ | H | H | 150–151 |
| 225. | 4-OCF$_2$H | 4-OCF$_3$ | N(CH$_2$CH$_3$)COSCH$_2$CH$_3$ | H | H | 168–169 |
| 226. | 4-OCF$_2$H | 4-OCF$_3$ | N(CH$_2$CH$_3$)COCH$_3$ | H | H | 164–165 |
| 227. | 4-OCF$_2$H | 4-OCF$_3$ | N(CH$_2$CH$_3$)COCH$_2$CH$_3$ | H | H | 179–180 |
| 228. | 4-OCF$_2$H | 4-OCF$_3$ | N(CH$_2$CH$_3$)CO(CH$_2$)$_2$CH$_3$ | H | H | 159–160 |
| 229. | 4-OCF$_2$H | 4-OCF$_3$ | N(CH$_2$CH$_3$)COCH(CH$_3$)$_2$ | H | H | 188–189.5 |
| 230. | 4-OCF$_2$H | 4-OCF$_3$ | N(CH$_2$CH$_3$)COCF$_3$ | H | H | 184–185 |
| 231. | 4-OCF$_2$H | 4-OCF$_3$ | N(CH$_2$CH$_3$)SO$_2$CH$_3$ | H | H | 211–212 |
| 232. | 4-OCF$_2$H | 4-OCF$_3$ | N(CH$_2$CH$_2$)CHO | H | H | 141–142 |
| 233. | 4-OCF$_2$H | 4-OCF$_3$ | $\underset{\underset{\text{N(C=O)NH}}{|}}{\text{CH}_2\text{CH}_3}$—(4-OCF$_3$-phenyl) | H | H | 115–116 d |
| 234. | 4-Cl | 4-CF$_3$ | N(CH$_3$)COC(CH$_3$)$_3$ | H | H | 167–170 |
| 235. | 4-Cl | 4-CF$_3$ | N(CH$_3$)CO$_2$C(CH$_3$)$_3$ | H | H | 153–154 |
| 236. | 4-Cl | 4-CF$_3$ | N(CH$_3$)COCH$_2$OCH$_3$ | H | H | 186–187 |
| 237. | 4-Cl | 4-CF$_3$ | N(CH$_3$)CN | H | H | 216–217 |
| 238. | 4-Cl | 4-CF$_3$ | N(CH$_3$)COCCl$_3$ | H | H | 185–187 |
| 239. | 4-Cl | 4-CF$_3$ | N(CH$_3$)CO$_2$CH$_2$CH(CH$_3$)$_2$ | H | H | 157–159 |
| 240. | 4-Cl | 4-CF$_3$ | N(CH$_3$)COCH=CH$_2$ | H | H | 182–183 |
| 241. | 4-Cl | 4-CF$_3$ | N(CH$_3$)COCCH$_3$'CH$_2$ | H | H | 174–176 |
| 242. | 4-Cl | 4-CF$_3$ | N(CH$_3$)COCH∝CHCH$_3$ | H | H | 192–194 |
| 243. | 4-Cl | 4-CF$_3$ | N(CH$_3$)COCH=C(CH$_3$)$_2$ | H | H | 168–170 |
| 244. | 4-Cl | 4-CF$_3$ | N(CH$_3$)COCF$_2$CF$_3$ | H | H | 193–195 |
| 245. | 4-Cl | 4-CF$_3$ | N(CH$_3$)COCF$_2$CF$_2$CF$_3$ | H | H | 210–211 |
| 246. | 4-Cl | 4-CF$_3$ | N(CH$_3$)COC(Cl)=CCl$_2$ | H | H | 171–175 |
| 247. | H | 4-CF$_3$ | NHCH$_3$ | H | H | 144–146 |
| 248. | H | 4-CF$_3$ | N(CH$_3$)CO$_2$CH$_2$CH$_3$ | H | H | 145–146 |
| 249. | H | 4-CF$_3$ | N(CH$_3$)CO$_2$CH$_2$CH$_2$CH$_3$ | H | H | 126–128 |
| 250. | H | 4-CF$_3$ | N(CH$_3$)CO$_2$CH(CH$_3$)$_2$ | H | H | 135–136 |
| 251. | H | 4-CF$_3$ | N(CH$_3$)COSCH$_2$CH$_3$ | H | H | 169–171 |
| 252. | H | 4-CF$_3$ | N(CH$_3$)COCH$_3$ | H | H | 207–208 |
| 253. | H | 4-CF$_3$ | N(CH$_3$)COCH$_2$CH$_3$ | H | H | 200–202 |
| 254. | H | 4-CF$_3$ | N(CH$_3$)COCH$_2$CH$_2$CH$_3$ | H | H | 171–173 |
| 255. | H | 4-CF$_3$ | N(CH$_3$)COCH(CH$_3$)$_2$ | H | H | 176–178 |
| 256. | H | 4-CF$_3$ | N(CH$_3$)COCF$_3$ | H | H | 193–194 |
| 257. | H | 4-CF$_3$ | N(CH$_3$)SO$_2$CH$_3$ | H | H | 232–233 |
| 258. | H | 4-CF$_3$ | N(CH$_3$)COCF$_2$CF$_3$ | H | H | 188–189 |
| 259. | H | 4-CF$_3$ | N(CH$_3$)CHO | H | H | 198–199 |
| 260. | 4-OCF$_2$H | 4-CF$_3$ | NHC$_2$H$_5$ | H | H | 127–129 |
| 261. | 4-OCF$_2$H | 4-CF$_3$ | N(C$_2$H$_5$)CO$_2$CH$_3$ | H | H | 173–174 |
| 262. | 4-OCF$_2$H | 4-CF$_3$ | N(C$_2$H$_5$)CO$_2$C$_2$H$_5$ | H | H | 130–132 |
| 263. | 4-OCF$_2$H | 4-CF$_3$ | N(C$_2$H$_5$)CO$_2$CH$_2$CH$_2$CH$_3$ | H | H | 107–110 |
| 264. | 4-OCF$_2$H | 4-CF$_3$ | N(C$_2$H$_5$)CO$_2$CH(CH$_3$)$_2$ | H | H | 147–148 |
| 265. | 4-OCF$_2$H | 4-CF$_3$ | N(C$_2$H$_5$)COSC$_2$H$_5$ | H | H | 177–178 |
| 266. | 4-OCF$_2$H | 4-CF$_3$ | N(C$_2$H$_5$)COCH$_3$ | H | H | 149–151 |
| 267. | 4-OCF$_2$H | 4-CF$_3$ | N(C$_2$H$_5$)COC$_2$H$_5$ | H | H | 166–167 |
| 268. | 4-OCF$_2$H | 4-CF$_3$ | N(C$_2$H$_5$)COCH$_2$CH$_2$CH$_3$ | H | H | 155–156 |
| 269. | 4-OCF$_2$H | 4-CF$_3$ | N(C$_2$H$_5$)COCH(CH$_3$)$_2$ | H | H | 182–183 |
| 270. | 4-OCF$_2$H | 4-CF$_3$ | N(C$_2$H$_5$)COCF$_3$ | H | H | 181–183 |
| 271. | 4-OCF$_2$H | 4-CF$_3$ | N(C$_2$H$_5$)SO$_2$CH$_3$ | H | H | 218–220 |
| 272. | 4-OCF$_2$H | 4-CF$_3$ | N(C$_2$H$_5$)COCF$_2$CF$_3$ | H | H | 205–206 |
| 273. | 4-OCF$_2$H | 4-CF$_3$ | N(C$_2$H$_5$)CHO | H | H | 140–142 |

TABLE I-continued

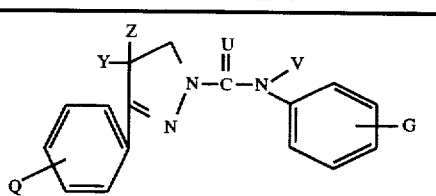

| EX. | Q | G | Y | Z | V | mp °C. |
|---|---|---|---|---|---|---|
| 274. | 4-OCF$_2$H | 4-CF$_3$ | N(C$_2$H$_5$)COC(CH$_3$)$_3$ | H | H | 220–222 |
| 275. | 4-Cl | 4-OCF$_3$ | NHCH$_3$ | H | H | 140–141 |
| 276. | 4-Cl | 4-OCF$_3$ | N(CH$_3$)CO$_2$CH$_3$ | H | H | 158–159 |
| 277. | 4-Cl | 4-OCF$_3$ | N(CH$_3$)CO$_2$C$_2$H$_5$ | H | H | 165–166 |
| 278. | 4-Cl | 4-OCF$_3$ | N(CH$_3$)CO$_2$CH$_2$CH$_2$CH$_3$ | H | H | 146–147 |
| 279. | 4-Cl | 4-OCF$_3$ | N(CH$_3$)CO$_2$CH(CH$_3$)$_2$ | H | H | 162–163 |
| 280. | 4-Cl | 4-OCF$_3$ | N(CH$_3$)COSC$_2$H$_5$ | H | H | 184–185 |
| 281. | 4-Cl | 4-OCF$_3$ | N(CH$_3$)COCH$_3$ | H | H | 198–199 |
| 282. | 4-Cl | 4-OCF$_3$ | N(CH$_3$)COC$_2$H$_5$ | H | H | 197–198 |
| 283. | 4-Cl | 4-OCF$_3$ | N(CH$_3$)COCH$_2$CH$_2$CH$_3$ | H | H | 166–167 |
| 284. | 4-Cl | 4-OCF$_3$ | N(CH$_3$)COCH(CH$_3$)$_2$ | H | H | 188–189 |
| 285. | 4-Cl | 4-OCF$_3$ | N(CH$_3$)COCF$_3$ | H | H | 213–214 |
| 286. | 4-Cl | 4-OCF$_3$ | N(CH$_3$)COCF$_2$CF$_3$ | H | H | 217–218 |
| 288. | 4-Cl | 4-OCF$_3$ | N(CH$_3$)COC(CH$_3$)=CH$_2$ | H | H | 184–185 |
| 289. | 4-Cl | 4-OCF$_3$ | N(CH$_3$)CHO | H | H | 175–176 |
| 290. | 4-Cl | 4-OCF$_3$ | N(CH$_3$)CO$_2$CH$_2$CCl$_3$ | H | H | 165–168 |
| 291. | 4-Cl | 4-CF$_3$ | N(CH$_3$)COSC$_2$H$_5$ | H | H | 179–181 |
| 292. | 4-Cl | 4-CF$_3$ | N(CH$_3$)CO$_2$CH$_2$C|CH | H | H | 152–155 |
| 293. | 4-Cl | 4-CF$_3$ | N(CH$_3$)CO$_2$CH$_2$CH=CH$_2$ | H | H | 62–65 |
| 294. | 4-Cl | 4-CF$_3$ | N(CH$_3$)COCH$_2$C$_6$H$_5$ | H | H | 178–180 |
| 295. | 4-Cl | 4-CF$_3$ | N(CH$_3$)CO$_2$C$_6$H$_5$ | H | H | 183–185 |
| 296. | 4-Cl | 4-CF$_3$ | N(CH$_3$)CO$_2$CH$_2$CH$_2$Cl | H | H | 122–124 |
| 297. | 4-OH | 4-OCF$_3$ | N(CH$_3$)CO$_2$CH$_3$ | H | H | 228–133 |
| 298. | 4-OC$_2$H$_5$ | 4-OCF$_3$ | N(CH$_3$)CO$_2$CH$_3$ | H | H | 157–159 |
| 299. | 4-OCH$_2$CH$_2$CH$_3$ | 4-OCF$_3$ | N(CH$_3$)CO$_2$CH$_3$ | H | H | 153–155 |
| 300. | 4-O(CH$_2$)$_3$CH$_3$ | 4-OCF$_3$ | N(CH$_3$)CO$_2$CH$_3$ | H | H | 128–133 |
| 301. | 4-Cl | 4-CF$_3$ | N(CH(CH$_3$)$_2$)CO$_2$CH$_2$CCl$_3$ | H | H | 188–189 |
| 302. | 4-Cl | 4-CF$_3$ | NHC$_2$H$_5$ | H | H | 148–150 |
| 303. | 4-Cl | 4-CF$_3$ | NH(CH(CH$_3$)$_2$) | H | H | 125–127 |
| 304. | 4-Cl | 4-CF$_3$ | N(CH(CH$_3$)$_2$)COCH$_3$ | H | H | 257–258 |
| 305. | 4-Cl | 4-CF$_3$ | N(C$_2$H$_5$)CO$_2$C$_2$H$_5$ | H | H | 160–162 |
| 306. | 4-Cl | 4-CF$_3$ | N(C$_2$H$_5$)CO$_2$CH$_2$CH$_2$CH$_3$ | H | H | 183–184 |
| 307. | 4-Cl | 4-CF$_3$ | N(C$_2$H$_5$)CO$_2$CH(CH$_3$)$_2$ | H | H | 154–155 |
| 308. | 4-Cl | 4-CF$_3$ | N(C$_2$H$_5$)COCH$_3$ | H | H | 184–185 |
| 309. | 4-Cl | 4-CF$_3$ | N(C$_2$H$_5$)COC$_2$H$_5$ | H | H | 211–212 |
| 310. | 4-Cl | 4-CF$_3$ | N(C$_2$H$_5$)COCH$_2$CH$_2$CH$_3$ | H | H | 184–185 |
| 311. | 4-Cl | 4-CF$_3$ | N(C$_2$H$_5$)COCH(CH$_3$)$_2$ | H | H | 224–225 |
| 312. | 4-Cl | 4-CF$_3$ | N(C$_2$H$_5$)COCF$_3$ | H | H | 212–213 |
| 313. | 4-Cl | 4-CF$_3$ | N(C$_2$H$_5$)COCF$_2$CF$_3$ | H | H | 214–215 |
| 314. | 4-Cl | 4-CF$_3$ | N(C$_2$H$_5$)SO$_2$CH$_3$ | H | H | 230–232 |
| 315. | 4-Cl | 4-CF$_3$ | N(C$_2$H$_5$)CHO | H | H | 143–145 |
| 316. | 4-Cl | 4-CF$_3$ | N(CH(CH$_3$)$_2$)CHO | H | H | 219–220 |
| 317. | 4-Cl | 4-CF$_3$ | N(CH(CH$_3$)$_2$)COCF$_3$ | H | H | 250–251 |
| 318. | 4-Cl | 4-CF$_3$ | N(CH(CH$_3$)$_2$)COC$_2$H$_5$ | H | H | 246–247 |
| 319. | 4-Cl | 4-OCF$_2$CFClH | N(CH$_3$)CO$_2$CH$_3$ | H | H | 188–190 |
| 320. | 4-Cl | 4-OCF$_2$CF$_2$H | N(CH$_3$)CO$_2$CH$_2$CCl$_3$ | H | H | 190–193 |
| 321. | 4-Cl | 4-OCF$_2$CF$_2$H | N(C$_2$H$_5$)CO$_2$CH$_2$CCl$_3$ | H | H | 203–204 |
| 322. | 4-Cl | 4-CF$_3$ | N(CH$_3$)SO$_2$C$_2$H$_5$ | H | H | 263–264 |
| 323. | 4-Cl | 4-CF$_3$ | N(CH$_3$)SO$_2$C$_6$H$_5$ | H | H | 210–211 |
| 324. | 4-Cl | 4-CF$_3$ | N(CH$_3$)SO$_2$C$_6$H$_4$-4-Cl | H | H | 247–248 |
| 325. | 4-Cl | 4-OCF$_3$ | NH(C$_2$H$_5$) | H | H | 116–118 |
| 326. | 4-Cl | 4-OCF$_3$ | N(C$_2$H$_5$)CO$_2$C$_2$H$_5$ | H | H | 164–166 |
| 327. | 4-Cl | 4-OCF$_3$ | N(C$_2$H$_5$)COCH$_3$ | H | H | 194–195 |
| 328. | 4-Cl | 4-OCF$_3$ | N(C$_2$H$_5$)COC$_2$H$_5$ | H | H | 200–201.5 |
| 329. | 4-Cl | 4-OCF$_3$ | N(C$_2$H$_5$)COCF$_3$ | H | H | 212–213 |
| 330. | 4-Cl | 4-OCF$_3$ | N(C$_2$H$_5$)CO$_2$CH$_2$CH$_2$CH$_3$ | H | H | 154–155.5 |
| 331. | 4-Cl | 4-OCF$_3$ | N(C$_2$H$_5$)CO$_2$CH(CH$_3$)$_2$ | H | H | 193–194 |
| 332. | 4-Cl | 4-OCF$_3$ | N(C$_2$H$_5$)COCH$_2$CH$_2$CH$_3$ | H | H | 198–199 |
| 333. | 4-Cl | 4-OCF$_3$ | N(C$_2$H$_5$)COCH(CH$_3$)$_2$ | H | H | 226–277 |
| 334. | 4-Cl | 4-OCF$_3$ | N(C$_2$H$_5$)SO$_2$CH$_3$ | H | H | 203–204 |
| 335. | 4-Cl | 4-OCF$_3$ | N(C$_2$H$_5$)CSOC$_2$H$_5$ | H | H | 198–199 |
| 336. | 4-Cl | 4-OCF$_3$ | N(C$_2$H$_5$)CHO | H | H | 188–189 |
| 337. | 4-Cl | 4-OCF$_3$ | N(C$_2$H$_5$)CO$_2$CH$_3$ | H | H | 172–173 |
| 338. | 4-Br | 4-CF$_3$ | N(C$_2$H$_5$)CO$_2$CH$_3$ | H | H | 164–165 |
| 339. | 4-Br | 4-OCF$_3$ | N(C$_2$H$_5$)CO$_2$CH$_3$ | H | H | 169–171 |
| 340. | 4-Br | 4-OCF$_2$CF$_2$H | N(C$_2$H$_5$)CO$_2$CH$_3$ | H | H | 193–194 |
| 341. | 4-Br | 4-Cl | N(C$_2$H$_5$)CO$_2$CH$_3$ | H | H | 140–142 |

TABLE I-continued

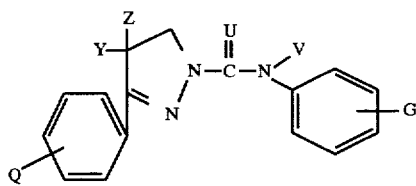

| EX. | Q | G | Y | Z | V | mp °C. |
|---|---|---|---|---|---|---|
| 342. | 4-Cl | 4-OCF$_2$Br | N(C$_2$H$_5$)CO$_2$CH$_3$ | H | H | 172–174 |
| 343. | 4-Cl | 4-F | N(C$_2$H$_5$)CO$_2$CH$_3$ | H | H | 152–154 |
| 344. | 4-Cl | 4-NO$_2$ | N(C$_2$H$_5$)CO$_2$CH$_3$ | H | H | 196–198 |
| 345. | 4-F | 4-CF$_3$ | N(C$_2$H$_5$)CO$_2$CH$_3$ | H | H | 162–164 |
| 346. | 4-F | 4-OCF$_3$ | N(C$_2$H$_5$)CO$_2$CH$_3$ | H | H | 120–122 |
| 347. | 4-F | 4-OCF$_2$CF$_2$H | N(C$_2$H$_5$)CO$_2$CH$_3$ | H | H | 153–155 |
| 348. | 4-F | 4-Cl | N(C$_2$H$_5$)CO$_2$CH$_3$ | H | H | 158–160 |
| 349. | 4-Cl | 4-CF$_3$ | N(CH$_2$CH$_2$CH$_3$)CO$_2$CH$_2$CCl$_3$ | H | H | 172–173 |
| 350. | 4-Cl | 4-OCF$_3$ | N(CH$_2$CH$_2$CH$_3$)CO$_2$CH$_2$CCl$_3$ | H | H | 178–180 |
| 351. | 4-Cl | 4-OCF$_2$CF$_2$H | NHCH$_3$ | H | H | 154–155 |
| 352. | 4-Cl | 4-OCF$_2$CF$_2$H | N(CH$_3$)CO$_2$CH$_2$CH$_3$ | H | H | 198–199 |
| 353. | 4-Cl | 4-OCF$_2$CF$_2$H | N(CH$_3$)CO$_2$CH(CH$_3$)$_2$ | H | H | 198–199 |
| 354. | 4-Cl | 4-OCF$_2$CF$_2$H | N(CH$_3$)CO$_2$CH$_2$CH$_2$CH$_3$ | H | H | 139–141 |
| 355. | 4-Cl | 4-OCF$_2$CF$_2$H | N(CH$_3$)CHO | H | H | 178.5–180 |
| 356. | 4-Cl | 4-OCF$_2$CF$_2$H | N(CH$_3$)COCH$_3$ | H | H | 211–213 |
| 357. | 4-Cl | 4-OCF$_2$CF$_2$H | N(CH$_3$)COCH$_2$CH$_3$ | H | H | 210–212 |
| 358. | 4-Cl | 4-OCF$_2$CF$_2$H | N(CH$_3$)COCH(CH$_3$)$_2$ | H | H | 225–227 |
| 359. | 4-Cl | 4-OCF$_2$CF$_2$H | N(CH$_3$)COCH$_2$CH$_2$CH$_3$ | H | H | 196–197 |
| 360. | 4-Cl | 4-OCF$_2$CF$_2$H | N(CH$_3$)COCF$_3$ | H | H | 242–243 |
| 361. | 4-Cl | 4-OCF$_2$CF$_2$H | N(CH$_3$)SO$_2$CH$_3$ | H | H | 239–241 |
| 362. | 3-Cl | 4-CF$_3$ | N(CH$_3$)CO$_2$CH$_3$ | H | H | 163–164 |
| 363. | 3-Cl | 4-OCF$_3$ | N(CH$_3$)CO$_2$CH$_3$ | H | H | 139–140 |
| 364. | 3-Cl | 4-OCF$_2$CF$_2$H | N(CH$_3$)CO$_2$CH$_3$ | H | H | 157–158 |
| 365. | 3-Cl | 4-Cl | N(CH$_3$)CO$_2$CH$_3$ | H | H | 139–141 |
| 366. | 4-Cl | 4-CF$_3$ | N(CH$_2$CH$_3$)CO(CH$_2$)$_3$CH$_3$ | H | H | 178–179 |
| 367. | 4-Cl | 4-CF$_3$ | N(CH$_2$CH$_3$)COCH(CH$_3$)CH$_2$CH$_3$ | H | H | 218–219 |
| 368. | 4-Cl | 4-CF$_3$ | N(CH$_2$CH$_3$)COCH$_2$CH(CH$_3$)$_2$ | H | H | 183–184.5 |
| 369. | 4-Cl | 4-CF$_3$ | N(CH$_2$CH$_3$)CO(CH$_2$)$_4$CH$_3$ | H | H | 168.5–170 |
| 370. | 4-Cl | 4-CF$_3$ | N((CH$_2$)$_3$CH$_3$)CO$_2$CH$_2$Cl$_3$ | H | H | 175–178 |
| 371. | 2-Cl | 4-CF$_3$ | N(CH$_3$)CO$_2$CH$_3$ | H | H | 140–141 |
| 372. | 2-Cl | 4-OCF$_3$ | N(CH$_3$)CO$_2$CH$_3$ | H | H | 102–104 |
| 373. | 2-Cl | 4-OCF$_2$CF$_2$H | N(CH$_3$)CO$_2$CH$_3$ | H | H | 130–132 |
| 374. | 2-Cl | 4-Cl | N(CH$_3$)CO$_2$CH$_3$ | H | H | 126–128 |
| 375. | 4-Cl | 4-OCF$_3$ | N(CH$_3$)CO(CH$_2$)$_3$CH$_3$ | H | H | 160–162 |
| 376. | 4-Cl | 4-OCF$_3$ | N(CH$_3$)COCH(CH$_3$)CH$_2$CH$_3$ | H | H | 170–172 |
| 377. | 4-Cl | 4-OCF$_3$ | N(CH$_3$)COCH$_2$CH(CH$_3$)$_2$ | H | H | 176–178 |
| 378. | 4-Cl | 4-OCF$_3$ | N(CH$_3$)CO(CH$_2$)$_4$CH$_3$ | H | H | 143–144 |
| 379. | 4-OCH$_2$CH$_2$CH$_3$ | 4-CF$_3$ | N(CH$_3$)CO$_2$CH$_3$ | H | H | 158–160 |
| 380. | 4-Cl | 4-OCF$_2$CF$_2$H | NHCH$_2$CH$_3$ | H | H | 118–122 |
| 381. | 4-Cl | 4-OCF$_2$CF$_2$H | N(CH$_2$CH$_3$)CO$_2$CH$_2$CH$_3$ | H | H | 175–176 |
| 382. | 4-Cl | 4-OCF$_2$CF$_2$H | N(CH$_2$CH$_3$)CO$_2$CH(CH$_3$)$_2$ | H | H | 206–207 |
| 383. | 4-Cl | 4-OCF$_2$CF$_2$H | N(CH$_2$CH$_3$)CO$_2$CH$_2$CH$_2$CH$_3$ | H | H | 184–185 |
| 384. | 4-Cl | 4-OCF$_2$CF$_2$H | N(CH$_2$CH$_3$)CHO | H | H | 182–183 |
| 385. | 4-Cl | 4-OCF$_2$CF$_2$H | N(CH$_2$CH$_3$)COCH$_3$ | H | H | 207–208 |
| 386. | 4-Cl | 4-OCF$_2$CF$_2$H | N(CH$_2$CH$_3$)COCH$_2$CH$_3$ | H | H | 203–204 |
| 387. | 4-Cl | 4-OCF$_2$CF$_2$H | N(CH$_2$CH$_3$)COCH(CH$_3$)$_2$ | H | H | 222–223 |
| 388. | 4-Cl | 4-OCF$_2$CF$_2$H | N(CH$_2$CH$_3$)COCH$_2$CH$_2$CH$_3$ | H | H | 202–203 |
| 389. | 4-Cl | 4-OCF$_2$CF$_2$H | N(CH$_2$CH$_3$)COCF$_3$ | H | H | 224–225 |
| 390. | 4-Cl | 4-OCF$_2$CF$_2$H | N(CH$_2$CH$_3$)SO$_2$CH$_3$ | H | H | 219–221 |
| 391. | 4-CH$_2$CH$_2$CH$_3$ | 4-CF$_3$ | N(CH$_3$)CO$_2$CH$_3$ | H | H | 125–127 |
| 392. | 4-CH$_2$CH$_2$CH$_3$ | 4-OCF$_3$ | N(CH$_3$)CO$_2$CH$_3$ | H | H | 126–128 |
| 393. | 4-CH$_2$CH$_2$CH$_3$ | 4-OCF$_2$CF$_2$H | N(CH$_3$)CO$_2$CH$_3$ | H | H | 124–126 |
| 394. | 4-CH$_2$CH$_2$CH$_3$ | 4-Cl | N(CH$_3$)CO$_2$CH$_3$ | H | H | 127–129 |
| 395. | 4-OCH$_2$CH$_2$OCH$_3$ | 4-OCF$_3$ | N(CH$_3$)CO$_2$CH$_3$ | H | H | 113–114 |
| 396. | 4-Cl,3-CH$_3$ | 4-CF$_3$ | N(CH$_3$)CO$_2$CH$_3$ | H | H | 189–191 |
| 397. | 4-Cl,3-CH$_3$ | 4-OCF$_3$ | N(CH$_3$)CO$_2$CH$_3$ | H | H | 164–166 |
| 398. | 4-Cl,3-CH$_3$ | 4-OCF$_2$CF$_2$H | N(CH$_3$)CO$_2$CH$_3$ | H | H | 171–173 |
| 399. | 4-Cl,3-CH$_3$ | 4-Cl | N(CH$_3$)CO$_2$CH$_3$ | H | H | 159–160 |
| 400. | 4-OCH$_3$ | 4-OCF$_3$ | N(CH$_3$)CO$_2$CH$_3$ | H | H | 165–166 |
| 401. | 4-Cl,3-Cl | 4-CF$_3$ | N(CH$_3$)CO$_2$CH$_3$ | H | H | 200–203 |
| 402. | 4-Cl,3-Cl | 4-OCF$_3$ | N(CH$_3$)CO$_2$CH$_3$ | H | H | 138–140 |
| 403. | 4-Cl,3-Cl | 4-OCF$_2$CF$_2$H | N(CH$_3$)CO$_2$CH$_3$ | H | H | 160–164 |
| 404. | 4-Cl,3-Cl | 4-Cl | N(CH$_3$)CO$_2$CH$_3$ | H | H | 175–178 |
| 405. | 4-(CH$_2$)$_3$CH$_3$ | 4-CF$_3$ | N(CH$_3$)CO$_2$CH$_3$ | H | H | 118–120 |
| 406. | 4-(CH$_2$)$_3$CH$_3$ | 4-OCF$_3$ | N(CH$_3$)CO$_2$CH$_3$ | H | H | 115–117 |
| 407. | 4-(CH$_2$)$_3$CH$_3$ | 4-OCF$_2$CF$_2$H | N(CH$_3$)CO$_2$CH$_3$ | H | H | 155–157 |
| 408. | 4-(CH$_2$)$_3$CH$_3$ | 4-Cl | N(CH$_3$)CO$_2$CH$_3$ | H | H | oil |

TABLE I-continued

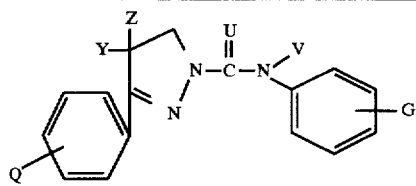

| EX. | Q | G | Y | Z | V | mp °C. |
|---|---|---|---|---|---|---|
| 409. | 4-Cl | 4-CN | N(CH₃)CO₂CH₃ | H | H | 186–188 |
| 410. | 4-Cl | 4-Br | N(CH₃)CO₂CH₃ | H | H | 120–122 |
| 411. | 4-CH₃ | 4-CF₃ | N(CH₃)CO₂CH₃ | H | H | 198–200 |
| 412. | 4-CH₃ | 4-OCF₃ | N(CH₃)CO₂CH₃ | H | H | 157–159 |
| 413. | 4-CH₃ | 4-OCF₂CF₂H | N(CH₃)CO₂CH₃ | H | H | 170–172 |
| 414. | 4-CH₃ | 4-Cl | N(CH₃)CO₂CH₃ | H | H | 171–173 |
| 415. | 4-OCH₂CH₂CH₃ | 4-F | N(CH₃)CO₂CH₃ | H | H | 152–154 |
| 416. | 4-OCH₂CH₂CH₃ | 4-Cl | N(CH₃)CO₂CH₃ | H | H | 147–148.5 |
| 417. | 4-OCH₂CH₂CH₃ | 4-Br | N(CH₃)CO₂CH₃ | H | H | 169–171 |
| 418. | 4-OCH₂CH₂CH₃ | 4-OCF₂CF₂H | N(CH₃)CO₂CH₃ | H | H | 149–151 |
| 419. | 4-Cl | 4-CF₃ | NHCH₂CH₃ | H | H | 172–173 |
| 420. | 4-Cl | 4-CF₃ | N(CH₂CH₂CH₃)CO₂CH₂CH₃ | H | H | 167–168 |
| 421. | 4-Cl | 4-CF₃ | N(CH₂CH₂CH₃)CO₂CH(CH₃)₂ | H | H | 176–178 |
| 422. | 4-Cl | 4-CF₃ | N(CH₂CH₂CH₃)CO₂(CH₂)₂CH₃ | H | H | 156–158 |
| 423. | 4-Cl | 4-CF₃ | N(CH₂CH₂CH₃)CHO | H | H | 195–196 |
| 424. | 4-Cl | 4-CF₃ | N(CH₂CH₂CH₃)COCH₃ | H | H | 201–202 |
| 425. | 4-Cl | 4-CF₃ | N(CH₂CH₂CH₃)COCH₂CH₃ | H | H | 200–201 |
| 426. | 4-Cl | 4-CF₃ | N(CH₂CH₂CH₃)COCH(CH₃)₂ | H | H | 219–220 |
| 427. | 4-Cl | 4-CF₃ | N(CH₂CH₂CH₃)CO(CH₂)₂CH₃ | H | H | 184–185 |
| 428. | 4-Cl | 4-CF₃ | N(CH₂CH₂CH₃)COCF₃ | H | H | 225–226 |
| 429. | 4-Cl | 4-CF₃ | N(CH₂CH₂CH₃)SO₂CH₃ | H | H | 231–233 |
| 430. | 4-OCH₂CH₂CH₃ | 4-CF₃ | N(CH₃)COCF₃ | H | H | 190–191 |
| 431. | 4-OCF₂H | 4-CF₃ | N(CH₃)CO₂C(CH₃)₃ | H | H | 133–135 |
| 432. | 4-OH | 4-CF₃ | N(CH₃)CO₂C(CH₃)₃ | H | H | 211–216 |
| 433. | 4-OCH₂CH₂CH₃ | 4-CF₃ | N(CH₃)CO₂C(CH₃)₃ | H | H | 140–141 |
| 434. | 4-OCH₂CH₂CH₃ | 4-CF₃ | NHCH₃ | H | H | 114–117 |
| 435. | 4-OCH₂CH₂CH₃ | 4-CF₃ | N(CH₃)CO₂CH₂CH₃ | H | H | 117–120 |
| 436. | 4-OCH₂CH₂CH₃ | 4-CF₃ | N(CH₃)COCH₃ | H | H | 145–147 |
| 437. | 4-OCH₂CH₂CH₃ | 4-CF₃ | N(CH₃)COCH₂CH₃ | H | H | 114–116 |
| 440. | 3-OCH₂CH₂CH₃ | 4-CF₃ | N(CH₃)CO₂CH₃ | H | H | 142–144 |
| 441. | 3-OCH₂CH₂CH₃ | 4-OCF₃ | N(CH₃)CO₂CH₃ | H | H | 155–157 |
| 442. | 3-OCH₂CH₂CH₃ | 4-OCF₂CF₂H | N(CH₃)CO₂CH₃ | H | H | 162–164 |
| 443. | 3-OCH₂CH₂CH₃ | 4-Cl | N(CH₃)CO₂CH₃ | H | H | 142–144 |
| 444. | 4-Cl,2-Cl | 4-CF₃ | N(CH₃)CO₂CH₃ | H | H | 122–124 |
| 445. | 4-Cl,2-Cl | 4-OCF₃ | N(CH₃)CO₂CH₃ | H | H | 118–120 |
| 446. | 4-Cl,2-Cl | 4-OCF₂CF₂H | N(CH₃)CO₂CH₃ | H | H | 127–129 |
| 447. | 4-Cl,2-Cl | 4-Cl | N(CH₃)CO₂CH₃ | H | H | 148–150 |
| 448. | 4-Cl | 4-OCF₃ | NHCH₂CH₃ | H | H | 140–141 |
| 449. | 4-Cl | 4-OCF₃ | N(CH₂CH₂CH₃)CO₂CH₂CH₃ | H | H | 154–155 |
| 450. | 4-Cl | 4-OCF₃ | N(CH₂CH₂CH₃)CO₂CH(CH₃)₂ | H | H | 177–178 |
| 451. | 4-Cl | 4-OCF₃ | N(CH₂CH₂CH₃)CHO | H | H | 218–219 |
| 452. | 4-Cl | 4-OCF₃ | N(CH₂CH₂CH₃)COCH₃ | H | H | 205–206 |
| 453. | 4-Cl | 4-OCF₃ | N(CH₂CH₂CH₃)COCH₂CH₃ | H | H | 182–183 |
| 454. | 4-Cl | 4-OCF₃ | N(CH₂CH₂CH₃)COCH(CH₃)₂ | H | H | 201–202 |
| 455. | 4-Cl | 4-OCF₃ | N(CH₂CH₂CH₃)COCH₂CH₂CH₃ | H | H | 179–180 |
| 456. | 4-Cl | 4-OCF₃ | N(CH₂CH₂CH₃)COCF₃ | H | H | 149–150 |
| 457. | 4-CH₂CH₃ | 4-CF₃ | N(CH₃)CO₂CH₃ | H | H | 143–145 |
| 458. | 4-CH₂CH₃ | 4-OCF₃ | N(CH₃)CO₂CH₃ | H | H | 115–117 |
| 459. | 4-CH₂CH₃ | 4-OCF₂CF₂H | N(CH₃)CO₂CH₃ | H | H | 126–127 |
| 460. | 4-CH₂CH₃ | 4-Cl | N(CH₃)CO₂CH₃ | H | H | oil |
| 461. | 4-Cl | 4-CF₃ | NH(CH₂)₃CH₃ | H | H | 131–133 |
| 462. | 4-Cl | 4-CF₃ | N((CH₂)₃CH₃)CO₂CH₃ | H | H | 177–180 |
| 463. | 4-Cl | 4-CF₃ | N((CH₂)₃CH₃)CO₂CH₂CH₃ | H | H | 140–142 |
| 464. | 4-Cl | 4-CF₃ | N((CH₂)₃CH₃)CO₂CH(CH₃)₂ | H | H | 205–207 |
| 465. | 4-Cl | 4-CF₃ | N((CH₂)₃CH₃)CHO | H | H | 181–182 |
| 466. | 4-Cl | 4-CF₃ | N((CH₂)₃CH₃)COCH₃ | H | H | 182–183 |
| 467. | 4-Cl | 4-CF₃ | N((CH₂)₃CH₃)COCH₂CH₃ | H | H | 168–169 |
| 468. | 4-Cl | 4-CF₃ | N((CH₂)₃CH₃)COCH(CH₃)₂ | H | H | 186–187 |
| 469. | 4-Cl | 4-CF₃ | N((CH₂)₃CH₃)COCH₂CH₂CH₃ | H | H | 154–155 |
| 470. | 4-Cl | 4-CF₃ | N((CH₂)₃CH₃)COCF₃ | H | H | 183–184 |
| 471. | 4-OCH₂CH₂CH₃ | 4-OCF₃ | N(CH₃)CO₂CH₂CCl₃ | H | H | 114–116 |
| 472. | 4-OCH₂CH₂CH₃ | 4-OCF₃ | NHCH₃ | H | H | 110–111 |
| 473. | 4-OCH₂CH₂CH₃ | 4-OCF₃ | N(CH₃)CO₂CH₂CH₃ | H | H | 115–117 |
| 474. | 4-OCH₂CH₂CH₃ | 4-OCF₃ | N(CH₃)COCH₃ | H | H | 105–106 |
| 475. | 4-OCH₂CH₂CH₃ | 4-OCF₃ | N(CH₃)COCH₂CH₃ | H | H | 139–140 |
| 476. | 4-OCH₂CH₂CH₃ | 4-OCF₃ | N(CH₃)COCF₃ | H | H | 177–178 |
| 477. | 4-OCH₂CH₂CH₃ | 4-OCF₂CF₂H | N(CH₃)CO₂CH₂CCl₃ | H | H | 119–120 |

TABLE I-continued

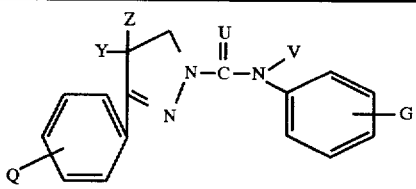

| EX. | Q | G | Y | Z | V | mp °C. |
|---|---|---|---|---|---|---|
| 478. | 4-OCH$_2$CH$_2$CH$_3$ | 4-OCF$_2$CF$_2$H | N(CH$_3$)H | H | H | 104–105 |
| 479. | 4-OCH$_2$CH$_2$CH$_3$ | 4-OCF$_2$CF$_2$H | N(CH$_3$)CO$_2$CH$_2$CH$_3$ | H | H | 126–127 |
| 480. | 4-OCH$_2$CH$_2$CH$_3$ | 4-OCF$_2$CF$_2$H | N(CH$_3$)COCH$_3$ | H | H | 130–132 |
| 481. | 4-OCH$_2$CH$_2$CH$_3$ | 4-OCF$_2$CF$_2$H | N(CH$_3$)COCH$_2$CH$_3$ | H | H | 150–152 |
| 482. | 4-OCH$_2$CH$_2$CH$_3$ | 4-OCF$_2$CF$_2$H | N(CH$_3$)COCF$_3$ | H | H | 195–196 |
| 483. | 4-OCH$_2$CH$_2$CH$_3$ | 4-CF$_3$ | N(CH$_3$)CHO | H | H | 136–138 |
| 484. | 4-OCH$_2$CH$_2$CH$_3$ | 4-OCF$_3$ | N(CH$_3$)CHO | H | H | 130–132 |
| 485. | 4-OCH$_2$CH$_2$CH$_3$ | 4-OCF$_2$CF$_2$H | N(CH$_3$)CHO | H | H | 150–151 |
| 486. | 4-Cl | 4-CF$_3$ | N(CH$_2$CO$_2$CH$_3$)CO$_2$CH$_3$ | H | H | 198–200 |
| 487. | 4-Cl | 4-OCF$_3$ | N(CH$_2$CO$_2$CH$_3$)CO$_2$CH$_3$ | H | H | 173–173 |
| 488. | 4-Cl | 4-OCF$_2$CF$_2$H | N(CH$_2$CO$_2$CH$_3$)CO$_2$CH$_3$ | H | H | 158–160 |
| 489. | 4-Cl | 4-Cl | N(CH$_2$CO$_2$CH$_3$)CO$_2$CH$_3$ | H | H | 190–193 |
| 490. | 4-OCH$_2$CF$_3$ | 4-CF$_3$ | N(CH$_3$)CO$_2$CH$_3$ | H | H | 181–182 |
| 491. | 4-OCH$_2$CF$_3$ | 4-OCF$_3$ | N(CH$_3$)CO$_2$CH$_3$ | H | H | 173–175 |
| 492. | 4-OCH$_2$CF$_3$ | 4-OCF$_2$CF$_2$H | N(CH$_3$)CO$_2$CH$_3$ | H | H | 194–196 |
| 493. | 4-OCH$_2$CF$_3$ | 4-Cl | N(CH$_3$)CO$_2$CH$_3$ | H | H | 125–126 |
| 494. | 4-OCH$_2$CH$_2$CH$_3$, 3-CH$_3$ | 4-CF$_3$ | N(CH$_3$)CO$_2$CH$_3$ | H | H | 125–127 |
| 495. | 4-OCH$_2$CH$_2$CH$_3$, 3-CH$_3$ | 4-OCF$_3$ | N(CH$_3$)CO$_2$CH$_3$ | H | H | 124–126 |
| 496. | 4-OCH$_2$CH$_2$CH$_3$, 3-CH$_3$ | 4-OCF$_2$CF$_2$H | N(CH$_3$)CO$_2$CH$_3$ | H | H | 123–125 |
| 499. | 4-O(CH$_2$)$_3$CH$_3$ | 4-CF$_3$ | N(CH$_3$)CO$_2$CH$_3$ | H | H | 124–125 |
| 500. | 4-O(CH$_2$)$_3$CH$_3$ | 4-OCF$_2$CF$_2$H | N(CH$_3$)CO$_2$CH$_3$ | H | H | 141–142 |
| 501. | 4-OCF$_2$H,3-CH$_3$ | 4-CF$_3$ | N(CH$_2$CH$_2$CH$_3$)COCH$_2$CH$_3$ | H | H | 187–188 |
| 502. | 4-OCF$_2$H,3-CH$_3$ | 4-CF$_3$ | N(CH$_2$CH$_2$CH$_3$)COCH$_2$CH$_2$CH$_3$ | H | H | 176–177 |
| 503. | 4-OCF$_2$H,3-CH$_3$ | 4-CF$_3$ | N(CH$_2$CH$_2$CH$_3$)CO$_2$CH$_3$ | H | H | 161–163 |
| 504. | 4-OCF$_2$H,3-CH$_3$ | 4-CF$_3$ | N(CH$_2$CH$_2$CH$_3$)CO$_2$CH$_2$CH$_3$ | H | H | 140–141 |
| 505. | 4-OCF$_2$H,3-CH$_3$ | 4-CF$_3$ | N(CH$_2$CH$_2$CH$_3$)CH$_3$ | H | H | 133–135 |
| 506. | 4-OCF$_2$H,3-CH$_3$ | 4-CF$_3$ | N(CH$_2$CH$_2$CH$_3$)CH$_2$CH$_3$ | H | H | 136–138 |
| 507. | 4-OCF$_2$H,3-CH$_3$ | 4-CF$_3$ | N(CH$_2$CH$_2$CH$_3$)CH$_2$CH$_2$CH$_3$ | H | H | 160–161 |
| 508. | 4-OCF$_2$H,3-CH$_3$ | 4-CF$_3$ | N(CH$_2$CH$_2$CH$_3$)(CH$_2$)$_3$CH$_3$ | H | H | 137–139 |
| 509. | 4-OCH$_2$CH$_2$CH$_3$ | 4-CF$_3$ | N(CH$_2$CH$_3$)CO$_2$CH$_2$CCl$_3$ | H | H | 152–154 |
| 510. | 4-OCH$_2$CH$_2$CH$_3$ | 4-OCF$_3$ | N(CH$_2$CH$_3$)CO$_2$CH$_2$CCl$_3$ | H | H | 146–148 |
| 511. | 4-OCH$_2$CH$_2$CH$_3$ | 4-OCF$_2$CF$_2$H | N(CH$_2$CH$_3$)CO$_2$CH$_2$CCl$_3$ | H | H | 157–159 |
| 512. | 4-OCH$_2$CH$_2$CH$_3$ | 4-CF$_3$ | NHCH$_2$CH$_3$ | H | H | 106–108 |
| 513. | 4-OCH$_2$CH$_2$CH$_3$ | 4-OCF$_3$ | N(CH$_3$)CO$_2$CH$_3$ | H | H | 153–155 |
| 514. | 4-OCH$_2$CH$_2$CH$_3$ | 4-OCF$_2$CF$_2$H | N(CH$_3$)CO$_2$CH$_3$ | H | H | 149–151 |
| 515. | 4-O(CH$_2$)$_3$CH$_3$ | 4-CF$_3$ | N(CH$_3$)CO$_2$CH$_3$ | H | H | 124–125 |
| 516. | 4-OCH$_2$CH$_2$CH$_3$ | 4-CF$_3$ | N(CH$_2$CH$_3$)COCH$_2$CH$_3$ | H | H | 167–170 |
| 517. | 4-OCH$_2$CH$_2$CH$_3$ | 4-CF$_3$ | N(CH$_2$CH$_3$)COCH$_2$CH$_2$CH$_3$ | H | H | 168–171 |
| 518. | 4-OCH$_2$CH$_2$CH$_3$ | 4-CF$_3$ | N(CH$_2$CH$_3$)CO$_2$CH$_3$ | H | H | 183–185 |
| 519. | 4-OCH$_2$CH$_2$CH$_3$ | 4-CF$_3$ | N(CH$_2$CH$_3$)CO$_2$CH$_2$CH$_3$ | H | H | 180–183 |
| 520. | 4-OCH$_2$CH$_2$CH$_3$ | 4-CF$_3$ | N(CH$_2$CH$_3$)CHO | H | H | 166–166.5 |
| 521. | 4-OCH$_2$CH$_2$CH$_3$ | 4-CF$_3$ | N(CH$_2$CH$_3$)COCH$_3$ | H | H | 176–177 |
| 522. | 4-OCH$_2$CH$_2$CH$_3$ | 4-CF$_3$ | N(CH$_2$CH$_3$)COCF$_3$ | H | H | 165–167 |
| 523. | 4-OCF$_2$H,3-CH$_3$ | 4-CF$_3$ | NHCH$_2$CH$_3$ | H | H | 90–92 |
| 524. | 4-OCF$_2$H,3-CH$_3$ | 4-CF$_3$ | N(CH$_2$CH$_2$CH$_3$)CHO | H | H | 178–180 |
| 525. | 4-OCF$_2$H,3-CH$_3$ | 4-CF$_3$ | N(CH$_2$CH$_2$CH$_3$)COCH$_3$ | H | H | 187–188 |
| 526. | 4-OCF$_2$H,3-CH$_3$ | 4-CF$_3$ | N(CH$_2$CH$_2$CH$_3$)COCF$_3$ | H | H | 156–158 |
| 527. | 4-OCH$_2$CH$_2$CH$_3$ | 4-OCF$_3$ | NHCH$_2$CH$_3$ | H | H | 93–94 |
| 528. | 4-OCH$_2$CH$_2$CH$_3$ | 4-OCF$_3$ | N(CH$_2$CH$_3$)COCH$_2$CH$_3$ | H | H | 137–139 |
| 529. | 4-OCH$_2$CH$_2$CH$_3$ | 4-OCF$_3$ | N(CH$_2$CH$_3$)COCH$_2$CH$_2$CH$_3$ | H | H | 120–121 |
| 530. | 4-OCH$_2$CH$_2$CH$_3$ | 4-OCF$_3$ | N(CH$_2$CH$_3$)CO$_2$CH$_3$ | H | H | 113–116 |
| 531. | 4-OCH$_2$CH$_2$CH$_3$ | 4-OCF$_3$ | N(CH$_2$CH$_3$)CO$_2$CH$_2$CH$_3$ | H | H | 125–128 |
| 532. | 4-OCH$_2$CH$_2$CH$_3$ | 4-OCF$_3$ | N(CH$_2$CH$_3$)CHO | H | H | 129–132 |
| 533. | 4-OCH$_2$CH$_2$CH$_3$ | 4-OCF$_3$ | N(CH$_2$CH$_3$)COCH$_3$ | H | H | 153–154 |
| 534. | 4-OCH$_2$CH$_2$CH$_3$ | 4-OCF$_3$ | N(CH$_2$CH$_3$)COCF$_3$ | H | H | 186–187 |
| 535. | 4-OCH$_2$CH$_2$CH$_3$, 3-CH$_3$ | 4-Cl | N(CH$_3$)CO$_2$CH$_3$ | H | H | 129–130 |
| 540. | 4-OCH$_2$CH$_2$CH$_3$ | 4-OCF$_2$CF$_2$H | NHCH$_2$CH$_3$ | H | H | 110–112 |
| 541. | 4-Cl | 4-OCF$_3$ | NH$_2$ | H | H | 151–152 |
| 542. | 4-Cl | 4-OCF$_2$CF$_2$H | NH$_2$ | H | H | 173–174 |
| 543. | 4-Cl | 4-OCF$_2$CF$_2$H | NHCOCH$_2$CH$_2$CH$_2$Br | H | H | 225–226 |
| 544. | 4-Cl | 4-OCF$_2$CF$_2$H | NHCOCH$_2$CH$_2$CH$_2$Cl | H | H | 215–216 |
| 545. | 4-Cl | 4-OCF$_2$CF$_2$H | NHCO$_2$CH$_2$CH$_2$Cl | H | H | 206–207 |

TABLE I-continued

[Structure diagram with substituents Y, Z, Q, G, U, V on a pyrazoline-urea core]

| EX. | Q | G | Y | Z | V | mp °C. |
|---|---|---|---|---|---|---|
| 546. | 4-Cl | 4-OCF$_2$CF$_2$H | —N(pyrrolidinone) | H | H | 227–228 |
| 547. | 4-Cl | 4-OCF$_2$CF$_2$H | —N(piperidinone) | H | H | 238–239 |
| 548. | 4-Cl | 4-OCF$_2$CF$_2$H | —N(morpholinone) | H | H | 212–213 |
| 549. | 4-Cl | 4-CF$_3$ | NHCOCH$_2$CH$_2$CH$_2$Br | H | H | 237–238 |
| 550. | 4-Cl | 4-CF$_3$ | NHCOCH$_2$CH$_2$CH$_2$CH$_2$Cl | H | H | 216–217 |
| 551. | 4-Cl | 4-CF$_3$ | NHCO$_2$CH$_2$CH$_2$Cl | H | H | 212–213 |
| 552. | 4-Cl | 4-CF$_3$ | —N(pyrrolidinone) | H | H | 216–217 |
| 553. | 4-Cl | 4-CF$_3$ | —N(piperidinone) | H | H | 217–218 |
| 554. | 4-Cl | 4-CF$_3$ | —N(morpholinone) | H | H | 213–214 |
| 555. | 4-Cl | 4-OCF$_3$ | NHCOCH$_2$CH$_2$CH$_2$Br | H | H | 242–243 |
| 556. | 4-Cl | 4-OCF$_3$ | NHCOCH$_2$CH$_2$CH$_2$CH$_2$Cl | H | H | 220–221 |
| 557. | 4-Cl | 4-OCF$_3$ | NHCO$_2$CH$_2$CH$_2$Cl | H | H | 222–223 |
| 558. | 4-Cl | 4-OCF$_3$ | —N(pyrrolidinone) | H | H | 223–224 |
| 559. | 4-Cl | 4-OCF$_3$ | —N(piperidinone) | H | H | 225–226 |
| 560. | 4-Cl | 4-OCF$_3$ | —N(morpholinone) | H | H | 207–209 |
| 561. | 4-OCH$_2$CH$_2$CH$_3$ | 4-OCF$_2$CF$_2$H | N(CH$_2$CH$_3$)CO$_2$CH$_3$ | H | H | 150–153 |
| 562. | 4-OCH$_2$CH$_2$CH$_3$ | 4-OCF$_2$CF$_2$H | N(CH$_2$CH$_3$)CO$_2$CH$_2$CH$_3$ | H | H | 126–128 |

TABLE I-continued

| EX. | Q | G | Y | Z | V | mp °C. |
|---|---|---|---|---|---|---|
| 563. | 4-OCH$_2$CH$_2$CH$_3$ | 4-OCF$_2$CF$_2$H | N(CH$_2$CH$_3$)CHO | H | H | 119–122 |
| 564. | 4-OCH$_2$CH$_2$CH$_3$ | 4-OCF$_2$CF$_2$H | N(CH$_2$CH$_3$)COCH$_3$ | H | H | 130–132 |
| 565. | 4-OCH$_2$CH$_2$CH$_3$ | 4-OCF$_2$CF$_2$H | N(CH$_2$CH$_3$)COCF$_3$ | H | H | 195–196 |
| 566. | 4-OCH$_2$CH$_2$CH$_3$ | 4-OCF$_2$CF$_2$H | N(CH$_2$CH$_3$)COCH$_2$CH$_3$ | H | H | 143–146 |
| 567. | 4-OCH$_2$CH$_2$CH$_3$ | 4-OCF$_2$CF$_2$H | N(CH$_2$CH$_3$)COCH$_2$CH$_2$CH$_3$ | H | H | 140–144 |
| 568. | 4-OCH$_2$CH$_2$CH$_3$ | 4-CF$_3$ | N(CH$_3$)CO$_2$CH$_2$CCl$_3$ | H | H | 141–143 |
| 569. | 4-OCH$_2$CH$_2$CH$_3$ | 4-CF$_3$ | N(CH$_3$)$_2$ | H | H | 143–145 |
| 570. | 4-OCH$_2$CH$_2$CH$_3$ | 4-CF$_3$ | N(CH$_3$)CH$_2$CH$_3$ | H | H | 130–132 |
| 571. | 4-OCH$_2$CH$_2$CH$_3$ | 4-CF$_3$ | N(CH$_3$)CH$_2$CH$_2$CH$_3$ | H | H | 111–113 |
| 572. | 4-OCH$_2$CH$_2$CH$_3$ | 4-CF$_3$ | N(CH$_3$)CH(CH$_3$)$_2$ | H | H | 150–151 |
| 573. | 4-OCH$_2$CH$_2$CH$_3$ | 4-CF$_3$ | N(CH$_3$)(CH$_2$)$_3$CH$_3$ | H | H | 129–131 |
| 574. | 4-OCH$_2$CH$_2$CH$_3$ | 4-CF$_3$ | N(CH$_3$)(CH$_2$)$_4$CH$_3$ | H | H | 145–147 |
| 575. | 4-OCH$_2$CH$_2$CH$_3$ | 4-CF$_3$ | N(CH$_3$)(CH$_2$)$_5$CH$_3$ | H | H | 145–147 |
| 576. | 4-OCH$_2$CH$_2$CH$_3$ | 4-CF$_3$ | N(CH$_3$)CH$_2$C$_6$H$_5$ | H | H | 178–181 |
| 577. | 4-OCH$_2$CH$_2$CH$_3$ | 4-CF$_3$ | N(CH$_2$CH$_3$)$_2$CO$_2$CH$_3$ | H | H | 180–181 |
| 578. | 4-OCH$_2$CH$_2$CH$_3$ | 4-OF$_3$ | N(CH$_2$CH$_3$)$_2$CO$_2$CH$_3$ | H | H | 165–166 |
| 579. | 4-OCH$_2$CH$_2$CH$_3$ | 4-OCF$_2$CF$_2$H | N(CH$_2$CH$_3$)$_2$CO$_2$CH$_3$ | H | H | 159–160 |
| 580. | 4-OCH$_2$CH$_2$CH$_3$ | 4-Cl | N(CH$_2$CH$_3$)$_2$CO$_2$CH$_3$ | H | H | 186–187 |
| 581. | 4-OCH$_2$CH$_2$CH$_3$ | 4-CF$_3$ | N(CH$_2$CH(CH$_3$)$_2$)CHO | H | H | 188–190 |
| 582. | 4-OCH$_2$CH$_2$CH$_3$ | 4-OCF$_3$ | N(CH$_2$CH(CH$_3$)$_2$)CHO | H | H | 182–183 |
| 583. | 4-OCH$_2$CH$_2$CH$_3$ | 4-OCF$_2$CF$_2$H | N(CH$_2$CH(CH$_3$)$_2$)CHO | H | H | 171–172 |
| 584. | 4-OCH$_2$CH$_2$CH$_3$ | 4-Cl | N(CH$_2$CH(CH$_3$)$_2$)CHO | H | H | 191–193 |
| 585. | 4-OCH$_2$CH$_2$CH$_3$ | 4-CF$_3$ | N(CH$_2$CH$_2$CH$_3$)CO$_2$CH$_2$CCl$_3$ | H | H | 162–163 |
| 586. | 4-OCH$_2$CH$_2$CH$_3$ | 4-CF$_3$ | NHCH$_2$CH$_3$ | H | H | 130–133 |
| 587. | 4-OCH$_2$CH$_2$CH$_3$ | 4-CF$_3$ | N(CH$_2$CH$_2$CH$_3$)CHO | H | H | 161–163 |
| 588. | 4-OCH$_2$CH$_2$CH$_3$ | 4-CF$_3$ | N(CH$_2$CH$_2$CH$_3$)COCH$_3$ | H | H | 142–144 |
| 589. | 4-OCH$_2$CH$_2$CH$_3$ | 4-CF$_3$ | N(CH$_2$CH$_2$CH$_3$)COCF$_3$ | H | H | 175–177 |
| 590. | 4-OCH$_2$CH$_2$CH$_3$ | 4-CF$_3$ | N(CH$_2$CH$_2$CH$_3$)COCH$_2$CH$_3$ | H | H | 152–154 |
| 591. | 4-OCH$_2$CH$_2$CH$_3$ | 4-CF$_3$ | N(CH$_2$CH$_2$CH$_3$)COCH$_2$CH$_2$CH$_3$ | H | H | 125–127 |
| 592. | 4-OCH$_2$CH$_2$CH$_3$ | 4-CF$_3$ | N(CH$_2$CH$_2$CH$_3$)CO$_2$CH$_3$ | H | H | 142–145 |
| 593. | 4-OCH$_2$CH$_2$CH$_3$ | 4-CF$_3$ | N(CH$_2$CH$_2$CH$_3$)CO$_2$CH$_2$CH$_3$ | H | H | 145–147 |
| 594. | 4-O(CH$_2$)$_3$CH$_3$ | 4-CF$_3$ | N(CH$_2$CH$_2$CH$_3$)CHO | H | H | 157–158 |
| 595. | 4-O(CH$_2$)$_3$CH$_3$ | 4-OCF$_3$ | N(CH$_2$CH$_2$CH$_3$)CHO | H | H | 156–158 |
| 596. | 4-O(CH$_2$)$_3$CH$_3$ | 4-OCF$_2$CF$_2$H | N(CH$_2$CH$_2$CH$_3$)CHO | H | H | 177–178 |
| 597. | 4-O(CH$_2$)$_3$CH$_3$ | 4-Cl | N(CH$_2$CH$_2$CH$_3$)CHO | H | H | 153–156 |
| 598. | 4-OCH$_2$CH$_2$CH$_3$ | 4-CF$_3$ | N(CH$_2$CH$_2$OCH$_3$)CO$_2$CH$_3$ | H | H | 134–135 |
| 599. | 4-OCH$_2$CH$_2$CH$_3$ | 4-OCF$_3$ | N(CH$_2$CH$_2$OCH$_3$)CO$_2$CH$_3$ | H | H | 120–122 |
| 600. | 4-OCH$_2$CH$_2$CH$_3$ | 4-OCF$_2$CF$_2$H | N(CH$_2$CH$_2$OCH$_3$)CO$_2$CH$_3$ | H | H | 125–127 |
| 601. | 4-OCH$_2$CH$_2$CH$_3$ | 4-Cl | N(CH$_2$CH$_2$OCH$_3$)CO$_2$CH$_3$ | H | H | 136–138 |
| 602. | 4-OCF$_2$H | 4-OCF$_2$CF$_2$H | N(CH$_2$CH$_3$)$_2$ | H | H | 140–141 |
| 603. | 4-OCF$_2$H | 4-OCF$_2$CF$_2$H | N(CH$_2$CH$_2$CH$_3$)(CH$_2$)$_3$CH$_3$ | H | H | 111–113 |
| 604. | 4-OCF$_2$H,3-CH$_3$ | 4-CF$_3$ | N(CH$_2$CH$_2$CH$_3$)CO$_2$CH$_2$CCl$_3$ | H | H | 165–166 |
| 605. | 4-OCF$_2$H,3-CH$_3$ | 4-OCF$_3$ | N(CH$_2$CH$_2$CH$_3$)CO$_2$CH$_2$CCl$_3$ | H | H | 125–127 |
| 606. | 4-OCF$_2$H,3-CH$_3$ | 4-OCF$_2$CF$_2$H | N(CH$_2$CH$_2$CH$_3$)CO$_2$CH$_2$CCl$_3$ | H | H | 118–120 |
| 607. | 4-OCF$_2$H,3-CH$_3$ | 4-CF$_3$ | N(CH$_2$CH$_2$CH$_3$)CO$_2$CH$_2$CHCl$_2$ | H | H | 139–142 |
| 608. | 4-OCH$_2$CH$_2$CH$_3$ | 4-CF$_3$ | 2-oxo-2H-pyridin-1-yl | H | H | 183–185 |
| 609. | 4-OCH$_2$CH$_2$CH$_3$ | 4-OCF$_3$ | 2-oxo-2H-pyridin-1-yl | H | H | 132–135 |
| 610. | 4-OCH$_2$CH$_2$CH$_3$ | 4-OCF$_2$CF$_2$H | 2-oxo-2H-pyridin-1-yl | H | H | 202–204 |

TABLE I-continued

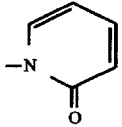

| EX. | Q | G | Y | Z | V | mp °C. |
|---|---|---|---|---|---|---|
| 611. | 4-OCH$_2$CH$_2$CH$_3$ | 4-Cl | -N-pyridinone | H | H | 142–145 |
| 612. | 4-OCH$_2$CH$_2$CH$_3$ | 4-OCF$_3$ | N(CH$_2$CH$_2$CH$_3$)CO$_2$CH$_2$CCl$_3$ | H | H | 155–155.5 |
| 613. | 4-OCH$_2$CH$_2$CH$_3$ | 4-OCF$_3$ | NHCH$_2$CH$_3$ | H | H | 93–95 |
| 614. | 4-OCH$_2$CH$_2$CH$_3$ | 4-OCF$_3$ | N(CH$_2$CH$_2$CH$_3$)CHO | H | H | 154–155 |
| 615. | 4-OCH$_2$CH$_2$CH$_3$ | 4-OCF$_3$ | N(CH$_2$CH$_2$CH$_3$)COCH$_3$ | H | H | 131–132 |
| 616. | 4-OCH$_2$CH$_2$CH$_3$ | 4-OCF$_3$ | N(CH$_2$CH$_2$CH$_3$)COCF$_3$ | H | H | 200–201 |
| 617. | 4-OCH$_2$CH$_2$CH$_3$ | 4-OCF$_3$ | N(CH$_2$CH$_2$CH$_3$)COCH$_2$CH$_3$ | H | H | 151–152 |
| 618. | 4-OCH$_2$CH$_2$CH$_3$ | 4-OCF$_3$ | N(CH$_2$CH$_2$CH$_3$)COCH$_2$CH$_2$CH$_3$ | H | H | oil |
| 619. | 4-OCH$_2$CH$_2$CH$_3$ | 4-OCF$_3$ | N(CH$_2$CH$_2$CH$_3$)CO$_2$CH$_3$ | H | H | 155–156 |
| 620. | 4-OCH$_2$CH$_2$CH$_3$ | 4-OCF$_3$ | N(CH$_2$CH$_2$CH$_3$)CO$_2$CH$_2$CH$_3$ | H | H | 135–136 |
| 621. | 4-OCH$_2$CH$_2$CH$_3$ | 4-CF$_3$ | N(CH$_2$CH$_2$OCH$_3$)CHO | H | H | 159–160 |
| 622. | 4-OCH$_2$CH$_2$CH$_3$ | 4-OCF$_3$ | N(CH$_2$CH$_2$OCH$_3$)CHO | H | H | 117–119 |
| 623. | 4-OCH$_2$CH$_2$CH$_3$ | 4-OCF$_2$CF$_2$H | N(CH$_2$CH$_2$OCH$_3$)CHO | H | H | 115–117 |
| 624. | 4-OCH$_2$CH$_2$CH$_3$ | 4-Cl | N(CH$_2$CH$_2$OCH$_3$)CHO | H | H | 125–127 |
| 625. | 4-OCH$_2$CH$_2$CH$_3$ | 4-CF$_3$ | N(CH$_2$CH=CH$_2$)CO$_2$CH$_3$ | H | H | 143–144 |
| 626. | 4-OCH$_2$CH$_2$CH$_3$ | 4-OCF$_3$ | N(CH$_2$CH=CH$_2$)CO$_2$CH$_3$ | H | H | 127–128 |
| 627. | 4-OCH$_2$CH$_2$CH$_3$ | 4-OCF$_2$CF$_2$H | N(CH$_2$CH=CH$_2$)CO$_2$CH$_3$ | H | H | 129–130 |
| 628. | 4-OCH$_2$CH$_2$CH$_3$ | 4-Cl | N(CH$_2$CH=CH$_2$)CO$_2$CH$_3$ | H | H | 128–129 |
| 629. | 4-OCH$_2$CH$_2$CH$_3$ | 4-OCF$_2$CF$_2$H | N(CH$_2$CH$_2$CH$_3$)CO$_2$CH$_2$CCl$_3$ | H | H | 150–150.5 |
| 630. | 4-OCH$_2$CH$_2$CH$_3$ | 4-OCF$_2$CF$_2$H | NHCH$_2$CH$_3$ | H | H | 103–105 |
| 631. | 4-OCH$_2$CH$_2$CH$_3$ | 4-OCF$_2$CF$_2$H | N(CH$_2$CH$_2$CH$_3$)CHO | H | H | 175–177 |
| 632. | 4-OCH$_2$CH$_2$CH$_3$ | 4-OCF$_2$CF$_2$H | N(CH$_2$CH$_2$CH$_3$)CO$_2$CH$_3$ | H | H | 160–162 |
| 633. | 4-OCH$_2$CH$_2$CH$_3$ | 4-OCF$_2$CF$_2$H | N(CH$_2$CH$_2$CH$_3$)CO$_2$CH$_2$CH$_3$ | H | H | 140–141 |
| 634. | 4-O(CH$_2$)$_3$CH$_3$ | 4-OCF$_2$CF$_2$H | N(CH$_3$)CO$_2$CH$_2$CCl$_3$ | H | H | 122–124 |
| 635. | 4-O(CH$_2$)$_3$CH$_3$ | 4-OCF$_2$CF$_2$H | NHCH$_3$ | H | H | 140–143 |
| 636. | 4-O(CH$_2$)$_3$CH$_3$ | 4-OCF$_2$CF$_2$H | N(CH$_3$)CHO | H | H | 168–169 |
| 637. | 4-O(CH$_2$)$_3$CH$_3$ | 4-OCF$_2$CF$_2$H | N(CH$_3$)COCH$_3$ | H | H | 169–171 |
| 638. | 4-O(CH$_2$)$_3$CH$_3$ | 4-OCF$_2$CF$_2$H | N(CH$_3$)COCF$_3$ | H | H | 183–184 |
| 639. | 4-O(CH$_2$)$_3$CH$_3$ | 4-OCF$_2$CF$_2$H | N(CH$_3$)COCH$_2$CH$_3$ | H | H | 166–167 |
| 640. | 4-O(CH$_2$)$_3$CH$_3$ | 4-OCF$_2$CF$_2$H | N(CH$_3$)COCH$_2$CH$_2$CH$_3$ | H | H | 149–151 |
| 641. | 4-O(CH$_2$)$_3$CH$_3$ | 4-OCF$_2$CF$_2$H | N(CH$_3$)CO$_2$CH$_3$ | H | H | 150–152 |
| 642. | 4-O(CH$_2$)$_3$CH$_3$ | 4-OCF$_2$CF$_2$H | N(CH$_3$)CO$_2$CH$_2$CH$_3$ | H | H | 152–153 |
| 643. | 4-OCH$_2$CH$_2$CH$_3$ | 4-CF$_3$ | N(CH$_2$CH=CH$_2$)CHO | H | H | 159–161 |
| 644. | 4-OCH$_2$CH$_2$CH$_3$ | 4-OCF$_3$ | N(CH$_2$CH=CH$_2$)CHO | H | H | 115–118 |
| 645. | 4-OCH$_2$CH$_2$CH$_3$ | 4-OCF$_2$CF$_2$H | N(CH$_2$CH=CH$_2$)CHO | H | H | 104–106 |
| 646. | 4-OCH$_2$CH$_2$CH$_3$ | 4-Cl | N(CH$_2$CH=CH$_2$)CHO | H | H | 115–118 |
| 647. | 4-O(CH$_2$)$_3$CH$_3$ | 4-CF$_3$ | NHCH$_2$CH$_3$ | H | H | 108–110 |
| 648. | 4-O(CH$_2$)$_3$CH$_3$ | 4-CF$_3$ | N(CH$_3$)CHO | H | H | 120–122 |
| 649. | 4-O(CH$_2$)$_3$CH$_3$ | 4-CF$_3$ | N(CH$_3$)COCH$_3$ | H | H | 157–159 |
| 650. | 4-O(CH$_2$)$_3$CH$_3$ | 4-CF$_3$ | N(CH$_3$)COCF$_3$ | H | H | 158–160 |
| 651. | 4-O(CH$_2$)$_3$CH$_3$ | 4-CF$_3$ | N(CH$_3$)COCH$_2$CH$_3$ | H | H | 146–148 |
| 652. | 4-O(CH$_2$)$_3$CH$_3$ | 4-CF$_3$ | N(CH$_3$)COCH$_2$CH$_2$CH$_3$ | H | H | 137–138 |
| 653. | 4-O(CH$_2$)$_3$CH$_3$ | 4-CF$_3$ | N(CH$_3$)CO$_2$CH$_3$ | H | H | 128–130 |
| 654. | 4-O(CH$_2$)$_3$CH$_3$ | 4-CF$_3$ | N(CH$_3$)CO$_2$CH$_2$CH$_3$ | H | H | 107–109 |
| 655. | 4-OCH$_2$CH$_2$CH$_3$ | 4-CF$_3$ | N(CH$_2$C≡CH)CO$_2$CH$_3$ | H | H | 172–174 |
| 656. | 4-OCH$_2$CH$_2$CH$_3$ | 4-OCF$_3$ | N(CH$_2$C≡CH)CO$_2$CH$_3$ | H | H | 138–140 |
| 657. | 4-OCH$_2$CH$_2$CH$_3$ | 4-OCF$_2$CF$_2$H | N(CH$_2$C≡CH)CO$_2$CH$_3$ | H | H | 130–133 |
| 658. | 4-OCH$_2$CH$_2$CH$_3$ | 4-Cl | N(CH$_2$C≡CH)CO$_2$CH$_3$ | H | H | 155–157 |
| 659. | 4-O(CH$_2$)$_3$CH$_3$ | 4-CF$_3$ | N(CH$_2$CH$_3$)CO$_2$CH$_2$CCl$_3$ | H | H | 122–124 |
| 660. | 4-O(CH$_2$)$_3$CH$_3$ | 4-OCF$_3$ | N(CH$_3$)CO$_2$CH$_2$CCl$_3$ | H | H | 120–122 |
| 661. | 4-O(CH$_2$)$_3$CH$_3$ | 4-CF$_3$ | N(CH$_2$CH$_3$)CO$_2$CH$_2$CCl$_2$H | H | H | 116–117 |
| 662. | 4-O(CH$_2$)$_3$CH$_3$ | 4-OCF$_3$ | NHCH$_2$CH$_3$ | H | H | 110–113 |
| 663. | 4-O(CH$_2$)$_3$CH$_3$ | 4-OCF$_3$ | N(CH$_2$CH$_3$)CHO | H | H | 110–111 |
| 664. | 4-O(CH$_2$)$_3$CH$_3$ | 4-OCF$_3$ | N(CH$_2$CH$_3$)COCH$_3$ | H | H | 131–132 |
| 665. | 4-O(CH$_2$)$_3$CH$_3$ | 4-OCF$_3$ | N(CH$_2$CH$_3$)COCF$_3$ | H | H | 173–173.5 |
| 666. | 4-O(CH$_2$)$_3$CH$_3$ | 4-OCF$_3$ | N(CH$_2$CH$_3$)COCH$_2$CH$_3$ | H | H | 128–130 |
| 667. | 4-O(CH$_2$)$_3$CH$_3$ | 4-OCF$_3$ | N(CH$_2$CH$_3$)COCH$_2$CH$_2$CH$_3$ | H | H | 116–117 |
| 668. | 4-O(CH$_2$)$_3$CH$_3$ | 4-OCF$_3$ | N(CH$_2$CH$_3$)CO$_2$CH$_3$ | H | H | 160–161 |

TABLE I-continued

| EX. | Q | G | Y | Z | V | mp °C. |
|---|---|---|---|---|---|---|
| 669. | 4-O(CH$_2$)$_3$CH$_3$ | 4-OCF$_3$ | N(CH$_2$CH$_3$)CO$_2$CH$_2$CH$_3$ | H | H | 141–143 |
| 670. | 4-OCH$_2$CH$_2$CH$_3$ | 4-CF$_3$ | N(CH$_2$C≡CH)CHO | H | H | 170–172 |
| 671. | 4-OCH$_2$CH$_2$CH$_3$ | 4-OCF$_3$ | N(CH$_2$C≡CH)CHO | H | H | 123–125 |
| 672. | 4-OCH$_2$CH$_2$CH$_3$ | 4-OCF$_2$CF$_2$H | N(CH$_2$C≡CH)CHO | H | H | 134–136 |
| 673. | 4-OCH$_2$CH$_2$CH$_3$ | 4-Cl | N(CH$_2$C≡CH)CHO | H | H | 125–127 |
| 674. | 4-O(CH$_2$)$_3$CH$_3$ | 4-CF$_3$ | N(CH$_2$CH$_3$)CH$_3$ | H | H | 143–144 |
| 675. | 4-O(CH$_2$)$_3$CH$_3$ | 4-CF$_3$ | N(CH$_2$CH$_3$)$_2$ | H | H | 110–111 |
| 676. | 4-O(CH$_2$)$_3$CH$_3$ | 4-CF$_3$ | N(CH$_2$CH$_3$)CH$_2$CH$_2$CH$_3$ | H | H | 115–116 |
| 677. | 4-O(CH$_2$)$_3$CH$_3$ | 4-CF$_3$ | N(CH$_2$CH$_3$)(CH$_2$)$_3$CH$_3$ | H | H | 112–113 |
| 678. | 4-O(CH$_2$)$_3$CH$_3$ | 4-CF$_3$ | N-linked 4-oxopyridinyl | H | H | 203–205 |
| 679. | 4-O(CH$_2$)$_3$CH$_3$ | 4-OCF$_3$ | N-linked 4-oxopyridinyl | H | H | 185–195 |
| 680. | 4-O(CH$_2$)$_3$CH$_3$ | 4-OCF$_2$CF$_2$H | N-linked 4-oxopyridinyl | H | H | 207–209 |
| 681. | 4-O(CH$_2$)$_3$CH$_3$ | 4-CF$_3$ | N-linked 1,2,4-triazolyl | H | H | 225–228 |
| 682. | 4-O(CH$_2$)$_3$CH$_3$ | 4-OCF$_3$ | N-linked 1,2,4-triazolyl | H | H | 203–206 |
| 683. | 4-O(CH$_2$)$_3$CH$_3$ | 4-OCF$_2$CF$_2$H | N-linked 1,2,4-triazolyl | H | H | 202–206 |
| 684. | 4-O(CH$_2$)$_3$CH$_3$ | 4-CF$_3$ | N(CH$_2$CH$_2$CN)CO$_2$CH$_3$ | H | H | 159–161 |
| 685. | 4-O(CH$_2$)$_3$CH$_3$ | 4-OCF$_3$ | N(CH$_2$CH$_2$CN)CO$_2$CH$_3$ | H | H | 169–170 |
| 686. | 4-O(CH$_2$)$_3$CH$_3$ | 4-OCF$_2$CF$_2$H | N(CH$_2$CH$_2$CN)CO$_2$CH$_3$ | H | H | 167–168 |
| 687. | 4-O(CH$_2$)$_3$CH$_3$ | 4-Cl | N(CH$_2$CH$_2$CN)CO$_2$CH$_3$ | H | H | 181–183 |
| 688. | 4-OCF$_2$H | 4-CF$_3$ | N(CH$_2$CH$_2$CH$_3$)CO$_2$CH$_2$CCl$_3$ | H | H | 128–129 |
| 689. | 4-OCF$_2$H | 4-OCF$_3$ | N(CH$_2$CH$_2$CH$_3$)CO$_2$CH$_2$CCl$_3$ | H | H | 140–141 |
| 690. | 4-OCF$_2$H | 4-OCF$_2$CF$_2$H | N(CH$_2$CH$_2$CH$_3$)CO$_2$CH$_2$CCl$_3$ | H | H | 138–140 |
| 691. | 4-OCF$_2$H | 4-CF$_3$ | NHCH$_2$CH$_2$CH$_3$ | H | H | 105–106 |
| 692. | 4-OCF$_2$H | 4-OCF$_3$ | NHCH$_2$CH$_2$CH$_3$ | H | H | 89–90 |
| 693. | 4-OCF$_2$H | 4-OCF$_2$CF$_2$H | NHCH$_2$CH$_2$CH$_3$ | H | H | 96–97 |
| 694. | 4-OCF$_2$H | 4-OCF$_2$CF$_2$H | N(CH$_2$CH$_2$CH$_3$)CHO | H | H | 160–163 |
| 695. | 4-OCF$_2$H | 4-OCF$_2$CF$_2$H | N(CH$_2$CH$_2$CH$_3$)COCH$_3$ | H | H | 185–187 |
| 696. | 4-OCF$_2$H | 4-OCF$_2$CF$_2$H | N(CH$_2$CH$_2$CH$_3$)COCF$_3$ | H | H | 158–161 |
| 697. | 4-OCF$_2$H | 4-OCF$_2$CF$_2$H | N(CH$_2$CH$_2$CH$_3$)COCH$_2$CH$_3$ | H | H | 185–187 |
| 698. | 4-OCF$_2$H | 4-OCF$_2$CF$_2$H | N(CH$_2$CH$_2$CH$_3$)COCH$_2$CH$_2$CH$_3$ | H | H | 143–144 |
| 699. | 4-OCF$_2$H | 4-OCF$_2$CF$_2$H | N(CH$_2$CH$_2$CH$_3$)CO$_2$CH$_3$ | H | H | 179–181 |
| 700. | 4-OCF$_2$H | 4-OCF$_2$CF$_2$H | N(CH$_2$CH$_2$CH$_3$)CO$_2$CH$_2$CH$_3$ | H | H | 135–137 |
| 701. | 4-OCF$_2$H | 4-OCF$_3$ | N(CH$_2$CH$_2$CH$_3$)CHO | H | H | 174–175 |
| 702. | 4-OCF$_2$H | 4-OCF$_3$ | N(CH$_2$CH$_2$CH$_3$)COCH$_3$ | H | H | 182–184 |
| 703. | 4-OCF$_2$H | 4-OCF$_3$ | N(CH$_2$CH$_2$CH$_3$)COCF$_3$ | H | H | 193–195 |
| 704. | 4-OCF$_2$H | 4-OCF$_3$ | N(CH$_2$CH$_2$CH$_3$)COCH$_2$CH$_3$ | H | H | 180–181 |
| 705. | 4-OCF$_2$H | 4-OCF$_3$ | N(CH$_2$CH$_2$CH$_3$)COCH$_2$CH$_2$CH$_3$ | H | H | 136–138 |
| 706. | 4-OCF$_2$H | 4-OCF$_3$ | N(CH$_2$CH$_2$CH$_3$)CO$_2$CH$_3$ | H | H | 170–173 |

TABLE I-continued

| EX. | Q | G | Y | Z | V | mp °C. |
|---|---|---|---|---|---|---|
| 707. | 4-OCF$_2$H | 4-OCF$_3$ | N(CH$_2$CH$_2$CH$_3$)CO$_2$CH$_2$CH$_3$ | H | H | 147–149 |
| 708. | 4-OCF$_2$H | 4-CF$_3$ | N(CH$_2$CH$_2$CH$_3$)CHO | H | H | 168–170 |
| 709. | 4-OCF$_2$H | 4-CF$_3$ | N(CH$_2$CH$_2$CH$_3$)COCH$_3$ | H | H | 170–171 |
| 710. | 4-OCF$_2$H | 4-CF$_3$ | N(CH$_2$CH$_2$CH$_3$)COCF$_3$ | H | H | 195–196 |
| 711. | 4-OCF$_2$H | 4-CF$_3$ | N(CH$_2$CH$_2$CH$_3$)COCH$_2$CH$_3$ | H | H | 166–167 |
| 712. | 4-OCF$_2$H | 4-CF$_3$ | N(CH$_2$CH$_2$CH$_3$)COCH$_2$CH$_2$CH$_3$ | H | H | 155–157 |
| 713. | 4-OCF$_2$H | 4-CF$_3$ | N(CH$_2$CH$_2$CH$_3$)CO$_2$CH$_3$ | H | H | 164–165 |
| 714. | 4-OCF$_2$H | 4-CF$_3$ | N(CH$_2$CH$_2$CH$_3$)CO$_2$CH$_2$CH$_3$ | H | H | 128–130 |
| 715. | 4-OCF$_2$H | 4-CF$_3$ | N(CH$_2$CH$_2$CH$_3$)CH$_3$ | H | H | 107–110 |
| 716. | 4-OCF$_2$H | 4-CF$_3$ | N(CH$_2$CH$_2$CH$_3$)CH$_2$CH$_3$ | H | H | 122–124 |
| 717. | 4-OCF$_2$H | 4-CF$_3$ | N(CH$_2$CH$_2$CH$_3$)$_2$ | H | H | 140–142 |
| 718. | 4-OCF$_2$H | 4-CF$_3$ | N(CH$_2$CH$_2$CH$_3$)(CH$_2$)$_3$CH$_3$ | H | H | 108–109 |
| 719. | 4-OCF$_2$H | 4-OCF$_3$ | N(CH$_2$CH$_2$CH$_3$)CH$_3$ | H | H | 100–104 |
| 720. | 4-OCF$_2$H | 4-OCF$_3$ | N(CH$_2$CH$_2$CH$_3$)CH$_2$CH$_3$ | H | H | 110–113 |
| 721. | 4-OCF$_2$H | 4-OCF$_3$ | N(CH$_2$CH$_2$CH$_3$)$_2$ | H | H | 118–120 |
| 722. | 4-OCF$_2$H | 4-OCF$_3$ | N(CH$_2$CH$_2$CH$_3$)(CH$_2$)$_3$CH$_3$ | H | H | 60–65 |
| 723. | 4-OCF$_2$H | 4-OCF$_2$CF$_2$H | N(CH$_2$CH$_2$CH$_3$)CH$_3$ | H | H | 121–123 |
| 724. | 4-OCF$_2$H | 4-OCF$_2$CF$_2$H | N(CH$_2$CH$_2$CH$_3$)CH$_2$CH$_3$ | H | H | 127–129 |
| 725. | 4-OCF$_2$H,3-CH$_3$ | 4-OCF$_3$ | N(CH$_2$CH$_2$CH$_3$)H | H | H | 93–94 |
| 726. | 4-OCF$_2$H,3-CH$_3$ | 4-OCF$_3$ | N(CH$_2$CH$_2$CH$_3$)CHO | H | H | 144–146 |
| 727. | 4-OCF$_2$H,3-CH$_3$ | 4-OCF$_3$ | N(CH$_2$CH$_2$CH$_3$)CO$_2$C$_2$H$_5$ | H | H | 118–119 |
| 728. | 4-OCF$_2$H,3-CH$_3$ | 4-OCF$_2$CF$_2$H | N(CH$_2$CH$_2$CH$_3$)H | H | H | 64–66 |
| 729. | 4-OCF$_2$H,3-CH$_3$ | 4-OCF$_2$CF$_2$H | N(CH$_2$CH$_2$CH$_3$)CHO | H | H | 153–155 |
| 730. | 4-OCF$_2$H,3-CH$_3$ | 4-OCF$_2$CF$_2$H | N(CH$_2$CH$_2$CH$_3$)COCH$_3$ | H | H | 155–156 |
| 731. | 4-OCF$_2$H,3-CH$_3$ | 4-OCF$_2$CF$_2$H | N(CH$_2$CH$_2$CH$_3$)COCH$_2$CH$_2$CH$_3$ | H | H | 147–149 |
| 732. | 4-OCF$_2$H,3-CH$_3$ | 4-OCF$_2$CF$_2$H | N(CH$_2$CH$_2$CH$_3$)CO$_2$CH$_3$ | H | H | 165–167 |
| 733. | 4-OCF$_2$H,3-CH$_3$ | 4-OCF$_2$CF$_2$H | N(CH$_2$CH$_2$CH$_3$)CO$_2$C$_2$H$_5$ | H | H | 125–127 |
| 734. | 4-OCF$_2$H,3-CH$_3$ | 4-OCF$_2$CF$_2$H | N(CH$_2$CH$_2$CH$_3$)SO$_2$CH$_3$ | H | H | 182–184 |
| 735. | 4-OCF$_2$H,3-CH$_3$ | 4-CF$_3$ | N(CH$_2$CH$_2$CH$_3$)CO$_2$CH$_2$CCL$_3$ | H | H | 156–158 |
| 736. | 4-OCF$_2$H,3-CH$_3$ | 4-CF$_3$ | N(CH$_2$CH$_2$CH$_6$)H | H | H | 144–146 |
| 737. | 4-OCF$_2$H,3-CH$_3$ | 4-CF$_3$ | N(CH$_2$CH$_2$CH$_3$)CHO | H | H | 188–190 |
| 738. | 4-OCF$_2$H,3-CH$_3$ | 4-CF$_3$ | N(CH$_2$CH$_2$CH$_3$)CO$_2$CH$_3$ | H | H | 152–154 |
| 739. | 4-OCF$_2$H,3-CH$_3$ | 4-CF$_3$ | N(CH$_2$CH$_2$CH$_3$)CO$_2$C$_2$H$_5$ | H | H | 129–132 |
| 740. | 4-OCF$_2$H,3-CH$_3$ | 4-CF$_3$ | N(CH$_2$CH$_2$CH$_3$)COCH$_3$ | H | H | 172–174 |
| 741. | 4-OCF$_2$H,3-CH$_3$ | 4-CF$_3$ | N(CH$_2$CH$_2$CH$_3$)COC$_2$H$_5$ | H | H | 165–167 |
| 742. | 4-OCF$_2$H,3-CH$_3$ | 4-CF$_3$ | N(CH$_2$CH$_2$CH$_3$)CH$_3$ | H | H | 134–136 |

TABLE II

| EX. | Q | G | Y | Z | V | mp °C. |
|---|---|---|---|---|---|---|
| 438. | 4-Cl | 4-Cl | N(CH$_3$)CO$_2$CH$_3$ | H | H | 195–197 |
| 439. | 4-Cl | 4-CF$_3$ | N(CH$_3$)CO$_2$CH$_3$ | H | H | 170–172 |
| 497. | 4-OCH$_2$CH$_2$CH$_3$ | 4-CF$_3$ | N(CH$_3$)CO$_2$CH$_3$ | H | H | 167–169 |

TABLE III

| EX. | Q | G | Y | Z | V | mp °C. |
|---|---|---|---|---|---|---|
| 498 | 4-OCH$_2$CH$_2$CH$_3$ | 4-CF$_3$ | N(CH$_3$)CO$_2$CH$_3$ | H | CH$_3$ | oil |
| 536 | 4-OCH$_2$CH$_2$CH$_3$ | 4-CF$_3$ | N(CH$_3$)CO$_2$CH$_3$ | H | CH$_2$CH$_3$ | oil |
| 537 | 4-OCH$_2$CH$_2$CH$_3$ | 4-CF$_3$ | N(CH$_3$)CO$_2$CH$_3$ | H | CH$_2$CH$_2$CH$_3$ | oil |
| 538 | 4-OCH$_2$CH$_2$CH$_3$ | 4-CF$_3$ | N(CH$_3$)CO$_2$CH$_3$ | H | CH$_2$C$_6$H$_5$ | oil |
| 539 | 4-OCH$_2$CH$_2$CH$_3$ | 4-CF$_3$ | N(CH$_3$)CO$_2$CH$_3$ | H | CH(CH$_3$)$_2$ | oil |
| 743 | 4-Cl | 4-CF$_3$ | N(CH$_2$CH$_2$CH$_3$)CHO | H | CH$_3$ | oil |
| 744 | 4-Cl | 4-CF$_3$ | N(CH$_2$CH$_2$CH$_3$)CHO | H | CH$_2$CH$_3$ | oil |
| 745 | 4-Cl | 4-CF$_3$ | N(CH$_2$CH$_2$CH$_3$)CHO | H | CH$_2$CH$_2$CH$_3$ | oil |
| 746 | 4-Cl | 4-CF$_3$ | N(CH$_2$CH$_2$CH$_3$)CHO | H | (CH$_2$)$_3$CH$_3$ | oil |
| 747 | 4-Cl | 4-CF$_3$ | N(CH$_2$CH$_2$CH$_3$)CHO | H | CH$_2$CH=CH$_2$ | oil |
| 748 | 4-Cl | 4-CF$_3$ | N(CH$_2$CH$_2$CH$_3$)CHO | H | CH$_2$CH$_2$OCH$_3$ | oil |
| 749 | 4-Cl | 4-CF$_3$ | N(CH$_2$CH$_2$CH$_3$)CHO | H | CH(CH$_3$)$_2$ | oil |
| 750 | 4-OCH$_2$CH$_2$CH$_3$ | 4-CF$_3$ | N(CH$_2$CH$_2$CH$_3$)CHO | H | CH$_3$ | oil |
| 751 | 4-OCH$_2$CH$_2$CH$_3$ | 4-CF$_3$ | N(CH$_2$CH$_2$CH$_3$)CHO | H | CH$_2$CH$_3$ | oil |
| 752 | 4-OCH$_2$CH$_2$CH$_3$ | 4-CF$_3$ | N(CH$_2$CH$_2$CH$_3$)CHO | H | CH$_2$CH$_2$CH$_3$ | oil |
| 753 | 4-OCH$_2$CH$_2$CH$_3$ | 4-CF$_3$ | N(CH$_2$CH$_2$CH$_3$)CHO | H | (CH$_2$)$_3$CH$_3$ | oil |
| 754 | 4-OCH$_2$CH$_2$CH$_3$ | 4-CF$_3$ | N(CH$_2$CH$_2$CH$_3$)CHO | H | CH$_2$CH=CH$_2$ | oil |
| 755 | 4-OCH$_2$CH$_2$CH$_3$ | 4-CF$_3$ | N(CH$_2$CH$_2$CH$_3$)CHO | H | CH$_2$CH$_2$OCH$_3$ | oil |
| 756 | 4-OCH$_2$CH$_2$CH$_3$ | 4-CF$_3$ | N(CH$_2$CH$_2$CH$_3$)CHO | H | CH(CH$_3$)$_2$ | oil |

TABLE IV

NMR DATA

Ex. No. (200 MHz, delta scale in ppm. in CDCl$_3$; Tetramethylsilane (TMS) standard)

| | |
|---|---|
| 11. | 1.6(s, 3H); 4.1(abq, 2H); 5.0(abq, 2H); 5.8(bs, 1H); 7.1–7.8(m, 13H); 8.2(bs,1H). |
| 15. | 0.9(m, 3H); 1.3(m, 1H); 1.5(m, 2H); 1.6(s,3H); 4.0(m, 2H); 4.1(abq, 2H); 5.5(1,s, 1H); 7.4(abq, 4H); 7.5(abq, 4H); 8.2(bs, 1H). |
| 33. | 1.6(s, 3H); 3.4(s, 3H); 3.6(s, 3H); 4.1(abq, 2H), 5.5 (bs, 1H); 7.1(s, 4H), 7.4(abq, 4H). |
| 42. | 1.1(t, 6H); 1.6(s, 3H); 2.8(m, 4H); 4.0(abq, 2H); 7.4(d, 2H); 7.6(abq, 4H); 8.3(d, 2H); 8.3(s, 1H). |
| 43. | 1.1(t, 3H); 1.4(bs, 1H); 1.6(s, 3H); 2.3(m, 1H); 2.7(m, 1H); 3.7(d, 1H); 4.2(d, 1H); 7.4(d, 2H); 7.6(abq, 4H); 8.1(d, 2H); 8.2(s, 1H). |
| 63. | 1.1(dd, 6H); 1.4(bs,1H); 1.6(s, 3H); 3.0(m, 1H); 4.0(abq, 2H); 7.6(abq, 4H); 7.7(abq, 4H); 8.2(bs, 1H). |
| 65. | 1.5(dd, 6H); 1.8(s, 3H); 3.6(s, 3H); 3.9(m, 1H); 4.1(abq, 2H); 7.5(abq, 4H); 7.6(abq, 4H); 8.3(s, 1H). |
| 408. | 0.9(t, 3H); 1.4(m, 2H); 1.6(m, 2H); 2.6(s, 3H); 3.80+3.85(bs, 3H); 4.1(m, 2H); 6.0+6.3(m, 1H); 7.3(m, 4H); 7.6(m, 4H); 8.1(s, 1H). |
| 460. | 1.3(t, 3H); 2.7(m, 2H); 2.7(s, 3H); 3.80+3.85(bs, 3H); 4.1(abq, 2H); 6.()+6.3(m, 1H); 7.3(m, 4H); 7.6(m, 4H); 8.1(s, 1H). |
| 498. | 1.1(t, 3H), 1.9(sextet, 2H); 2.3(s, 3H); 2.65+2.70(bs, 3H); 3.80+3.85(bs, 3H); 4.0(abq, 2H); 5.9+6.2(m, 1H); 7.0(m, 4H); 7.7(m, 4H). |
| 536. | 1.1(t, 3H); 1.3(t, 3H); 1.9(sextet, 2H); 2.65+2.70(bs, 3H); 3.0(q, 2H); 3.80+3.85(bs, 3H); 4.0(abq, 2H); 5.9+6.2(m, 1H); 7.0(m, 4H); 7.7(m, 4H). |
| 537. | 0.9(t, 3H); 1.1(t, 3H); 1.6(sextet, 2H); 1.9(sextet, 2H); 2.65+2.70(bs, 3H); 2.9(m, 2H); 3.80+3.85(bs, 3H); 4.0(abq, 2H); 5.9+6.2(m, 1H); 7.0(m, 4H); 7.7(m, 4H). |
| 538. | 1.1(t, 3H); 1.9(sextet, 2H); 2.65+2.70(bs, 3H); 3.80+3.85(bs, 3H); 3.9(abq, 2H); 4.2(s, 2H); 5.9+6.29(m, 1H); 7.0(m, 4H); 7.3(m, 5H); 7.7(m, 4H). |
| 539. | 1.1(t, 3H); 1.3(d, 6H); 1.9(sextet, 2H); 2.65+2.70(bs, 3H); 3.80+3.85(bs, 3H); 3.9(abq, 2H); 4.4(septet, 1H); |

TABLE IV-continued

NMR DATA

Ex. No. (200 MHz, delta scale in ppm, in CDCl$_3$; Tetramethylsilane (TMS) standard)

| | |
|---|---|
| 618. | 5.9+6.2(m, 1H); 7.0(m, 4H); 7.7(m, 4H).<br>0.8(t, 3H); 1.0(t, 3H); 1.1(t, 3H); 1.4(m, 2H); 1.8(m, 4H);<br>2.3(m, 2H); 3.0(m, 2H); 4.0(t, 2H); 4.1(abq, 2H);<br>6.4(bs, 1H); 6.9(d, 2H); 7.2(d, 2H); 7.6(d, 2H); 7.7(d, 2H);<br>8.1(s, 1H). |

EXPERIMENTAL

Example 1

N-(4-trifluoromethylphenyl)-3-(4-chlorophenyl)-4-carbomethoxyamino-4-methyl-4,5,-dihydro-1H-pyrazole-1-carboxamide a: N-(4-trifluoromethylphenyl)-3-(4-chlorophenyl)-4-carboxy-4-methyl-4,5-dihydro-1H-pyrazole-1-carboxamide To 250 grams (g) (569 mmole) of N-(4-trifluoromethylphenyl)-3-(4-chlorophenyl)-4-carbomethoxy-4-methyl-4,5-dihydro-1H-pyrazole-1-carboxamide (U.S. Pat. No. 4,663,341, compound 149) was added 250 ml of methanol and 250 milliliters (ml) of tetrahydrofuran. The mixture was warmed to 60° C. to achieve solution. Separately, 51 g (637 mmole) of 50% aqueous sodium hydroxide was dissolved in 100 ml of methanol. The two solutions were mixed while hot and stirred for 30 minutes whereon no starting material was present by TLC analysis. The mixture was acidified with 55 ml of 37% aqueous hydrochloric acid and 700 ml of tetrahydrofuran and 200 ml of water were then added to dissolve the products. The aqueous layer was separated, dried over magnesium sulfate, filtered, and concentrated in vacuo. The resulting solid was triturated with ethyl ether and dried in a vacuum oven to yield 234 g (97%) of carboxylic acid, mp 142°–3° C.

b: N-(4-trifluoromethylphenyl)-3-(4-chlorophenyl)-4-chlorocarbonyl-4-methyl-4,5-dihydro-1H-pyrazole-1-carboxamide To a suspension of 100 g (235 mmole) of N-(4-trifluoromethylphenyl)-3-(4-chlorophenyl)-4-carboxy-4-methyl-4,5-dihydro-1H-pyrazole-1-carboxamide in 300 ml of chloroform was added 38 g (319 mmole) of thionyl chloride and 1 g of dimethylformamide. The mixture was refluxed until solution was achieved and gas evolution ceased, about 2 hours. Then 200 ml of toluene was added and the solvents were evaporated in vacuo quantitatively yielding the solid acid chloride which was used unpurified in the next reaction, mp 164°–172° C.

c: N-(4-trifluoromethylphenyl)-3-(4-chlorophenyl)-4-azidocarbonyl-4-methyl-4,5-dihydro-1H-pyrazole-1-carboxamide To all of the acid chloride prepared in Example 1b (235 mmole) was added 500 ml of acetonitrile. The mixture was warmed to achieve solution and then cooled to 20° C., 20 g (308 mmole) of sodium azide was added and the mixture was stirred for 1 hour. Infared spectroscopy of the crude reaction mixture showed the reaction was complete. Most of the acetonitrile was removed in vacuo with the water bath temperature kept below 40° C. Then 500 ml of toluene was added and the mixture was filtered through Celite® to remove salts. This solution of the acyl azide was used as is in the next reaction.

d: N-(4-trifluoromethylphenyl)-3-(4-chlorophenyl)-4-isocyanato-4-methyl-4,5-dihydro-1H-pyrazole-1-carboxamide All the solution of acyl azide prepared in Example 1c was slowly warmed to reflux. When the internal temperature reached about 70° C. a gas was vigorously evolved. When reflux was achieved, gas evolution had ceased. After refluxing for 15 minutes the solvent was removed in vacuo and the resulting solid was triturated with about 250 ml of 50/50 ethyl ether/hexanes, yielding 99 g (99%) of isocyanate, mp 146°–149° C.

e: N-(4-trifluoromethylphenyl)-3-(4-chlorophenyl)-4-carbomethoxyamino-4-methyl-4,5-dihydro-1H-pyrazole-1-carboxamide A solution of 20 g (47 mmole) of N-(4-trifluoromethylphenyl)-3-(4-chlorophenyl)-4-isocyanato-4-methyl-4,5-dihydro-1H-pyrazole-1-carboxamide (Example 1d) in 200 ml of methanol was refluxed for 2 hours, concentrated in vacuo and recrystallized from ethyl acetate/hexanes yielding 19.8 g (92%) of a white solid, mp 179°–181° C.

Examples 34 and 44 were prepared by following substantially the same procedure and substituting the appropriate starting compound disclosed in U.S. Pat. No. 4,663,341.

Example 2

N-(4-trifluoromethylphenyl)-3-(4-chlorophenyl)-4-carbo-t-butoxyamino-4-methyl-4,5-dihydro-1H-pyrazole-1-carboxamide To 100 g (236 mmole) of N-(4-trifluoromethylphenyl)-3-(4-chlorophenyl)-4-isocyanato-4-methyl-4,5-dihydro-1H-pyrazole-1-carboxamide (Example 1d) was added 100 g of t-butanol, 10 g of pyridine, 10 g of triethylamine, and 100 ml of toluene. The mixture was refluxed for 2 hours, concentrated in vacuo, and triturated with about 250 ml of 1:1 ethyl ether/hexanes yielding 96 g (82%) of a white solid, mp 205°–206° C.

Examples 8–12, 14–23, 35–37, 45–47, 52–55, 61, 67, 81, 85 and 90 were were prepared by following substantially the same procedure and using the appropriate dihydropyrazole disclosed in U.S. Pat. No. 4,663,341 and, where necessary, substituting for t-butanol the appropriate compound selected from: ethanol, n-propanol, isopropanol, n-butanol, n-pentanol, benzyl alcohol, 2-methoxyethanol, 2-chloroethanol, phenol, hydroxyacetone, allyl alcohol, 2,2, 2-trifluoroethanol, propargyl alcohol, ethyl glycolate, glycolonitrile, 2-bromoethanol, 3-bromopropanol, methanethiol, ethanethiol, butanethiol, sarcosine ethyl ester, N-methylaniline or dimethylamine.

Example 3

N-(4-trifluoromethylphenyl)-3-(4-chlorophenyl)-4-amino-4-methyl-4,5-dihydro-1H-pyrazole-1-carboxamide To 74 g (149 mmole) of N-(4-trifluoromethylphenyl)-3-(4-chlorophenyl)-4-carbo-t-butoxyamino-4-methyl-4,5- dihydro-1H-pyrazole-1-carboxamide (Example 2) was added 74 g of trifluoroacetic acid and 74 g of chloroform. The mixture was refluxed for 40 minutes while gas was evolved and then an additional 20 minutes. The mixture was then concentrated in vacuo and then partitioned between ethyl ether and dilute aqueous sodium hydroxide. The organic layer was washed with brine, dried over magnesium sulfate, concentrated in vacuo, and the resulting solid was triturated with hexanes and filtered yielding 50 g (85%) of a white solid, mp 165°–167° C.

Example 13

N-(4-trifluoromethylphenyl)-3-(4-chlorophenyl)-4-methyl-4-acetoxy-4,5-dihydro-1H-pyrazole-1-carboxamide a: N-(4-trifluoromethylphenyl)-3-(4-chlorophenyl)-4-methyl-4-acetyl-4,5-dihydro-1H-pyrazole-1-carboxamide To 14 ml (102 mmole) of diisopropyl amine and 1 mg of phenanthroline in 150 ml of tetrahydrofuran cooled to −30° C. was added 40 ml (100 mmole) of 2.5M n-butyllithium in hexane. After stirring for 5 minutes a solution of 15 g (39 mmole) of N-(4-trifluoromethylphenyl)-3-(4-chlorophenyl)-4-methyl-4,5-dihydro-1H-pyrazole-1-carboxamide (U.S. Pat. No. 4,663,341, see experimental for compound 149) in 25 ml of tetrahydrofuran was added while maintaining the internal temperature between −30° C and −40° C. After stirring for 40 minutes the mixture was cooled to −70° C. and 20 ml of ethyl acetate was added. After stirring for 15 minutes the mixture was quenched with 20 ml of acetic acid, warmed to 0° C. and 25 ml of water was added. The organic layer was separated, concentrated in vacuo, dissolved in 200 ml of diethyl ether, washed with dilute aqueous hydrochloric acid, dilute aqueous sodium hydroxide, and brine. The mixture was dried over anhydrous magnesium sulfate, filtered, concentrated in vacuo, and crystallized from diethyl ether yielding 6.5 g of the title compound containing a small amount of starting material.

b: N-(4-trifluoromethylphenyl)-3-(4-chlorophenyl)-4-methyl-4-acetoxy-4,5-dihydro-1H-pyrazole-1-carboxamide To 2.0 g (4.7 mmole) of N-(4-trifluoromethylphenyl)-3-(4-chlorophenyl)-4-methyl-4-acetyl-4,5-dihydro-1H-pyrazole-1-carboxamide (Example 13a) in 10 ml of methylene chloride was added 2 g (9.8 mmole) of 85% 3-chloroperoxybenzoic acid (MCPBA). After standing for 72 hours at room temperature an additional 0.6 g of MCPBA was added and the reaction was let stand an additional 72 hours. The reaction mixture was diluted with diethyl ether, washed with dilute aqueous sodium bisulfite, dilute aqueous sodium bicarbonate, and brine. The resulting solution was dried over anhydrous magnesium sulfate, filtered, concentrated in vacuo, and crystallized from diethyl ether and hexanes to yield the title compound, a white solid, mp 92°–96° C.

Example 24

N-(4-trifluoromethylphenyl)-3-(4-chlorophenyl)-4-propanoylamino-4-methyl-4,5-dihydro-1H-pyrazole-1-carboxamide To 25 g (63 mmole) of N-(4-trifluoromethylphenyl)-3-(4-chlorophenyl)-4-amino-4-methyl-4,5-dihydro-1H-pyrazole-1-carboxamide (Example 3) dissolved in 300 ml of methylene chloride was added 5.5 g (69 mmole) of pyridine. The mixture was cooled to −20° C. and 7.0 g (75 mmole) of propanoyl chloride was added. The mixture was allowed to stir without additional cooling for 30 minutes and then was washed with 200 ml of water, and 200 ml of dilute aqueous hydrochloric acid. The organic layer was dried over magnesium sulfate, concentrated in vacuo and triturated with 200 ml of 50/50 ethyl ether/hexanes yielding 24.8 g of a white solid, mp 208°–209° C.

Examples 4–7, 25–30, 39–41, 56, 59, 64, 65, 68, 71, 75, 78, 79, 84, 86–89, 91, and 97–103 were prepared following substantially the same procedure using the appropriate starting material and substituting for propanoyl chloride the appropriate compound selected from: methyl isocyanate, ethoxycarbonyl isocyanate, thiophosgene, methanesulfonyl chloride, ethanesulfonyl chloride, 2,2,2-trifluoroethanesulfonyl chloride, chloromethanesulfonyl chloride, 2-chloroethanesulfonyl chloride, 1-butanesulfonyl chloride, trifluoromethanesulfonyl chloride, dimethylsulfamoyl chloride, benzoyl chloride, phenylacetyl chloride, 3-phenylpropionyl chloride, cinnamoyl chloride, 4-chlorobutyryl chloride, butyryl chloride, isobutyryl chloride, pivoyl chloride, valeryl chloride, isovaleryl chloride, hexanoyl chloride, heptafluorobutyryl chloride, 2,6-difluorobenzoyl isocyanate, pentafluoropropionic anhydride, formic acetic anhydride, acetic anhydride, trifluoroacetic anhydride, succinic anhydride, glutaric anhydride, methyl chloroformate or diethyl chlorophosphate.

Examples 31–33

N-(4-trifluoromethylphenyl)-3-(4-chlorophenyl)-4-methyl-4-(N-methyl-N-carbomethoxyamino)-4,5-dihydro-1H-pyrazole-1-carboxamide, N-methyl-N-(4-trifluoro-methylphenyl)-3-(4-chlorophenyl)-4-methyl-4-(N-methyl-N-carbomethoxyamino)-4,5-dihydro-1H-pyrazole-1-carboxamide and N-methyl-N-(4-trifluoromethylphenyl)-3-(4-chlorophenyl)-4-methyl-4-(N-carbomethoxyamino)-4,5-dihydro-1H-pyrazole-1-carboxamide To 0.25 g (6.25 mmole) of 60% sodium hydride in mineral oil that had been twice washed with hexanes was added 1 ml of dimethylformamide. To this suspension was added a solution of 2.25 g (5.0 mmole) of N-(4-trifluoromethylphenyl)-3-(4-chlorophenyl)-4-methyl-4-(N-carbomethoxyamino)-4,5-dihydro-1H-pyrazole-1-carboxamide (Example 1) in 5 ml of dimethylformamide. Hydrogen gas was evolved. After gas evolution ceased, 1 ml of methyl iodide was added and the reaction was stirred at room temperature for 1 hour. Partitioning between diethyl ether and water, washing with water, washing with brine, drying over anhydrous magnesium sulfate, concentration in vacuo, and chromatography over silica gel using hexanes, diethyl ether, and ethyl acetate yielded the compounds of Examples 31 (mp. 193°–4° C.), 32 (mp 128°–130° C.) and 33 (oil) and starting material.

Examples 57 and 58 were prepared following substantially the procedure used to obtain Examples 31 and 32 respectively.

Example 43

N-(4-trifluoromethylphenyl)-3-(4-chlorophenyl)-4-methyl-4-(N-ethylamino)-4,5-dihydro-1H-pyrazole-1-carboxamide To 25 g (63 mmole) of N-(4-trifluoromethylphenyl)-3-(4-chlorophenyl)-4-methyl-4-amino-4,5-dihydro-1H-pyrazole-1-carboxamide (Example 3) dissolved in 100 ml of acetonitrile and 100 ml of tetrahydrofuran was added 3.05 g (69 mmole) of acetaldehyde and 2.02 g (32 mmole) of sodium cyanoborohydride. To this solution was dropwise added 4.0 g (67 mmole) of acetic acid. After 45 minutes, some starting material was still present on tlc, an additional 1.1 g of acetaldehyde, 1.03 g of sodium cyanoborohydride, and 1.5 g of acetic acid were added and the reaction was allowed to stir for an additional 30 minutes. The reaction mixture was concentrated in vacuo, partitioned between diethyl ether and water, washed with dilute aqueous sodium hydroxide, washed with brine, dried over anhydrous magnesium sulfate, and concentrated in vacuo yielding 26 g of Example 43, an oil.

Examples 38, 42, 63, 66 and 169 were prepared following substantially the same procedure, substituting formaldehyde for acetaldhyde where necessary.

Example 49

N-(4-trifluoromethylphenyl)-3-(4-chlorophenyl)-4-methyl-4-(N-ethyl-N-carbomethoxyamino)-4,5-dihydro-1H-pyrazole-1-carboxamide To 26 g (61 mmole) of N-(4-trifluoromethylphenyl)-3-(4-chlorophenyl)-4-methyl-4-(N-ethylamino)-4,5-dihydro-1H-pyrazole-1-carboxamide (Example 43) in 200 ml of methylene chloride was added 10 g (106 mmole) of methyl chloroformate at −30° C. and allowed to warm to room temperature. After 20 hours, an additional 4 g of methyl chloroformate was added and 24 hours later yet an additional 4 g of methyl chloroformate was added. After another 24 hours, the resulting mixture was washed with aqueous sodium bicarbonate, dried over anhydrous magnesium sulfate, concentrated in vacuo, and chromatographed over silica gel using diethyl ether and hexanes to yield 12.3 g of Example 49, a white solid, mp 163°–164° C., and 10 g of starting material.

Example 48 was prepared following substantially the same procedure and substituting acetyl chloride for methyl chloroformate.

Example 50

N-(4-trifluoromethylphenyl)-3-(4-chlorophenyl)-4-methyl-4-(pyrid-2-ylamino)-4,5-dihydro-1H-pyrazole-1-carboxamide To 2.0 g (5.0 mmole) of N-(4-trifluoromethylphenyl)-3-(4-chlorophenyl)-4-methyl-4-amino-4,5-dihydro-1H-pyrazole-1-carboxamide (Example 3) in 4 g of dimethylformamide was added 1.0 g (6.5 mmole) of 2-bromopyridine. The mixture was refluxed for 2 hours and then cooled. Partitioning between diethyl ether and dilute aqueous sodium bicarbonate, washing with brine, drying over anhydrous magnesium sulfate, and chromatography over silica gel using diethyl ether and hexanes yielded 0.2 g of Example 50, a white solid, mp 130°–140° C.

Example 51 was prepared following substantially the same procedure and substituting bromopyrazine for 2-bromopyridine.

Example 69

N-(4-trifluoromethylphenyl)-3-(4-chlorophenyl)-4-methyl-4-isocyano-4,5-dihydro-1H-pyrazole-1-carboxamide To 4.5 g (10 mmole) of N-(4-trifluoromethylphenyl)-3-(4-chlorophenyl)-4-methyl-4-(N-formylamino)-4,5-dihydro-1H-pyrazole-1-carboxamide (Example 64) and 3.4 ml (23 mmole) of triethylamine in 25 ml of methylene chloride at reflux was slowly added 5.5 ml of a 2.0M solution of phosgene in methylene chloride. After refluxing for 30 minutes the mixture was twice washed with water, dried over anhydrous magnesium sulfate, filtered, concentrated in vacuo, and chromatographed on silica gel using diethyl ether and hexanes to yield 0.7 g of the title compound, a yellow solid, mp 171°–173° C.

Example 73

N-(4-trifluoromethylphenyl)-3-(4-chlorophenyl)-4-methyl-4-(5-chloropentanoylamino)-4,5-dihydro-1H-pyrazole-1-carboxamide To 6.0 g (15 mmole) of N-(4-trifluoromethylphenyl)-3-(4-chlorophenyl)-4-methyl-4-amino-4,5-dihydro-1H-pyrazole-1-carboxamide (Example 3) in 50 ml of methylene chloride was added 2.0 ml (15.5 mmole) of 5-chlorovaleryl chloride followed by 1.2 ml (14.9 mmole) of pyridine. After stirring overnight the reaction was washed with water, dried over anhydrous magnesium sulfate, concentrated in vacuo, and chromatographed on silica gel using diethyl ether, hexanes, and ethyl acetate to yield 5.0 g of Example 73, a white solid, mp 94°–95° C.

Example 74

N-(4-trifluoromethylphenyl)-3-(4-chlorophenyl)-4-methyl-4-(piperid-2-one-1-yl)-4,5-dihydro-1H-pyrazole-1-carboxamide To 3.45 g (6.7 mmole) of N-(4-trifluoromethylphenyl)-3-(4-chlorophenyl)-4-methyl-4-(5-chloropentanoylamino)-4,5-dihydro-1H-pyrazole-1-carboxamide (Example 73) dissolved in 15 ml of dimethylformamide was added 0.27 g (6.7 mmole) of 60% sodium hydride in one portion. After gas evolution had ceased the reaction mixture was let stand at room temperature for 18 hours. The resulting mixture was concentrated in vacuo, partitioned between methylene chloride and water, dried over anhydrous magnesium sulfate, concentrated in vacuo, triturated with diethyl ether and hexanes to yield 3 g of Example 74, a white solid, mp 196°–198° C.

Examples 60, 62 and 72 were prepared following substantially the same procedure and substituting compounds 55, 61, and 71 for Example 73.

Example 76

N-(4-trifluoromethyl)-3-(4-chlorophenyl)-4-phenoxy-4,5-dihydro-1H-pyrazole-1-carboxamide a: 2-phenoxy-4'-chloroacetophenone To 28.4 g (213 mmole) of anhydrous potassium carbonate suspended in 100 ml of methyl ethyl ketone was added 20 g (213 mmole) of phenol and 47 g (201 mmole) of 2-bromo-4'-chloroacetophenone. The reaction mixture was refluxed for 2.5 hours, cooled, concentrated in vacuo, partitioned between diethyl ether and water, washed with dilute aqueous sodium hydroxide, washed with brine, dried over anhydrous magnesium sulfate, filtered, and concentrated in vacuo to yield 25 g of 2-phenoxy-4'-chloroacetophenone, a white solid, mp 80°–83° C.

b: 2-phenoxy-1-(4-chlorophenyl)prop-2-enone

By substantially following the procedure given in Example 115c using 5.0 g (20 mmole) of 2-phenoxy-4'-chloroacetophenone (Example 76a) and methanol as solvent, 5 g of the desired compound, an oil, were obtained.

c: N-(4-trifluoromethyl)-3-(4-chlorophenyl)-4-phenoxy-4,5-dihydro-1H-pyrazole-1-carboxamide To 1.4 g (5.4 mmole) of 2-phenoxy-1-(4-chlorophenyl) prop-2-enone (Example 76b) in 8 g of methanol and 2 g of tetrahydrofuran was added 0.61 g (12.2 mmole) of hydrazine monohydrate and 0.70 g (11.7 mmole) of acetic acid. The mixture was stirred at room temperature for 30 minutes, concentrated in vacuo, partitioned between diethyl ether and water, washed with brine, dried over anhydrous magnesium sulfate, and filtered. The resulting solution of 3-(4-chlorophenyl)-4-phenoxy-4,5-dihydro-1H-pyrazole was treated with 1.3 g (7 mmole) of 4-trifluoromethylphenyl isocyanate and let stir for 1 hour. Concentration in vacuo and trituration with diethyl ether and hexanes gave 0.8 g of the desired compound, a white solid, mp 153°–155° C.

Example 77 was prepared following substantially the same procedure and substituting 4-chlorophenol for phenol.

Example 80

N-(4-trifluoromethylphenyl)-3-(4-chlorophenyl)-4-methyl-4-(succinimido-1-yl)-4,5-dihydro-1H-pyrazole-1-carboxamide A mixture of 3.7 g (7 mmole) of N-(4-trifluoromethylphenyl)-3-(4-chlorophenyl)-4-methyl-4-(3-carboxypropionylamino)-4,5-dihydro-1H-pyrazole-1-carboxamide (Example 79) and 0.7 g of anhydrous sodium acetate in 20 g of acetic anhydride was warmed to 90° C. overnight. The resulting mixture was concentrated in vacuo, partitioned between methylene chloride and water, dried over anhydrous magnesium sulfate, filtered, concentrated in vacuo, and triturated with diethyl ether to yield the title compound, a white solid, mp 203°–205° C.

Example 82

N-(4-trifluoromethylphenyl)-3-(4-chlorophenyl)-4-(N-methyl-N-methanesulfonylamino)-4,5-dihydro-1H-pyrazole-1-carboxamide To 0.46 g (12 mmole) of 60% sodium hydride that had been twice washed with hexanes was added 5 ml of dimethylformamide. To this slurry was slowly added a solution of 5.5 g (12 mmole) of N-(4-trifluoromethylphenyl)-3-(4-chlorophenyl)-4-(N-methyl-N-methanesulfonylamino)-4,5-dihydro-1H-pyrazole-1-carboxamide (Example 5) in 20 ml of dimethylformamide. When hydrogen evolution had ceased, 0.72 ml (12 mmole) of methyl iodide was added and the reaction was stirred for 2 hours. The mixture was partitioned between diethyl ether and water, washed with water and brine, dried over anhydrous magnesium sulfate, filtered, concentrated in vacuo and chromatographed over silica gel using ethyl acetate and hexanes to yield 3.4 g of the title compound, a white solid, mp 105°–112° C.

Example 96

N-(4-trifluoromethylphenyl)-3-(4-chlorophenyl)-4-methyl-4-propoxy-4,5-dihydro-1H-pyrazole-1-carboxamide a: 1-chloro-1-propoxyethane To 60 g (1000 mmole) of 1-propanol and 44 g (1000 mmole) of acetaldehyde was added 1 ml of 37% aqueous hydrochloric acid. After the exotherm, the mixture was cooled to 5° C. and an additional 100 ml of 37% aqueous hydrochloric acid was added. Finally, the mixture was saturated with gaseous anhydrous hydrochloric acid while maintaining the internal temperature between −5° C. and +5° C. Two layers formed and were separated. The organic layer was dried over anhydrous calcium chloride yielding 91 g of the title compound, an oil.

b: 2-propoxypropionitrile

To 91 g (749 mmole) of 1-chloro-1-propoxyethane (Example 96a) in 100 ml of benzene was slowly added 80 g (894 mmole) of cuprous cyanide. After the initial exotherm the mixture was refluxed for 30 minutes. The mixture was filtered, concentrated in vacuo, and distilled yielding 40 g of the title compound, bp 65°–100° C. at 40 torr, an oil.

c: 2-propoxy-4'-chloropropiophenone

To 25 g (222 mmole) of 2-propoxypropionitrile (Example 96b) in 100 ml of diethyl ether was dropwise added 200 ml (200 mmole) of 1.0M 4-chlorophenylmagnesium bromide. After refluxing for 30 minutes the reaction mixture was cautiously quenched with 20 ml of water followed by a mixture of 25 ml of sulfuric acid and 75 ml of water. After stirring for 30 minutes the organic layer was separated, washed with brine, dried over anhydrous magnesium sulfate, concentrated in vacuo, and distilled yielding 25.9 g of the title compound, bp 110°–125° C. at 0.3 torr.

d: 2-hydroxymethyl-2-propoxy-4'chloropropiophenone

To 10 g (44 mmole) of 2-propoxy-4'-chloropropiophenone (Example 96c) in 10 g of pyridine was added 1.7 g (57 mmole) of paraformaldehyde and 0.4 g of a 40% methanolic solution of benzyltrimethylammonium hydroxide (Triton® B). After warming at 70° C. for two hours an additional 1.0 g of paraformaldehyde and 1.0 g of triethylamine was added. After heating for an additional two hours the mixture was partitioned between diethyl ether and dilute aqueous hydrochloric acid. The organic layer was washed with brine, dried over anhydrous magnesium sulfate, and concentrated in vacuo to yield 11 g of the crude title compound mixed with starting material.

e: 2-methanesulfonyloxymethyl-2-propoxy-4'-chloropropiophenone

To 11 g (44 mmole) of crude 2-hydroxymethyl-2-propoxy-4'-chloropropiophenone (Example 96d) in 50 ml of methylene chloride was added 4.5 g (39 mmole) of methanesulfonyl chloride. The mixture was cooled to −40° C. and then 6.0 g (60 mmole) of triethylamine was slowly added. The mixture was allowed to warm to room temperature over 1 hour and was then washed with water, dilute aqueous hydrochloric acid, and brine. It was then dried over anhydrous magnesium sulfate, filtered, concentrated in vacuo, and chromatographed over silica gel using diethyl ether and hexanes to yield 5.5 g of the title compound, an oil.

f: N-(4-trifluoromethylphenyl)-3-(4-chlorophenyl)-4-methyl-4-propoxy-4,5-dihydro-1H-pyrazole-1-carboxamide To 3.5 g (10 mmole) of 2-methanesulfonyloxymethyl-2-propoxy-4'-chloropropiophenone (Example 96e) in 25 ml of methanol was added 1.5 g (18 mmole) of anhydrous sodium acetate, 2.5 g (41 mmole) of acetic acid and 1.0 g (20 mmole) of hydrazine monohydrate. The mixture was refluxed for one hour, concentrated in vacuo, partitioned between diethyl ether and water. The organic layer was washed with dilute aqueous sodium hydroxide and brine and then dried over anhydrous magnesium sulfate, filtered and concentrated to about 25 ml. To this solution of 3-(4-chlorophenyl)-4-methyl-4-propoxy-4,5-dihydro-1H-pyrazole-1-carboxamide was added 2.1 g (11 mmole) of 4-(trifluoromethyl)phenylisocyanate. After stirring for 1 hour the precipitated solid was filtered and washed with diethyl ether and hexanes yielding 3.3 g of the title compound, a white solid, mp 135°–138° C.

Example 104

N-(4-trifluoromethylphenyl)-3-(4-chlorophenyl)-4-methoxy-4,5-dihydro-1H-pyrazole-1-carboxamide a: 2-methoxy-4'-chloroacetophenone To 25 g (281 mmole) of methoxyacetonitrile in 100 ml of diethyl ether at reflux was added 250 ml (250 mmole) of 1.0M 4-chlorophenyl magnesium bromide in diethyl ether. After refluxing for 30 minutes the reaction mixture was hydrolyzed with a solution of 30 ml of concentrated sulfuric acid in 100 ml of water. The organic layer was washed with water and brine, dried over anhydrous magnesium sulfate, concentrated in vacuo, and dissolved in hexanes. The insolubles were filtered away and the resultant solution was concentrated and distilled yielding a clear liquid, bp 105°–115° C. at 1 torr. The oil solidified on standing.

b: 2-methoxy-1-(4-chlorophenyl)prop-2-enone

By substantially following the procedure of Example 115c using 10 g (50 mmole) of 2-methoxy-4'-chloroacetophenone (Example 104a) 9 g of 2-methoxy-1-(chlorophenyl)prop-2-enone, an oil, was obtained.

c: N-(4-trifluoromethylphenyl)-3-(4-chlorophenyl)-4-methoxy-4,5-dihydro-1H-pyrazole-1-carboxamide By substantially following the procedure of Example 115d using 6 g (30 mmole) of 2-methoxy-1-(4-chlorophenyl)prop-2-enone (Example 104b), 5.3 g of the desired compound, a white solid, mp 185°–186.5° C., was obtained.

Example 105 was prepared following substantially the same procedure and substituting propoxyacetonitrile for acetonitrile.

Example 115

N-(4-trifluoromethylphenyl)-3-(4-chlorophenyl)-4-(N-methyl-N-(2,2,2-trichloroethoxycarbonyl)amino)-4,5, dihydro-1H-pyrazole-1-carboxamide a: 2-dimethylamino-4'-chloroacetophenone To 66 g (1460 mmole) of anhydrous dimethylamine in 200 ml of methylene chloride and cooled to –30° C. was added a solution of 155 g (664 mmole) of 2-bromo-4'-chloroacetophenone in 200 ml of methylene chloride. After the addition was complete the reaction was allowed to warm to 20° C. Concentration in vacuo, partitioning between diethyl ether and 1M aqueous sodium hydroxide, washing with brine, drying over anhydrous magnesium sulfate, and reconcentration in vacuo gives 130 g of the title compound, an oil.

b: 2-(N-methyl-N-(2,2,2-trichloroethoxycarbonyl)amino)-4'-chloroacetophenone

Method i

To 130 g (660 mmole) of 2-dimethylamino-4'-chloroacetophenone (Example 115a) in 500 ml of methylene chloride cooled to 0° C. was added 153 g (720 mmole) of 2,2,2-trichloroethylchloroformate. After the addition was complete the reaction mixture was allowed to warm to 20° C. Concentration in vacuo partitioning between diethyl ether and 1M aqueous hydrochloric acid, washing with brine, drying over anhydrous magnesium sulfate, and reconcentration in vacuo gave a crude oil. Chromatography of this oil on silica gel using 15% diethyl ether in hexanes gave 84 g of the title compound, an oil.

Method ii

By substantially following the procedure of Example 126d (Method ii) and using 117 g (500 mmole) of 2-bromo-4'-chloroacetophenone and 100 g of 2,2,2-trichloroethylchloroform in place of methyl chloroformate one obtains 158 g of the title compound, an oil.

c: 2-(N-methyl-N-(2,2,2-trichloroethoxycarbonyl)amino)-1-(4-chlorophenyl)prop-2-enone To 21.5 g (60 mmole) of 2-(N-methyl-N-(2,2,2-trichloroethoxycarbonyl)amino)-4'-chloroacetophenone (Example 115b) in 100 ml of 1-propanol was added 9.7 g (120 mmole) of 37% formalin, 1 g of piperidine and 0.7 g of acetic acid. The mixture was refluxed for four hours, concentrated in vacuo, partitioned between diethyl ether and water, washed with brine, dried over anhydrous magnesium sulfate, and reconcentrated under vacuo, yielding 20 g of the title compound, an oil.

d: N-(4-trifluoromethylphenyl)-3-(4-chlorophenyl)-4-(N-methyl-N-(2,2,2-trichloroethoxycarbonyl)amino)-4,5-dihydro-1H-pyrazole-1-carboxamide To 35.7 g (96 mmole) of 2-(N-methyl-N-(2,2,2-trichloroethoxycarbonyl)amino)-1-(4-chlorophenyl)-prop-2-enone (Example 115c) in 60 ml of methanol was added 5.8 g (115 mmole) of hydrazine monohydrate. The mixture was refluxed for ten minutes, concentrated in vacuo, partitioned between diethyl ether and water, washed with brine, dried over anhydrous magnesium sulfate, and filtered. This yielded a diethyl ether solution of 3-(4-chlorophenyl)-4-(N-methyl-N-(2,2,2-trichloroethoxycarbonyl)amino)-4,5-dihydro-1H-pyrazole which was not isolated. To this solution was added 18 g (96 mmole) of 4-trifluoromethylphenyl isocyanate. After refluxing for 1 hour the mixture was concentrated in vacuo and chromatographed over silica gel using diethyl ether and hexanes to yield 17.3 g of the title compound, a white solid, mp 169°–170° C.

Examples 185, 214–219, 290, 301, 320 and 321 were prepared following substantially the same procedure and substituting where appropriate 2-bromoacetophenone or 2-bromo-4'-difluoromethoxyacetophenone for 2-bromo-4'-chloroacetophenone; 4-trifluoromethoxyphenyl isocyanatetrafluoroethoxy)phenyl isocyanate tetrafluoroethoxy)phenyl isocyanate for 4-trifluoromethyl isocyanate; and isopropylamine or ethylamine for methylamine.

Example 116

N-(4-trifluoromethylphenyl)-3-(4-chlorophenyl)-4-(N-methylamino)-4,5-dihydro-1H-pyrazole-1-carboxamide To 17.3 g (30 mmole) of N-(4-trifluoromethylphenyl)-3-(4-chlorophenyl)-4-(N-methyl-N-(2,2,2-trichloroethoxycarbonyl)amino)-4,5-dihydro-1H-pyrazole-1-carboxamide (Example 115) dissolved in 50 ml of methanol and 50 ml of tetrahydrofuran was added 14 g (233 mmole) of acetic acid and 3.95 g (60 mmole) of zinc dust. After stirring for 1 hour the reaction mixture was filtered, concentrated in vacuo, dissolved in diethyl ether, washed with water, 5% aqueous sodium bicarbonate, and brine and dried over anhydrous magnesium sulfate. Concentration in vacuo and chromatography over silica gel using diethyl ether, hexanes, and ethyl acetate yielded 7.3 g of the compound, of Example 116, a white solid, mp 148°–149° C.

Examples 186, 220, 247, 260, 275, 302, 303 and 325 were prepared following substantially the same procedure.

Example 126

N-(4-trifluoromethoxyphenyl)-3-(4-difluoromethoxy-phenyl)-4-(N-methyl-N-(methoxycarbonyl)amino)-4,5-dihydro-1H-pyrazole-1-carboxamide a: 4-difluoromethoxyacetophenone To 200 g (1470 mmole) of 4-hydroxyacetophenone dissolved in 1000 ml of dimethylformamide and cooled to 10°

C. was added gaseous chlorodifluoromethane until the mixture was saturated. While vigorously mechanically stirring the mixture, 330 g (2600 mmole) of 45% aqueous potassium hydroxide was added while cofeeding chlorodifluoromethane to maintain an excess. The internal temperature was maintained at 10° C. during the addition. After standing overnight, the reaction mixture was carefully poured onto 5000 ml of water, gas is released! Extraction with a mixture of diethyl ether and hexanes, drying over anhydrous magnesium sulfate, and vacuum distillation yields 173 g of 4-difluoromethoxyacetophenone, an oil, bp 65°–70° C. at 0.2 torr.

b: 2-bromo-4'-difluoromethoxyacetophenone

To 173 g (930 mmole) of 4-difluoromethoxyacetophenone (Example 126a) dissolved in 150 ml of methylene chloride was added a few drops of bromine. The mixture was heated until the bromine color dissipated and then 25 ml of dioxane was added followed by 45 g (872 mmole) of bromine over the course of 30 minutes. Hydrogen bromide evolved. After the addition was complete the solvents are removed in vacuo and the product is taken up in diethyl ether and washed with water and brine. After drying over anhydrous magnesium sulfate the mixture was concentrated in vacuo and crystallized from 200 ml of 1:1 diethyl ether/hexanes yielding 164 g of the title compound, a white solid, mp 64°–66° C.

c: 2-dimethylamino-4'-difluoromethoxyacetophenone

By substantially following the procedure of Example 115a using 20 g (75 mmole) of 2-bromo-4'-difluoromethoxyacetophenone (Example 126b) 16.8 g of 2-dimethylamino-4'-difluoromethoxyacetophenone, an oil, was obtained.

d: 2-(N-methyl-N-(methoxycarbonyl)amino)-4'-difluoromethoxyacetophenone

Method i

By substantially following the procedure of Example 115b using 16.8 g (73 mmole) of 2-dimethylamino-4'-difluoromethoxy-acetophenone Example 126c and 7.6 g (81 mmole) of methyl chloroformate one obtain 12 g of 2-(N-methyl-N-(methoxycarbonyl)amino)-4'-difluoromethoxyacetophenone an oil. bp 150°–190° C. at 0.7 torr.

Method ii

To 47 g (1510 mmole) of monomethylamine dissolved in 300 ml of methylene chloride and cooled to −50° C. was added a solution of 136 g (512 mmole) of 2-bromo-4'-difluoromethoxyacetophenone (Example 126b) in 200 ml of methylene chloride. The internal temperature rose to 15° C. This mixture was allowed to stir for 15 minutes and then a solution of 40 g (500 mmole) of 50% aqueous sodium hydroxide in 100 ml of water was added. The resulting mixture was rapidly washed with two 500 ml portions of water. The resulting organic layer was cooled to 5° C. and 52 g (550 mmole) of methyl chloroformate and a mixture of 40 g (500 mmole) of 50% aqueous sodium hydroxide in 150 ml of water were simultaneously added with rapid stirring. The internal temperature was maintained between 0° C. and 10° C. After 10 minutes the organic layer was separated and washed with water and dilute aqueous hydrochloric acid. After drying over anhydrous magnesium sulfate, the methylene chloride was removed in vacuo and the diethyl ether soluble portion was filtered through silica gel. Concentration in vacuo yielded 90 g of the title compound as a tan solid, mp 50°–52° C.

e: 2-(N-methyl-N-(methoxycarbonyl)amino)-1-(4-difluoromethoxyphenyl)-prop-2-enone By substantially following the procedure of Example 115c, using 9.1 g (33 mmole) of 2-(N-methyl-N-(methoxycarbonyl)amino)-4'-difluoromethoxyacetophenone (Example 126d) was used to obtain 5.1 g of the title compound, an oil.

f: N-(4-trifluoromethoxyphenyl)-3-(4-difluoromethoxyphenyl)-4-(N-methyl-N-(methoxycarbonyl)amino)-4,5-dihydro-1H-pyrazole-1-carboxamide By substantially following the procedure of Example 115d, using 3.1 g (10 mmole) of 2-(N-methyl-N-(methoxycarbonyl)amino)-1-(4-difluoromethoxyphenyl) prop-2-enone (Example 126e) and 2.0 g (10 mmole) of 4-trifluoromethoxyphenyl isocyanate yields 2.1 g of the title compound, a white solid, mp 125°–126° C.

Examples 92–94, 109–114, 123–125, 127–131, 150–153, 319 and 337–342 were prepared following substantially the same procedure.

Example 145

N-(4-trifluoromethoxyphenyl)-3-(4-chlorophenyl)-4-(N-propargyl-N-carbomethoxyamino)-4,5-dihydro-1H-pyrazole-1-carboxamide a: 2-(N-propargyl-N-carbomethoxyamino)-4'-chloroacetophenone To 25 g (454 mmole) of propargylamine in 200 ml of methylene chloride cooled to −40° C. was rapidly added 46 g (200 mmole) of 2-bromo-4'-chloroacetophenone dissolved in 200 ml of methylene chloride. The temperature rose to 0° C. and was maintained there for 15 minutes. The reaction mixture was washed with 250 ml of 1M sodium hydroxide and recooled to −20° C. whereon 22 g (233 mmole) of methyl chloroformate was added while maintaining an internal temperature of −20° C., then 20 g (253 mmole) of pyridine was added. After stirring for 1 hour the mixture was concentrated in vacuo, partitioned between diethyl ether and water, washed with dilute hydrochloric acid, washed with brine, dried over anhydrous magnesium sulfate, reconcentrated in vacuo, and chromatographed over silica gel using diethyl ether and hexanes to yield 34 g of the expected compound, an oil.

b: 2-(N-propargyl-N-carbomethoxyamino)-1-(4-chlorophenyl)-prop-2-enone

By substantially following the procedure given in Example 115c using 9.9 g of 2-(N-propargyl-N-carbomethoxyamino)-4'-chloroacetophenone 9.7 g of the desired compound, an oil, was obtained.

c: N-(4-trifluoromethoxyphenyl)-3-(4-chlorophenyl)-4-(N-propargyl-N-carbomethoxyamino)-4,5-dihydro-1H-pyrazole-1-carboxamide By substantially following the procedure given in Example 115d using 2.3 g (8.3 mmole) of 2-(N-propargyl-N-carbomethoxyamino)-1-(4-chlorophenyl)prop-2-enone (Example 145b) and 1.7 g (8.4 mmole) of 4-trifluoromethoxyphenyl isocyanate, 1.4 g of the desired compound, mp 184°–185° C., were obtained.

Examples 132–144 and 146 were prepared following substantially the same procedure and substituting where appropriate, propylamine, ethylamine or allylamine for propargylamine; and 4-chlorophenyl isocyanate, 4-trifluoromethylphenyl isocyanate, 4-difluoromethoxyphenyl isocyanate, 4-(1,1,2,2-tetrafluoroethoxy)phenyl isocyanate or 4-bromophenyl isocyanate for 4-trifluoromethoxyphenyl isocyanate.

Example 154

N-(4-trifluoromethylphenyl)-3-(4-chlorophenyl)-4-(N-(2,2,2-trichloroethoxycarbonyl) amino)-4,5-dihydro-1H-pyrazole-1-carboxamide a: 2-(N-(2,2,2-trichloroethoxycarbonyl)amino)-4'-chloroacetophenone To a slurry of 30 g (214 mmole) of hexamethylenetetramine in 400 ml of acetonitrile was added 50 g (214 mmole) of 2-bromo-4'-chloroacetophenone in 100 ml of warm acetonitrile, the mixture self warms to 45° C. After stirring for 1 hour the mixture was diluted with diethyl ether and filtered giving a crude quaternary salt which was used directly in the next step.

To a slurry of this crude quaternary salt in 400 ml of ethanol was added 80 ml of 37% aqueous hydrochloric acid. After stirring for 1 hour all was in solution. The resulting mixture was concentrated in vacuo, basified with dilute aqueous sodium hydroxide and extracted with methylene chloride giving a solution of crude 2-amino-4'-chloroacetophenone which was used as is in the next step.

The methylene chloride solution of 2-amino-4'-chloroacetophenone was cooled to 0° C. and 80 g (377 mmole) of 2,2,2-trichloroethylchloroformate was added along with 60 g of 25% aqueous sodium hydroxide. Separation of the organic layer, drying over anhydrous magnesium sulfate, concentration in vacuo and trituration with diethyl ether and hexanes gave 63 g of the 2-(N-(2,2,2-triehloroethoxycarbonylamino)-4'-chloroacetophenone, a white solid, mp 104°–105° C.

b: 2-(N-(2,2,2-trichloroethoxycarbonyl)amino)-1-(4-chlorophenyl)prop-2-enone

To 37 g (107 mmole) of 2-(N-(2,2,2-trichloroethoxycarbonyl)amino)-4'-chloroacetophenone (Example 154a) in 100 ml of methanol was added 17.4 g (214 mmole) of 37% formalin, 1.7 g of piperidine and 1.2 g of acetic acid. The mixture was refluxed for 1 hour, concentrated in vacuo, partitioned between diethyl ether and water, washed with brine, dried over anhydrous magnesium sulfate, and concentrated in vacuo to yield 36.6 g of the title compound, an oil.

c: N-(4-trifluoromethylphenyl)-3-(4-chlorophenyl)-4-(N-(2,2,2-trichloroethoxycarbonyl)amino)-4,5-dihydro-1H-pyrazole-1-carboxamide To 36.6 g (102 mmole) of 2-(N-(2,2,2-trichloroethoxycarbonyl)amino)-1-(4-chlorophenyl)prop-2-enone (Example 154b) in 50 ml of methanol was added 6 g (120 mmole) of hydrazine monohydrate. The reaction mixture was refluxed for 15 minutes, cooled, concentrated in vacuo, partitioned between diethyl ether and water, washed with brine, and dried over anhydrous magnesium sulfate. The resulting solution of 3-(4-chlorophenyl)-4-(N-(2,2,2-trichloroethoxycarbonyl)amino)-4,5-dihydro-1H-pyrazole was treated, at reflux, with 19 g (102 mmole) of 4-trifluoromethyphenyl isocyanate. The precipitate was filtered and dried yielding 17 g of the compound of Example 154, a white solid, mp 121°–122° C.

Examples 95, 148, 149, 173 and 194 were prepared following substantially the same procedure and where appropriate substituting methyl chloroformate for 2,2,2-trichloroethylchloroformate; 2-bromoacetophenone or 2-bromo-4'-difluoromethoxyacetophenone for 2-bromo-4'-chloroacetophenone; and 4-trifluoromethoxyphenyl isocyanate for 4-trifluoromethylphenyl isocyanate.

Example 155

N-(4-trifluoromethylphenyl)-3-(4-chlorophenyl)-4-amino-4,5-dihydro-1H-pyrazole-1-carboxamide To 20 g (36 mmole) of N-(4-trifluoromethylphenyl)-3-(4-chlorophenyl)-4-(N-(2,2,2-trichloroethoxycarbonyl)amino)-4,5-dihydro-1H-pyrazole-1-carboxamide (Example 154) in 50 ml of methanol and 50 ml of tetrahydrofuran was added 4.69 g (72 mmole) of zinc dust and 16 g (267 mmole) of acetic acid. After stirring for 1 hour the reaction was filtered, concentrated in vacuo, partitioned between diethyl ether and water, washed with 5% aqueous sodium bicarbonate, washed with brine, dried over anhydrous magnesium sulfate, concentrated in vacuo, and chromatographed on silica gel using methylene chloride and ethyl acetate to yield 6 g of the title compound, a white solid, mp 144°–146° C.

Examples 174, 195 and 203 were prepared following substantially the same procedure starting from Examples 173, 195 and 212.

Example 204 was isolated as a side product of the preparation of Example 195.

Example 160

N-(4-trifluoromethylphenyl)-3-(4-chlorophenyl)-4-trifluoroacetylamino-4,5-dihydro-1H-pyrazole-1-carboxamide To 1.9 g (5.0 mmole) of N-(4-trifluoromethylphenyl)-3-(4-chlorophenyl)-4-amino-4,5-dihydro-1H-pyrazole-1-carboxamide (Example 155) in 10 ml of methylene chloride was added 1.1 g (5.2 mmole) of trifluoroacetic anhydride followed by 0.40 g (5.1 mmole) of pyridine. After stirring for 1 hour the reaction mixture was concentrated in vacuo, partitioned between ethyl acetate and water, washed with brine, dried over anhydrous magnesium sulfate, concentrated in vacuo, and triturated with diethyl ether and hexanes to yield 1.8 g of the title compound, a white solid, mp 259°–260° C.

Examples 156–159, 161, 175–184, 197–202 and 205–213 were prepared following substantially the same procedure starting from Examples 155, 174, 195 and 203 and where appropriate substituting for trifluoroacetic anhydride a compound selected from: methanesulfonyl chloride, propionyl chloride, formic acetic anhydride, acetic anhydride, propionyl chloride, butyryl chloride, methyl chloroformate, ethyl chloroformate, n-propyl chloroformate, isopropyl chloroformate or S-ethyl thiochloroformate.

Example 165

N-(4-trifluoromethylphenyl)-3-(4-chlorophenyl)-4-(N-methyl-N-(isobutyryl)amino)-4,5-dihydro-1H-pyrazole-1-carboxamide To 1.8 g (4.5 mmole) of N-(4-trifluoromethylphenyl)-3-(4-chlorophenyl)-4-(N-methylamino)-4,5-dihydro-1H-pyrazole-1-carboxamide (Example 116) in 10 ml of ethyl acetate cooled to 0° C. was added 0.5 g (4.7 mmole) of isobutyryl chloride and 0.4 g of pyridine. After stirring overnight the mixture was diluted with ethyl acetate, washed with water and brine and dried over anhydrous magnesium sulfate. Concentration in vacuo and trituration with diethyl ether gave 1.7 g of the title compound, a white solid, mp 180°–182° C.

Examples 106–108, 117–122, 162–164, 166–168, 170, 187–193, 222–236, 238–246, 248–259, 261–274, 276–289, 291–296, 304–318, 322–324 and 326–336 were prepared following substantially the same procedure starting from Examples 115, 186, 220, 247, 260, 275, 302, 303 or 326 and where appropriate substituting for isobutyryl chloride a compound selected from: propionyl chloride, n-butyryl chloride, methyl chloroformate, ethyl chloroformate, n-propyl chloroformate, isopropyl chloroformate, S-ethyl thiochloroformate, isobutyl chloroformate, allyl chloroformate, propargyl chloroformate, benzyl chloroformate, phenyl chloroformate, 2-chloroethyl chloroformate, acetic anhydride, benzoyl chloride, ethyl oxalyl chloride, methyl isocyanate, dimethylcarbamyl chloride, formic acetic anhydride, methanesulfonyl chloride, ethanesulfonyl chloride, phenylsulfonyl chloride, 4-chlorophenylsulfonyl chloride, trifluoroacetic anhydride, diethyl chlorophosphate, diethyl chlorothiophosphate, 4-trifluoromethoxyphenyl isocyanate, di-t-butyl dicarbonate, pivaloyl chloride, methoxyacetyl chloride, trichloroacetyl chloride, acryloyl chloride, methacrylic anhydride, crotonyl chloride, 3,3-dimethylacryloyl chloride, pentafluoropropionic anhydride, heptafluorobutyryl chloride or trichloroacryloyl chloride.

Example 171

N-(4-trifluoromethyl)-3-(4-chlorophenyl)-4-methylthio-4,5-dihydro-1H-pyrazole-1-carboxamide a: 2-methylthio-4'-chloroacetophenone To 11.3 g (141 mmole) of 50% aqueous sodium hydroxide dissolved in 50 ml of methanol and cooled to −20° C. was added 7.7 g (160 mmole) of gaseous methyl mercaptan. To this solution was added 30.5 g (130 mmole) of 2-bromo-4'-chloroacetophenone dissolved in 40 g of tetrahydrofuran. After warming to room temperature and stirring for 30 minutes the mixture was concentrated in vacuo, partitioned between hexanes and water, dried over anhydrous magnesium sulfate, filtered, and reconcentrated in vacuo to yield 25.3 g of 2-methylthio-4'-chloroacetophenone, an oil.

b: 2-methylthio-1-(4-chlorophenyl)prop-2-enone

To 11.0 g (55 mmole) of 2-methylthio-4'-chloroacetophenone (Example 117a) in 100 ml of methanol was added 8.9 g (110 mmole) of 37% formalin, 1.0 g of piperidine and 0.7 g of acetic acid. After stirring for 45 minutes at room temperature, the mixture was concentrated in vacuo, partitioned between diethyl ether and water and dried over anhydrous magnesium sulfate, and concentrated to yield the desired compound, an oil.

c: N-(4-trifluoromethyl)-3-(4-chlorophenyl)-4-methylthio-4,5-dihydro-1H-pyrazole-1-carboxamide By substantially following the procedure of Example 115d using 13 g (60 mmole) of 2-methylthio-1-(4-chlorophenyl)prop-2-enone (Example 171b) 3.8 g of the desired compound, a white solid, mp 185°–186° C., was obtained.

Example 172

N-(4-trifluoromethyl)-3-(4-chlorophenyl)-4-methylsulfonyl-4,5-dihydro-1H-pyrazole-1-carboxamide a: 2-methylsulfonyl-4'-chloroacetophenone To 20 g (100 mmole) of 2-methylthio-4'-chloroacetophenone (Example 171a) in 150 ml of methylene chloride cooled to −20° C. was added 64.8 g (300 mmole) of 35% peracetic acid. The reaction was warmed to room temperature and stirred for 1 hour. A precipitate formed and was filtered to yield the desired compound, a white solid. mp 132°–137° C.

b: N-(4-trifluoromethyl)-3-(4-chlorophenyl)-4-methylsulfonyl-4,5-dihydro-1H-pyrazole-1-carboxamide To a solution of 2.2 g (21.5 mmole) of N,N,N',N'-tetramethyldiaminomethane in 25 ml of methanol and 25 ml of tetrahydrofuran and cooled to −20° C. was added 1.3 g (21.7 mmole) of acetic acid. After 5 minutes 5.0 g (21.5 mmole) of 2-methylsulfonyl-4'-chloroacetophenone (Example 172a) was added dissolved in 15 ml of tetrahydrofuran. The exotherm was controlled to maintain −20° C. throughout the addition. After stirring for 5 minutes, 3.9 g (65 mmole) of acetic acid was added. A precipitate occurred. After another 5 minutes at −20° C., 1.18 g (23.6 mmole) of hydrazine monohydrate was added and the reaction mixture was allowed to stir at room temperature for 18 hours. The mixture was concentrated in vacuo, partitioned between methylene chloride and water, washed with dilute aqueous sodium bicarbonate, and dried over anhydrous magnesium sulfate. To the resulting solution containing 3-(4-chlorophenyl)-4-methylsulfonyl-4,5-dihydro-1H-pyrazole was added 3.5 g (18.7 mmole) of 4-trifluoromethylphenyl isocyanate. After refluxing the resulting mixture for 1 hour, the solvent was concentrated in vacuo and triturated with diethyl ether. The resulting solids were dissolved in hot methyl ethyl ketone and the insolubles were filtered off. Reconcentration and trituration with diethyl ether gave 2.0 g of the desired compound, a light yellow solid, mp 238°–239° C.

Example 237

N-(4-trifluoromethylphenyl)-3-(4-chlorophenyl)-4-(N-methyl-N-cyanoamino)-4,5-dihydro-1H-pyrazole-1-carboxamide To 4.0 g (10 mmole) of N-(4-trifluoromethylphenyl)-3-(4-chlorophenyl)-4-(N-methylamino)-4,5-dihydro-1H-pyrazole-1-carboxamide (Example 116) in 100 ml of methylene chloride was added 10 ml of 1.0M aqueous NaOH and 1.2 g (11.3 mmole) of cyanogen bromide dissolved in 5 ml of methylene chloride. After stirring overnight, the organic layer was separated, concentrated in vacuo, and triturated with diethyl ether to yield the title compound, a white solid, mp 216°–217° C.

Example 70 was prepared following substantially the same procedure.

Example 297

N-(4-trifluoromethoxyphenyl)-3-(4-hydroxyphenyl)-4-(N-methyl-N-(methoxycarbonyl)amino)-4,5-dihydro-1H-pyrazole-1-carboxamide To 25.5 g (50.8 mmole) of N-(4-trifluoromethoxyphenyl)-3-(4-difluoromethoxyphenyl)-4-(N-methyl-N-(methoxycarbonyl)amino)-4,5-dihydro-1H-pyrazole-1-carboxamide (Example 126) dissolved in 25 g of tetrahydrofuran and 25 g of t-butanol was added 10 g of potassium t-butoxide. The mixture was refluxed for 1 hour and an additional 3.5 g of potassium t-butoxide was added. After refluxing an additional hour the mixture was acidified with acetic acid, concentrated in vacuo, and partitioned between methylene chloride and water. The organic layer was dried over anhydrous magnesium sulfate, filtered, concentrated in vacuo, and chromatographed over silica gel using hexane and diethyl ether to yield the title compound, a white solid, mp 228°–233° C.

Example 299

N-(4-trifluoromethoxyphenyl)-3-(4-propoxyphenyl)-4-(N-methyl-N-(methoxycarbonyl)amino)-4,5-dihydro-1H-pyrazole-1-carboxamide To 1.0 g (2.2 mmole) of N-(4-trifluoromethoxyphenyl)-3-(4-hydroxyphenyl)-4-(N-methyl-N-(methoxycarbonyl)amino)-4,5-dihydro-1H-pyrazole-1-carboxamide (Example 297) dissolved in 7.5 ml of dimethylsulfoxide was added 0.35 g (2.8 mmole) of 45% aqueous potassium hydroxide and 1.02 g (6.0 mmole) of 1-iodopropane. The mixture was warmed to 50° C. for 30 minutes and diluted with diethyl ether and water. The organic layer was washed with brine, dried over anhydrous magnesium sulfate, filtered, concentrated in vacuo, and chromatographed over silica gel using hexane and diethyl ether to yield the title compound, a white solid, mp 153°–155° C.

Examples 298 and 300 were prepared following substantially the same procedure and substituting iodoethane or 1-iodobutane for 1-iodopropane.

Example 349

N-(4-trifluoromethylphenyl)-3-(4-chlorophenyl)-4-(N-propyl-N-(2,2,2-trichloroethoxycarbonyl)-amino)-4,5,-dihydro-1H-pyrazole-1-carboxamide a. 2-(N-propyl-N-(2,2,2-trichloroethoxycarbonyl)amino)-4'-chloroacetophenone To 250 ml of methylene chloride was added 180 g (3050 mmole) of 1-aminopropane. The resulting mechanically stirred mixture was cooled to +5° C. (internal) and a solution of 117 g (500 mmole) 4'-chloro-2-bromoacetophenone in 250 ml of methylene chloride was added over 6 minutes while strictly maintaining the internal temperature between +5° C. and +15° C. as a moderate exotherm occurred. Toward the end of the addition, the internal temperature was allowed to rise to +20° C. After the addition was complete, the mixture was stirred at +20° C. for 9 minutes and then rapidly cooled to −5° C. whereon 40 g (500 mmole) of 50% aqueous sodium hydroxide dissolved in 300 ml of water was added. The mixture was transferred to a separatory funnel and the organic layer was separated and thrice washed with 500 ml portions of ice cold water. The organic layer was immediately recooled to −5° C. and a solution of 40 g (500 mmole) of 50% aqueous sodium hydroxide and a solution of 100 g (450 mmole) of 2,2,2-trichloroethyl chloroformate in 100 ml of methylene chloride were simultaneously added with rapid stirring while maintaining the internal temperature between −5° C. and +5° C. After stirring an additional 15 minutes, the organic layer was separated, washed with brine, dried over anhydrous magnesium sulfate, and concentrated in vacuo at 20 torr. The lower boiling impurities were then removed by distillation at 0.2 torr with the bath temperature rising to 200° C. and a head temperature of up to 130° C. The undistilled pot residue was dissolved in 300 ml of diethyl ether and 300 ml of hexane, filtered through silica gel and concentrated in vacuo to yield 120 g of the desired compound, an oil. An analytical sample was isolated by column chromatography on silica gel eluting with diethyl ether and hexanes.

b. 2-(N-propyl-N-(2,2,2-trichloroethoxycarbonyl)amino)-1-(4-chlorophenyl)-prop-2-enone To 118 g (297 mmole) of 2-(N-propyl-N-(2,2,2-trichloroethoxycarbonyl)-amino)-4'-chloroacetophenone (Example 349a) was added 45 g (555 mmole) of 37% formalin, 150 ml of 1-propanol, 8 g (133 mmole) of acetic acid, and 7 g (83 mmole) of piperidine. The resulting mixture was refluxed and followed by TLC. After 90 minutes it was complete. The resulting mixture was cooled, concentrated in vacuo poured into 500 ml of diethyl ether, washed twice with 500 ml of water and once with 200 ml of brine. The organic layer was dried over anhydrous magnesium sulfate and concentrated in vacuo yielding 120 g of the desired compound, an amber oil.

c. 3-(4-chlorophenyl)-4-(N-propyl-N-(2,2,2-trichloroethoxycarbonyl)amino)-4,5-dihydro-1H-pyrazole To 120 g (≦297 mmole) of 2-(N-propyl-N-(2,2,2-trichloroethoxycarbonyl)amino)-1-(4-chlorophenyl)-prop-2-enone (Example 349b) was added 7 g (116 mmole) of acetic acid and 200 ml of methanol. To this mixture was added 22 g (440 mmole) of hydrazine monohydrate. An exotherm occurred. After refluxing for 10 minutes, the solvent was removed in vacuo and the resulting mixture was dissolved in 200 ml of diethyl ether. The organic layer was washed twice with 100 ml portions of water, washed once with 100 ml of brine, and dried over anhydrous magnesium sulfate. The resulting ether solution contained the desired compound and was used as is in the next reaction.

d. N-(4-trifluoromethylphenyl)-3-(4-chlorophenyl)-4-(N-propyl-N-(2,2,2-trichloroethoxycarbonyl)-amino)-4,5-dihydro-1H-pyrazole-1-carboxamide To half of the ether solution of 3-(4-chlorophenyl)-4-(N-propyl-N-(2,2,2-trichloroethoxycarbonyl)-amino)-4,5-dihydro-1H-pyrazole (Example 349c) (≦149 mmole) was added 18.7 g (100 mmole) of 4-trifluoromethylphenyl isocyanate. After stirring for 30 minutes, the mixture was concentrated in vacuo and dissolved in 200 ml of 50/50 diethyl ether/hexanes and cooled to −20° C. Crystals of the desired compound formed and were filtered yielding 30 g of the desired compound, mp 172°–173° C.

Example 350 was prepared following substantially the same procedure and substituting 4-trifluoromethoxyphenyl isocyanate for 4-trifluoromethyphenyl isocyanate.

Example 487

N-(4-trifluoromethoxyphenyl)-3-(4-chlorophenyl)-4-(N-methoxycarbonyl-N-(carbomethoxymethyl)-amino)-4,5,-dihydro-1H-pyrazole-1-carboxamide a. 2-(N-methoxycarbonyl-N-(carbomethoxymethyl)amino)-4'-chloroacetophenone By substantially following the procedure given in Example 585c using 35 g (150 mmole) of 2-bromo-4'-chloroacetophenone, 20.7 g (160 mmole) of glycine methyl ester hydrochloride, 40.6 g (310 mmole) of diisopropylethyl amine, and 14.2 g (150 mmole) of methyl chloroformate, 12.5 g of the desired compound, an oil, was obtained.

b. 2-(N-methoxycarbonyl-N-(carbomethoxymethyl)amino)-1-(4-chlorophenyl)-prop-2-enone By substantially following the procedure given in Example 585d using 12 g (40 mmole) of 2-(N-methoxycarbonyl-N-(carbomethoxymethyl)amino)-4'-chloroacetophenone (Example 487a), 12 g of the desired compound, an oil, was obtained.

c. 3-(4-chlorophenyl)-4-(N-methoxycarbonyl-N-(carbomethoxymethyl)amino)-4,5-dihydro-1H-pyrazole By substantially following the procedure given in Example 585e using 12 g (39 mmole) of 2-(N-methoxycarbonyl-N-(carbomethoxymethyl)amino)-1-(4-chlorophenyl)-prop-2-enone (Example 487b) a solution of the desired compound, which was not further characterized, was obtained.

d. N-(4-trifluoromethylphenyl)-3-(4-chlorophenyl)-4-(N-methoxycarbonyl-N-(carbomethoxymethyl)amino)-4,5-dihydro-1H-pyrazole-1-carboxamide By substantially following the procedure given in Example 585f using one third (≦13 mmole) of the solution of 3-(4-chlorophenyl)-4-(N-methoxycarbonyl-N-(carbomethoxymethyl)amino)-4,5-dihydro-1H-pyrazole (Example 487c) and 1.87 g (10 mmole) of 4-trifluoromethylphenyl isocyanate, 2.5 g of the desired compound, mp 198°–200° C. was obtained.

Examples 486, 488 and 489 were prepared following substantially the same procedure and substituting where appropriate for 4-trifluoromethoxyphenyl isocyanate a compound selected from 4-trifluoromethylphenyl isocyanate or 4-tetrafluoroethoxyphenyl isocyanate.

Example 497

N-(4-trifluoromethylphenyl)-3-(4-propoxyphenyl)-4-carbomethoxymethylamino-4,5-dihydro-1H-pyrazole-1-thiocarboxamide By substantially following the procedure of Example 568 using methyl chloroformate in Step 568a and 4-trifluoromethylphenyl isothiocyanate in Step 568b, the desired compound, mp 167°–169° C., was obtained.

Examples 438 and 439 were prepared following substantially the same procedure, substituting 4-chlorophenyl isothiocyanate for 4-trifluoromethylphenyl isothiocyanate, and substituting 4'-chloroacetophenone for 4'-propoxyacetophenone where appropriate.

Example 498

S-methyl-N-(4-trifluoromethylphenyl)-3-(4-propoxyphenyl)-4-carbomethoxymethylamino-4,5-dihydro-1H-pyrazole-1-isothiocarboxamide A solution of 1.0 g (2.0 mmole) of N-(4-trifluoromethylphenyl)-3-(4-propoxyphenyl)-4-carbomethoxymethylamino-4,5-dihydro-1H-pyrazole-1-thiocarboxamide (Example 497), 3.0 ml (50 mmole) of iodomethane, and 5 ml of methylene chloride was allowed to stand at room temperature for 4 days. The mixture was concentrated in vacuo, dissolved in methylene chloride, washed with dilute aqueous sodium hydroxide, dried over anhydrous magnesium sulfate, concentrated in vacuo, and triturated with diethyl ether and hexanes to give the desired compound, an oil.

Examples 536–539 were prepared following substantially the same procedure and substituting where appropriate for iodomethane a compound selected from iodoethane, 1-iodopropane, 2-iodopropane, or benzyl bromide.

Example 552

N-(4-trifluoromethylphenyl)-3-(4-chlorophenyl)-4-(pyrrolid-2-on-1-yl)-4,5,-dihydro-1H-pyrazole-1-carboxamide To a slurry of 0.14 g (3.5 mmole) of 60% sodium hydride (hexane washed) in 5 ml of dimethylformamide was added 1.8 g (3.0 mmole) of N-(4-trifluoromethylphenyl)-3-(4-chlorophenyl)-4-((4-bromobutyryl)-amino)-4,5,-dihydro-1H-pyrazole-1-carboxamide (Example 549) dissolved in 10 ml of dimethylformamide. Gas was evolved. After stirring at room temperature for 1 hour, the solvent was removed in vacuo, the resulting mixture is dissolved in methylene chloride, washed with water, dried over anhydrous magnesium sulfate, concentrated in vacuo, and triturated with diethyl ether and hexane to yield 1.3 g of the desired compound, mp 216°–217° C.

Examples 546 and 558 were prepared following substantially the same procedure and starting with Examples 543 and 555 respectively.

Examples 553, 547 and 559 were prepared following substantially the same procedure and starting with Examples 550, 544 and 556 respectively.

Examples 554, 548 and 560 were prepared following substantially the same procedure and starting with Examples 551, 545 and 557 respectively.

Example 568

N-(4-trifluoromethylphenyl)-3-(4-propoxyphenyl)-4-(N-methyl-N-(2,2,2-trichloroethoxycarbonyl)amino-4,5,-dihydro-1H-pyrazole-1-carboxamide a. 2-(N-methyl-N-(2,2,2-trichloroethoxycarbonyl)amino)-4'-propoxyacetophenone By substantially following the procedure of Example 349a using 128 g (500 mmole) of 2-bromo-4'-propoxyacetophenone (Example 585b) 150 g of the desired compound, an oil, was obtained.

b. N-(4-trifluoromethylphenyl)-3-(4-propoxyphenyl)-4-(N-methyl-N- (2,2,2-trichloroethoxycarbonyl)amino-4,5,-dihydro-1H-pyrazole-1-carboxamide By substantially following the procedures of Example 585d using 150 g (390 mmole) of 2-(N-methyl-N-(2,2,2-trichloroethoxycarbonyl)amino)-4'-propoxyacetophenone and following with the procedures of Example 585e and Example 585f, 50 g of the desired compound, mp 141°–143° C., was obtained.

Examples 415–418, 471–472, 477, 499–500, 509–511, 513–515, 634, and 659–660 were prepared following substantially the same procedure, substituting where appropriate for 4-trifluoromethylphenyl isocyanate a compound selected from 4-trifluoromethoxyphenyl isocyanate, 4-tetrafluoroethoxyphenyl isocyanate, 4-fluorophenyl isocyanate, 4-chlorophenyl isocyanate, or 4-bromophenyl isocyanate, substituting 4'-butoxyacetophenone for 4'-propoxyacetophenone where appropriate, substituting ethylamine for methylamine where appropriate, and substituting methyl chloroformate for 2,2,2-trichloroethyl chloroformate where appropriate.

Example 570

N-(4-trifluoromethylphenyl)-3-(4-propoxyphenyl)-4-(N-ethyl-N-methylamino)-4,5,-dihydro-1H-pyrazole-1-carboxamide To 1.5 g (3.6 mmole) of N-(4-trifluoromethylphenyl)-3-(4-propoxyphenyl)-4-methylamino-4,5,-dihydro-1H-pyrazole-1-carboxamide (Example 434) dissolved in 10 ml of methanol and 5 ml of tetrahydrofuran was added 0.15 g (2.4 mmole) of sodium cyanoborohydride and 0.2 g (4.3 mmole) of acetaldehyde. To this stirred solution was dropwise added 0.6 g (9.5 mmole) of acetic acid dissolved in 3 ml of methanol. After 30 minutes, the reaction was concentrated in vacuo, dissolved in 50 ml of diethyl ether, washed with water, washed with 1M aqueous sodium hydroxide, washed with brine, dried over anhydrous magnesium sulfate, and concentrated in vacuo. Trituration with diethyl ether and hexanes yielded 1.4 g of the desired compound, mp 130°–132° C.

Examples 569, 571–576, 674–677, 715–726, and 739–742 were prepared following substantially the same procedure, substituting where appropriate for 4-trifluoromethylphenyl isocyanate a compound selected from 4-trifluoromethoxyphenyl isocyanate or 4-tetrafluoroethoxyphenyl isocyanate, substituting where appropriate for 4'-propoxyacetophenone a compound selected from 4'-butoxyacetophenone, 4'-difluoromethoxyacetophenone, 4'-difluoromethoxy-3'-methoxyacetophenone, or 4'-difluoromethoxy-3'-methylacetophenone, substituting ethylamine or propylamine for methylamine where appropriate, substituting where appropriate for acetaldehyde a compound selected from formalin, propionaldehyde, butryaldehyde, isobutyraldehyde, pentanal, hexanal, or benzaldehyde.

Example 585

N-(4-trifluoromethylphenyl)-3-(4-propoxyphenyl)-4-(N-propyl-N-(2,2,2-trichloroethoxycarbonyl)amino)-4,5,-dihydro-1H-pyrazole-1-carboxamide a: 4'-propoxyacetophenone To 500 g (3670 mmole) of 4'-hydroxyacetophenone dissolved in 1000 ml of ethanol was added 450 g (3620 mmole) of 45% aqueous potassium hydroxide. To this mixture was added 650 g (3820 mmole) of 1-iodopropane. The resulting mixture was refluxed for 2 hours, cooled, concentrated in vacuo, and the resulting mixture was dissolved in 1000 ml of diethyl ether and 1000 ml of water. The organic layer was separated, washed with brine adjusted to pH 13 with aqueous sodium hydroxide, dried over anhydrous magnesium sulfate, concentrated in vacuo, and distilled yielding 640 g of the desired compound, bp 110° C. at 0.2 torr.

b. 2-bromo-4'-propoxyacetophenone

To 133 g (750 mmole) of 4'-propoxyacetophenone dissolved in 500 ml of diethyl ether and heated to reflux was dropwise added 120 g (750 mmole) of bromine at a rate to maintain reflux and yet allow decolorization of the red color. The resulting organic solution was twice washed with 500 ml of water, washed once with 200 ml of brine, dried over anhydrous magnesium sulfate, and concentrated in vacuo. This mixture, upon analysis via gas chromatography was approximately 10% unbrominated starting material, 80% the desired monobrominated product, and 10% dibrominated compound. It was used as is in the next reaction. It could be crystallized from diethyl ether and hexane to yield pure monobrominated compound, a solid, mp 36°–38° C.

c. 2-(N-propyl-N-(2,2,2-trichloroethoxycarbonyl)amino)-4'-propoxyacetophenone

To 250 ml of methylene chloride was added 44 g (750 mmole) of 1-aminopropane and 107 g (830 mmole) of N,N-diisopropylethylamine. The resulting mechanically stirred mixture was cooled to +5° C. (internal) and a solution of 2-bromo-4'-propoxyacetophenone (Example 585b) (≦750 mmole) in 250 ml of methylene chloride was added over 6 minutes while strictly maintaining the internal temperature between +5° C. and +15° C. as a moderate exotherm occurred. Toward the end of the addition, the internal temperature was allowed to rise to +20° C. After the addition was complete, the mixture was stirred at +20° C. for 9 minutes and then rapidly cooled to −5° C. whereon a total of 120 g (1500 mmole) of 50% aqueous sodium hydroxide dissolved in 500 ml of water and 159 g (750 mmole) of 2,2,2-trichloroethyl chloroformate were added in alternate aliquots, roughly one eighth of the total for each aliquot, to the stirred reaction mixture. The internal temperature was maintained at between −5° C. and +5° C. during the additions. After stirring an additional 15 minutes, the organic layer was separated, washed with brine, dried over anhydrous magnesium sulfate, and concentrated in vacuo at 20 torr. The lower boiling impurities were then removed by distillation at 0.2 torr with the bath temperature rising to 200° C. and head temperature up to 130° C. The undistilled pot residue was dissolved in 300 ml of diethyl ether and 300 ml of hexane, filtered through silica gel and concentrated in vacuo to yield 123 g of the desired compound, an oil. An analytical sample was isolated by column chromatography on silica gel eluting with diethyl ether and hexanes.

d. 2-(N-propyl-N-(2,2,2-trichloroethoxycarbonyl)amino)-1-(4-propoxyphenyl)-prop-2-enone To 50 g (120 mmole) of 2-(N-propyl-N-(2,2,2-trichloroethoxycarbonyl)amino)-4'-propoxyacetophenone (Example 585c) was added 20 g (240 mmole) of 37% formalin, 20 g of 2-methoxyethanol, 9 g (150 mmole) of acetic acid, and 8.5 g (100 mmole) of piperidine. The resulting mixture was refluxed and followed by TLC. After 1 hour it was complete. The resulting mixture was cooled, poured into 500 ml of diethyl ether, washed twice with 500 ml of water and once with 200 ml of brine. The organic layer was dried over anhydrous magnesium sulfate and concentrated in vacuo yielding 45 g of the desired compound, an amber oil.

e. 3-(4-propoxyphenyl)-4-(N-propyl-N-(2,2,2-trichloroethoxycarbonyl)amino)-4,5-dihydro-1H-pyrazole To 36 g (85 mmole) of 2-(N-propyl-N-(2,2,2-trichloroethoxycarbonyl)amino)-1-(4-propoxyphenyl)-prop-2-enone (Example 585d) was added 1.5 g (25 mmole) of acetic acid and 100 ml of methanol. To this mixture was added 8.5 g (170 mmole) of hydrazine monohydrate. A mild exotherm occurred. After refluxing for 10 minutes, the solvent was removed in vacuo and the resulting mixture was dissolved in 200 ml of diethyl ether. The organic layer was washed twice with 100 ml portions of water, washed once with 100 ml of brine, and dried over anhydrous magnesium sulfate. The resulting ether solution contained the desired compound and was used as is in the next reaction.

f. N-(4-trifluoromethylphenyl)-3-(4-propoxyphenyl)-4-(N-propyl-N-(2,2,2-trichloroethoxycarbonyl)amino)-4,5-dihydro-1H-pyrazole-1-carboxamide To an ether solution of 3-(4-propoxyphenyl)-4-(N-propyl-N-(2,2,2-trichloroethoxycarbonyl)amino)-4,5-dihydro-1H-pyrazole (Example 585e) (≦85 mmole) was added 12.7 g (68 mmole) of 4-trifluoromethylphenyl isocyanate. After stirring for 30 minutes, the mixture was concentrated in vacuo and dissolved in 200 ml of 50/50 diethyl ether/hexanes and cooled to −20° C. Crystals of the desired compound formed and were filtered yielding 23 g of the desired compound, mp 162°–163° C.

Examples 370, 612, 629, 688–690, and 727–729 were prepared following substantially the same procedure, substituting where appropriate for 4-trifluoromethylphenyl isocyanate a compound selected from 4-trifluoromethoxyphenyl isocyanate, or 4-tetrafluoroethoxyphenyl isocyanate, substituting where appropriate for 4'-propoxyacetophenone a compound selected from 4'-chloroacetophenone, 4'-difluoromethoxyacetophenone, 4'-difluoromethoxy-3'-methoxyacetophenone, or 4'-difluoromethoxy-3'-methylacetophenone and substituting where appropriate for methylamine a compound selected from ethylamine, propylamine, or butylamine.

Example 586

N-(4-trifluoromethylphenyl)-3-(4-propoxyphenyl)-4-(N-propylamino)-4,5,-dihydro-1H-pyrazole-1-carboxamide To 22 g (35 mmole) of N-(4-trifluoromethylphenyl)-3-(4-propoxyphenyl)-4-(N-propyl-N-(2,2,2-trichloroethoxycarbonyl)amino)-4,5,-dihydro-1H-pyrazole-1-carboxamide (Example 585) was added 100 ml of tetrahydrofuran, 100 ml of methanol, 4.6 g (70 mmole) of zinc dust, and finally 6.4 g (106 mmole) of acetic acid. After stirring for 2 hours, the starting material had been consumed as shown by TLC. The mixture was filtered from unreacted zinc, concentrated in vacuo, dissolved in 200 ml of diethyl ether, washed twice with 100 ml of water, washed once with 100 ml of dilute aqueous sodium hydroxide and washed once with brine. The resulting ether solution was dried over anhydrous magnesium sulfate, concentrated in vacuo, and chromatographed over silica gel using hexanes, diethyl ether, and ethyl acetate yielding 1 g of N-(4-trifluoromethylphenyl)-3-(4-propoxyphenyl)-4-(N-propyl-N-(2,2-dichloroethoxycarbonyl)-amino)-4,5,-dihydro-1H-pyrazole-1-carboxamide and 12 g of the desired compound, mp 130°–133° C.

Examples 380, 478, 512, 527, 540, 613, 630, 635, 647, 661–662, 691–693, and 730–731 were prepared following substantially the same procedure, substituting where appropriate for 4-trifluoromethylphenyl isocyanate a compound selected from 4-trifluoromethoxyphenyl isocyanate, or 4-tetrafluoroethoxyphenyl isocyanate, substituting where appropriate for 4'-propoxyacetophenone a compound selected from 4'-chloroacetophenone, 4'-butoxyacetophenone, 4'-difluoromethoxyacetophenone, 4'-difluoromethoxy-3'-methoxyacetophenone, or 4'-difluoromethoxy-3'-methylacetophenone and substituting where appropriate for propylamine a compound selected from ethylamine, methylamine, or butylamine.

Examples 419 and 434 were prepared by substantially following the same procedure and starting with Examples 349 and 568 respectively.

Examples 351, 448 and 461 were prepared following substantially the same procedure as for Example 419 and substituting where appropriate for 4-trifluoromethylphenyl isocyanate a compound selected from 4-trifluoromethoxyphenyl isocyanate or 4-tetrafluoroethoxyphenyl isocyanate and substituting where appropriate for n-propylamine a compound selected from methylamine, ethylamine, or n-butylamine.

Example 587

N-(4-trifluoromethylphenyl)-3-(4-propoxyphenyl)-4-(N-formyl-N-propylamino)-4,5,-dihydro-1H-pyrazole-1-carboxamide To 3.0 g (6.7 mmole) of N-(4-trifluoromethylphenyl)-3-(4-propoxyphenyl)-4-(N-propylamino)-4,5,-dihydro-1H-pyrazole-1-carboxamide (Example 586) dissolved in 25 ml of ethyl acetate and cooled to 0° C., was added 2.4 g (30 mmole) of pyridine and 4.0 g (28 mmole) of formic acetic anhydride mixture (Example 621a). After 30 minutes, the reaction mixture was washed with water and brine, concentrated in vacuo, and chromatographed over silica gel using hexanes and ethyl acetate to yield 2.5 g of the desired compound, mp 161°–163° C.

Examples 520, 532, 563, 614, 631, 636, 648, 663, 694, 701, and 708, 732 were prepared following substantially the same procedure, substituting where appropriate for 4-trifluoromethylphenyl isocyanate a compound selected from 4-trifluoromethoxyphenyl isocyanate, or 4-tetrafluoroethoxyphenyl isocyanate, substituting where appropriate for 4'-propoxyacetophenone a compound selected from 4'-chloroacetophenone, 4'-butoxyacetophenone, 4'-difluoromethoxyacetophenone, 4'-difluoromethoxy-3'-methoxyacetophenone, or 4'-difluoromethoxy-3'-methylacetophenone and substituting where appropriate for propylamine a compound selected from ethylamine, methylamine, or butylamine.

Example 423 was prepared by substantially following the same procedure and starting with Example 419.

Examples 355, 384, 451 and 465 were prepared following substantially the same procedure as for Example 423, substituting where appropriate for 4-trifluoromethylphenyl isocyanate a compound selected from 4-trifluoromethoxyphenyl isocyanate or 4-tetrafluoroethoxyphenyl isocyanate and substituting where appropriate for n-propylamine a compound selected from methylamine, ethylamine, or n-butylamine.

Example 590

N-(4-trifluoromethylphenyl)-3-(4-propoxyphenyl)-4-(N-propionyl-N-propylamino)-4,5,-dihydro-1H-pyrazole-1-carboxamide To 2 g (4.5 mmole) of N-(4-trifluoromethylphenyl)-3-(4-propoxyphenyl)-4-(N-propylamino)-4,5,-dihydro-1H-pyrazole-1-carboxamide Example (586) dissolved in 25 ml of ethyl acetate and cooled to −5° C., was added 0.8 g (9 mmole) of pyridine and, finally, 0.8 g (9 mmole) of propionyl chloride was added. After 30 minutes, the reaction mixture was washed with water and brine, concentrated in vacuo, and chromatographed over silica gel using hexanes and ethyl acetate to yield 0.5 g of the desired compound, mp 152°–154° C.

Examples 356–361, 366–369, 375–378, 385–390, 424–429, 430, 436–437, 452–456, 466–470, 474–476, 480–482, 516–517, 521–522, 528–529, 533–534, 564–567, 588–589, 591, 615–618, 637–640, 649–652, 664–667, 695–698, 702–705, 709–712, and 733–736 were prepared following substantially the same procedure, substituting where appropriate for 4-trifluoromethylphenyl isocyanate a compound selected from 4-trifluoromethoxyphenyl isocyanate, or 4-tetrafluoroethoxyphenyl isocyanate, substituting where appropriate for 4'-propoxyacetophenone a compound selected from 4'-chloroacetophenone, 4'-butoxyacetophenone, 4'-difluoromethoxyacetophenone, or 4'-difluoromethoxy-3'-methylacetophenone, substituting where appropriate for propylamine a compound selected from ethylamine, methylamine, or butylamine, and substituting where appropriate for propionyl chloride a compound selected from propionic anhydride, acetic anhydride, acetyl chloride, butyryl chloride, isobutyryl chloride, trifluoroacetic anhydride, methane sulfonyl chloride, valeryl chloride, 2-methylbutyryl chloride, 3-methylbutyryl chloride, or hexanoyl chloride.

Example 592

N-(4-trifluoromethylphenyl)-3-(4-propoxyphenyl)-4-(N-methoxycarbonyl-N-propylamino)-4,5,-dihydro-1H-pyrazole-1-carboxamide To 1.5 g (3.3 mmole) of N-(4-trifluoromethylphenyl)-3-(4-propoxyphenyl)-4-(N-propylamino)-4,5,-dihydro-1H-pyrazole-1-carboxamide Example (586) dissolved in 25 ml of ethyl acetate and cooled to −5° C., was added 1.2 g (15 mmole) of pyridine and, finally, 1.3 g (13 mmole) of methyl chloroformate in 10 ml of ethyl acetate was added over 30 minutes. After an additional 30 minutes, the reaction mixture was washed with water and brine, concentrated in vacuo, and chromatographed over silica gel using hexanes and ethyl acetate to yield 0.7 g of the desired compound, mp 142°–145° C.

Examples 352–354, 381–383, 420–422, 435, 462–464, 473, 479, 518–519, 530–531, 561–562, 593, 619–620, 632–633, 641–642, 653–654, 668–669, 699–700, 706–707, 713–714, and 738–739 were prepared following substantially the same procedure, substituting where appropriate for 4-trifluoromethylphenyl isocyanate a compound selected from 4-trifluoromethoxyphenyl isocyanate, or 4-tetrafluoroethoxyphenyl isocyanate, substituting where appropriate for 4'-propoxyacetophenone a compound from 4'-chloroacetophenone, 4'-butoxyacetophenone, 4'-difluoromethoxyacetophenone, 4'-difluoromethoxy-3'-methoxyacetophenone, or 4'-difluoromethoxy-3'-methylacetophenone, substituting where appropriate for propylamine a compound selected from ethylamine, methylamine, or butylamine and substituting where appropriate for methyl chloroformate a compound selected from ethyl chloroformate, propyl chloroformate, or isopropyl chloroformate.

Example 608

N-(4-trifluoromethylphenyl)-3-(4-propoxyphenyl)-4-(pyrid-2-one-1-yl)-4,5,-dihydro-1H-pyrazole-1-carboxamide a. 2-(pyrid-2-on-1-yl)-4'-propoxyacetophenone To 50 g (≦200 mmole) of 2-bromo-4'-propoxyacetophenone (Example 585b) was added 150 g of tetrahydrofuran, 19.5 g (205 mmole) of 2-hydroxypyridine, and 30 g (233 mmole) of diisopropylethylamine. The reaction mixture was refluxed for 4 hours, concentrated in vacuo, dissolved in 1000 ml of warm ethyl acetate, washed with 300 ml of warm water, washed with brine, dried over anhydrous magnesium sulfate, and concentrated in vacuo. Trituration with diethyl ether and hexanes gave 33.9 g of the desired compound, mp 120°–123° C.

b. 2-(pyrid-2-on-1-yl)-1-(4-propoxyphenyl)-prop-2-enone

To 13.4 g (50 mmole) of 2-(pyrid-2-on-1-yl)-4'-propoxyacetophenone (Example 608a) in 25 ml of dioxane was added 5.0 g (61 mmole) of 37% formalin, 1.0 g (17 mmole) of acetic acid, and 1.0 g (12 mmole) of piperidine. The mixture was refluxed for 4 hours, concentrated in vacuo, dissolved in 200 ml of diethyl ether, washed with water, washed with brine, dried over anhydrous magnesium sulfate, and concentrated in vacuo. Trituration with diethyl ether and hexanes gave 13 g of the desired compound, mp 37°–40° C.

c. N-(4-trifluoromethylphenyl)-3-(4-propoxyphenyl)-4-(pyrid-2-one-1-yl)-4,5,-dihydro-1H-pyrazole-1-carboxamide By substantially following the procedures of Example 585e and Example 585f, using 19 g (67 mmole) of 2-(pyrid-2-on-1-yl)-1-(4-propoxyphenyl)prop-2-enone (Example 608b) one obtains 3.1 g of the desired compound, mp 183°–185° C.

Examples 609–611 and 678–680 were prepared following substantially the same procedure, substituting where appropriate for 4-trifluoromethylphenyl isocyanate a compound selected from 4-trifluoromethoxyphenyl isocyanate, or 4-tetrafluoroethoxyphenyl isocyanate and substituting where appropriate 4-hydroxypyridine for 2-hydroxypyridine.

Example 621

N-(4-trifluoromethylphenyl)-3-(4-propoxyphenyl)-4-(N-formyl-N-(2-methoxyethyl)-amino)-4,5,-dihydro-1H-pyrazole-1-carboxamide a. formic acetic anhydride mixture To 33 ml (350 mmole) of acetic anhydride cooled to 0° C., was added 16 ml (420 mmole) of formic acid while maintaining the internal temperature below +10° C. The mixture was placed in a preheated water bath and maintained at 50° C. for 16 minutes. The mixture was then rapidly cooled to 0° C. and used as is. It contains approximately 7 mmole of formic acetic anhydride per gram.

b. 2-(N-formyl-N-(2-methoxyethyl)amino)-4'-propoxyacetophenone

By substantially following the procedure of Example 585c using 37 g (≦140 mmole) of 2-bromo-4'-propoxyacetophenone (Example 585b), 16 g (210 mmole) of 2-methoxyethylamine, 22 g (170 mmole) of diisopropylethylamine, and 50 g of formic acetic anhydride mixture (≦350 mmole) 18.5 g of the desired compound, an oil, was obtained.

c. 2-(N-formyl-N-(2-methoxyethyl)amino)-1-(4-propoxyphenyl)-prop-2-enone

By substantially following the procedures of Example 585d using 18 g (60 mmole) of 2-(N-formyl-N-(2-methoxyethyl)-amino)-4'-propoxyacetophenone (Example 621b) 15.2 g of the desired compound, an oil, was obtained.

d. 3-(4-propoxyphenyl)-4-(N-formyl-N-(2-methoxyethyl)amino)-4,5-dihydro-1H-pyrazole By substantially following the procedures of Example 585e using 14.7 g (50 mmole) of 2-(N-formyl-N-(2-methoxyethyl)amino)-1-(4-propoxyphenyl)-prop-2-enone (Example 621c) a diethyl ether solution of the desired compound, which was not further characterized, was obtained.

e. N-(4-trifluoromethylphenyl)-3-(4-propoxyphenyl)-4-(N-formyl-N-(2-methoxyethyl)amino)-4,5,-dihydro-1H-pyrazole-1-carboxamide By substantially following the procedures of Example 585f using one quarter of the solution prepared in Example 621d (≦12 mmole) the desired compound, mp 159°–160° C., was obtained.

Examples 483–485, 577–584, 594–601, 622–628, 643–646, 655–658, 670–673, and 684–687 were prepared following substantially the same procedure, substituting where appropriate for 4-trifluoromethylphenyl isocyanate a compound selected 4-trifluoromethoxyphenyl isocyanate, 4-chlorophenyl isocyanate, or 4-tetrafluoroethoxyphenyl isocyanate, substituting where appropriate for 4'-propoxyacetophenone a compound selected from 4'-chloroacetophenone, 4'-butoxyacetophenone, 4'-difluoromethoxyacetophenone, 4'-difluoromethoxy-3'-methoxyacetophenone, or 4'-difluoromethoxy-3'-methylacetophenone, substituting where appropriate for 2-methoxyethylamine a compound selected from methylamine, ethylamine, propylamine, isopropylamine, isobutylamine, allylamine, propargylamine, or 2-cyanoethylamine and substituting where appropriate methyl chloroformate for formic acetic anhydride mixture.

In addition, other examples of this invention can be prepared following substantially the same procedure and substituting for formic acetic anhydride mixture a compound selected from methyl chloroformate, ethyl chloroformate, propyl chloroformate, isopropyl chloroformate, 2,2,2-trichloroethyl chloroformate, di-t-butyl dicarbonate, acetic anhydride, acetyl chloride, propionyl chloride, propionic anhydride, butyryl chloride, isobutyryl chloride, trifluoroacetic anhydride, methane sulfonyl chloride, valeryl chloride, 2-methylbutyryl chloride, 3-methylbutyryl chloride, or hexanoyl chloride.

Example 681

N-(4-trifluoromethylphenyl)-3-(4-propoxyphenyl)-4-(1,2,4-triazol-1-yl)-4,5,-dihydro-1H-pyrazole-1-carboxamide a. 2-(1,2,4-triazol-1-yl)-4'-propoxyacetophenone By substantially following the procedure of Example 608a using 29 g of 2-bromo-4'-propoxyacetophenone (Example 585b), 10 g of 1,2,4-triazole, 15 g (116 mmole) of diisopropylethylamine, and 100 ml of tetrahydrofuran, 8.4 g of the desired compound, mp 97°–99° C., was obtained.

b. 2-(1,2,4-triazol-1-yl)-1-(4-propoxyphenyl)-prop-2-enone

To 7.5 g (30 mmole) of 2-(1,2,4-triazol-1-yl)-4'-propoxyacetophenone (Example 681a) in 30 ml of ethanol was added 3.0 g (37 mmole) of 37% formalin, 0.6 g (10 mmole) of acetic acid, and 0.6 g (7 mmole) of piperidine. The mixture was refluxed for 30 minutes, concentrated in vacuo, dissolved in 100 ml of diethyl ether, washed with water, washed with brine, dried over anhydrous magnesium sulfate, and concentrated in vacuo. Trituration with diethyl ether and hexanes gave 7 g of the desired compound, an oil.

c. N-(4-trifluoromethylphenyl)-3-(4-propoxyphenyl)-4-(1,2,4-triazol-1-yl)-4,5,-dihydro-1H-pyrazole-1-carboxamide By substantially following the procedures of Example 585e and Example 585f, using 7 g (67 mmole) of 2-(1,2,4-triazol-1-yl)-1-(4-propoxyphenyl)-prop-2-enone (Example 681b) 1.3 g of the desired compound, mp 225°–228° C., was obtained.

Examples 682 and 683 were made by substantially the same procedure, substituting where appropriate for 4-trifluoromethylphenyl isocyanate a compound selected from 4-trifluoromethoxyphenyl isocyanate or 4-tetrafluoroethoxyphenyl isocyanate.

On the basis of their strong initial pesticidal activity and excellent residual pesticidal activity, compounds according to the invention may be used in low dosages in controlling pests. The amount of dosage depends on a variety of factors, for example, the substance used, the kind of pest, the formulation used, the state of the crop infested with the pest and the prevailing weather conditions. In general, for the control of pests in agriculture and horticulture, a dosage corresponding to from about 0.1 grams to about 1000 grams of the active substance per hectare may be used and from about 5 grams to about 200 grams per hectare of the active substance is preferred. The exact amount of dosage for a given situation can be routinely determined and depends on a variety of factors, for example, the substance used, the kind of pest, the formulation used, the state of the crop infested with the insect and the prevailing weather conditions.

The term "pesticidal" as employed in the specification and claims of this application is to be construed as any means which adversely affects the existence or growth of the target pest. Such means can compromise a complete killing action, eradication, arresting in growth, inhibition, reducing in number of any combination thereof. The term "control" as employed in the specification and claims of this application is to be construed as meaning "pesticidal" and protecting plants from pest damage. By "pesticidally effective amount" is meant that dosage of active substance sufficient to exert the desired pest "control".

Representative pests which can be controlled by the compounds of the present invention include:

American Cockroach (*Periplaneta americana*)
Bean Leaf Beetle (*Cerotoma trifurcata*)
Bean Leaf Roller (*Urbanus proteus*)
Black Carpenter Ant (*Camponotus pennsylvanicus*)
Black Cutworm (*Agrotis ipsilon*)
Boll Weevil (*Anthonomus grandis grandis*)
Colorado Potato Beetle (*Leptinotarsa decemlineata*)
Fall Armyworm (*Spodoptera frugiperda*)
German Cockroach (*Blattella germanica*)
Green June Beetle (*Cotinis nitida*)
House Cricket (*Acheta domesticus*)
Housefly (*Musca domestica*)
Mexican Bean Beetle (*Epilachna varivestis*)
Potato Leaf Hopper (*Empoasca fabae*)
Red Harvester Ant (*Pogonomyrmex barbatus*)
Red Imported Fire Ant (*Solenopsis invicta*)
Redlegged Grasshopper (*Melanopus femurrubrum*)
Southern Armyworm (*Spodoptera eridania*)
Southern Corn Rootworm (*Diabrotica undecimpunctata howardi*)
Tobacco Budworm (*Heliothis virescens*)

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier is meant any substance which can be used to dissolve, disperse of diffuse the active ingredient in the composition without impairing the active ingredients effectiveness and which by itself has no significant detrimental effect on the soil, equipment, desirable plants, or agronomic environment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. Baits are preparations generally comprising a food or other substance attractive to insects, that includes at least one compound of the instant invention. The invert emulsions are mainly used for air application, where large areas are treated with a comparatively small amount of preparation and may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional pesticide dispersible liquid diluent carriers and/or dispersible solid carriers optionally with the use of carrier vehicle assistants such as conventional pesticide surface-active agents, including emulsifying agents and/or dispersing agents, for example, when water is used as diluent, organic solvents may be added as auxiliary solvents.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001-99% by weight. For compositions suitable for storage or transportation, the amount of active ingredient is preferably between about 0.5-90% by weight, and more preferably between about 1-75% by weight of the mixture. Compositions suitable for direct application or field application generally cintain the active compound in an amount substantially between about 0.0001-95%, preferably between about 0.0005-90% by weight, and more preferably between about 0.001-75% by weight of the mixture.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcoholcellulose derivatives or other colloidal materials, such as casein, to improve the adherence of the pesticide to the surface to be protected.

Compositions and formulations according to the present invention may also include known pesticidal compounds. This expands the spectrum of activity of the preparation and may give rise to synergism.

The following known insecticidal, fungicidal and acaricidal compounds are suitable for use in such a combined preparation such as:

acephate, acethion, acetoxon, aldicarb, aldoxycarb, aldrin, allethrin, allyxycarb, alpha-cypermethrin, amidithion, amitraz, amlure, anethol, azethion, azinphos-ethyl, azinphos-methyl, azocyclotin, bacillus thuringiensis, BCPE, bendiocarb, bensultap, benzoximate, benzyl acetate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chloropropylate, chlorphoxim, chlorpyrifos, chlorpyrifos methyl, chlorthiophos, clofentezine, CPCBS, CPMC, crotoxyphos, crufomate, cryolite, cufraneb, cyanofenphos, cyanophos, cyanthoate, cyfluthrin, cyhexatin, cypermethrin, cyphenothrin, cyromazine, DAEP, DDT, DDVP, deltamethrin, demeton, demeton-S-methyl, demeton-O-methyl, demeton-S, demeton-S-methyl sulfoxid, demephion-O, demephion-S, dialifor, diazinon, dicapthon, dichlofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, d-trans allethrin, endosulfan, endothion, endrin, entice, EPBP, EPN, esfenvalerate, ethiofencarb, ethion, ethoate-methyl, ethoprop, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, flufenoxuron, fluvalinate, fonofos, formetanate hydrochloride, formothion, fosmethilan, fosthietan, furathiocarb, furethrin, grandlure, heptachlor, HETP, hexythiazox, hydramethylnon, hydroprene, IPSP, isazophos, isobenzan, isofenphos, isoprocarb, isoprothiolane, isothioate, isoxathion, jodfenphos, kinoprene, lead arsenate, leptophos, lethane, lindane, lythidathion, malathion, mazidox, mecarbam, mecarphon, menazon, mephosfolan, methamidophos, methidathion, methiocarb, methomyl, methoprene, methoxychlor, methyl parathion, methyl phencapton, mevinphos, mexacarbate, MIPC, mirex, monocrotophos, MTMC, naled, nicotine, nonachlor, omethoate, ovex, oxamyl, oxydeprofs, oxydisulfoton, oxythioquinox, paraoxon, parathion, paris green, permethrin, perthane, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnell, rotenone, ryania, s-bioallethrin, salithion, schradan, sodium fluosilicate, sophamide, sulfotepp, sulprofos, tefluthrin, temephos, TEPP, terbufos, tetrachlorvinphos, tetradifon, tetramethrin, tetrasul, thallium sulfate, thiocarboxime, thiocyclamhydrogenoxalate, thiometon, tolclofos-methyl, toxaphene, triazophos, trichlorfon, trichloronate, triflumuron, trimethacarb, vamidothion, xylylcarb.

Fungicides which can be combined with the insecticides of this invention include:

(a) dithiocarbamate and derivatives such as ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as dinocap, binapacryl, and 2-sec-butyl-4,6-dinitrophenyl isopropyl carbonate;

(c) heterocyclic structures such as captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenasimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, alpha-[2-(4-chlorophenyl)ethyl]-alpha-phenyl-1H-1,2,4-triazole-1-propanenitrile, hexaconazole, cyproconazole, terbuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino] acetamide, fenpropimorph, fenpropidine, 2,6-dimethyl-N-tridecylmorpholine, dodemorph, and triforine;

(d) miscellaneous halogenated fungicides such as chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as griseofulvin, kasugamycin, polyoxin, validamycin, and streptomycin;

(f) copper-based fungicides such as copper hydroxide, cuprous oxide, basic cupric chloride, basic copper carbonate, copper terephthalate, copper naphthenate and Bordeaux mixture; and (g) miscellaneous fungicides such as dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methylisothiocyanate, 1-thiocyano-2,4-dinitrobenzene, 1-phenylthiosemicarbazide, nickel-containing compounds, calciumcyanamide, lime sulfur, thiophanate-methyl, flutolanil, edinophos, isoprothiolane, propenazole, and tricyclazole.

It has been found by biological evaluation that compounds according to the present invention have pesticidal activity and are capable of controlling larvae and adult forms of pests, especially insects from the orders Lepidoptera and Coleoptera. One skilled in the art will know how to determine the activity of a given compound against a given insect and the dosage required to obtain general or selective pesticidal effects. In addition, compounds of the present invention were found active against pyrethroid resistant pests such as the Colorado potato beetle and housefly.

In evaluating the pesticidal activity of the compounds of this invention, the following test procedures were employed.

Evaluations were made on the following insects:

| Common Name | Latin Name |
| --- | --- |
| Mexican Bean Beetle (MBB) | Epilachna varivestis |
| Southern Armyworm (SAW) | Spodoptera eridania |
| Boll Weevil (BW) | Anthonomus grandis grandis |

A test solution containing 600 parts per million (ppm) was made by dissolving the test compound in a solvent (acetone:methanol, 1:1), adding a surfactant and then water to give an acetone:methanol:water system of 5:5:90. A 1:1 mixture of an alkylarylpolyetheralcohol (sold under the trademark Triton® X-155) and a modified phthalic glycerol alkyl resin (sold under the trademark Triton® B-1956) was utilized at the equivalent of 1 ounce per 100 gal. of test solution as a surfactant.

For the bean beetle and armyworm tests, individual bean (Phaseolus limensis var Woods' Prolific) leaves are placed on moistened pieces of filter paper in Petri dishes. The leaves are then sprayed with test solution using a rotating turntable and allowed to dry. The dishes are infested with 10 third instar larvae of Southern armyworm or Mexican bean beetle. The dishes are then covered.

For the boll weevil test ten adult weevils are placed in a 0.5 pint glass Mason jar containing a small cube of apple. The weevils are confined to the jars by fiberglass screen mesh secured by a screw-type rim cap. The jars are then sprayed with the test solution using a rotating turntable, directing the spray through the mesh into the jar.

The percent mortality for the bean beetle, armyworm and boll weevil evaluations are determined 96 hours after treatment. Evaluations are based on a scale of 0–100 percent in which 0 equals no activity and 100 equals total kill.

The rotating turntable consists of a fixed continuously operated spray nozzle under which targets are rotated at a fixed speed and distance. If the target is a Petri dish (such as for the armyworm), the distance from the nozzle is 15 inches. If the target is a Mason jar, the distance between the screened lid and the nozzle is 6 inches (10 inches from the base of the jar to the nozzle). The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Ill.) air atomizing nozzle equipped with a No. 2850 fluid cap and No. 70 air cap. At the 10 psig air pressure used with liquid siphon feed 0.5 GPH (gallons per hour) are delivered in a round spray pattern with a 21° spray angle. Targets are misted with spray droplets to the point that the droplets coalesce to form a uniform thin film insufficient to drown test organisms.

All treatments are maintained at 75°–80° F. under continuous fluorescent light in a well-ventilated room. The results of the initial pesticidal evaluations are given in Table V.

TABLE V

| Compound No. | Biological Evaluations Percent kill at 600 ppm | | |
| --- | --- | --- | --- |
| | Insect Species | | |
| | SAW | MBB | BW |
| 1. | 100 | 100 | 100 |
| 2. | 100 | 100 | 60 |
| 3. | 100 | 100 | 100 |
| 4. | 100 | 100 | 100 |
| 5. | 100 | 100 | 100 |
| 6. | 100 | 100 | 100 |
| 7. | 100 | 100 | 100 |
| 8. | 100 | 100 | 100 |
| 9. | 100 | 100 | 100 |
| 10. | 100 | 100 | 100 |
| 11. | 100 | 100 | 60 |
| 12. | 100 | 100 | 100 |
| 13. | 100 | 100 | 100 |
| 14. | 100 | 100 | 100 |
| 15. | 100 | 100 | 40 |
| 16. | 100 | 100 | 80 |
| 17. | 100 | 100 | 100 |
| 18. | 100 | 100 | 100 |
| 19. | 100 | 100 | 100 |
| 20. | 100 | 100 | 100 |
| 21. | 100 | 100 | 100 |
| 22. | 100 | 100 | 100 |
| 23. | 100 | 100 | 100 |
| 24. | 100 | 100 | 100 |
| 25. | 100 | 100 | 100 |
| 26. | 100 | 100 | 100 |
| 27. | 100 | 100 | 60 |
| 28. | 100 | 100 | 100 |
| 29. | 100 | 100 | 100 |
| 30. | 100 | 100 | 100 |
| 31. | 100 | 100 | 100 |
| 32. | 100 | 100 | 100 |
| 33. | 100 | 100 | 100 |
| 34. | 100 | 100 | 100 |
| 35. | 100 | 100 | 100 |
| 36. | 100 | 100 | 100 |
| 37. | 100 | 100 | 100 |
| 38. | 100 | 100 | 80 |
| 39. | 100 | 100 | 80 |
| 40. | 100 | 100 | 60 |
| 41. | 100 | 100 | 100 |
| 42. | 100 | 100 | 100 |
| 43. | 100 | 100 | 100 |
| 44. | 100 | 100 | 100 |
| 45. | 100 | 100 | 100 |
| 46. | 100 | 100 | 100 |
| 47. | 100 | 100 | 100 |
| 48. | 100 | 100 | 100 |
| 49. | 100 | 100 | 100 |
| 50. | 100 | 100 | 100 |

TABLE V-continued

Biological Evaluations
Percent kill at 600 ppm

| Compound No. | Insect Species | | |
|---|---|---|---|
| | SAW | MBB | BW |
| 51. | 100 | 100 | 40 |
| 52. | 100 | 100 | 100 |
| 53. | 100 | 100 | 100 |
| 54. | 100 | 100 | 80 |
| 55. | 100 | 100 | 80 |
| 56. | 100 | 100 | 100 |
| 57. | 100 | 100 | 100 |
| 58. | 100 | 100 | 100 |
| 59. | 100 | 100 | 100 |
| 60. | 100 | 100 | 100 |
| 61. | 100 | 100 | 100 |
| 62. | 100 | 100 | 80 |
| 63. | 100 | 100 | 100 |
| 64. | 100 | 100 | 100 |
| 65. | 100 | 100 | 100 |
| 66. | 100 | 100 | 100 |
| 67. | 100 | 100 | 100 |
| 68. | 100 | 100 | 100 |
| 69. | 100 | 100 | 100 |
| 70. | 100 | 100 | 100 |
| 71. | 100 | 100 | 100 |
| 72. | 100 | 100 | 100 |
| 73. | 100 | 100 | 100 |
| 74. | 40 | 100 | 100 |
| 75. | 100 | 100 | 60 |
| 76. | 100 | 100 | 100 |
| 77. | 100 | 100 | 80 |
| 78. | 100 | 100 | 100 |
| 79. | 0 | 10 | 20 |
| 80. | 100 | 100 | 100 |
| 81. | 100 | 100 | 100 |
| 82. | 100 | 100 | 100 |
| 83. | 100 | 100 | NT |
| 84. | 100 | 100 | 100 |
| 85. | 100 | 100 | 100 |
| 86. | 100 | 100 | 100 |
| 87. | 100 | 100 | 100 |
| 88. | 100 | 100 | 100 |
| 89. | 100 | 100 | 100 |
| 90. | 100 | 100 | 100 |
| 91. | 90 | 100 | 100 |
| 92. | 100 | 100 | 100 |
| 93. | 90 | 100 | 100 |
| 94. | 0 | 10 | 40 |
| 95. | 100 | 100 | NT |
| 96. | 100 | 100 | NT |
| 97. | 100 | 100 | NT |
| 98. | 100 | 100 | NT |
| 99. | 100 | 100 | NT |
| 100. | 100 | 100 | NT |
| 101. | 70 | 100 | NT |
| 102. | 100 | 100 | NT |
| 103. | 100 | 100 | NT |
| 104. | 100 | 100 | NT |
| 105. | 100 | 100 | NT |
| 105. | 100 | 100 | NT |
| 107. | 100 | 100 | NT |
| 108. | 100 | 100 | NT |
| 109. | 100 | 100 | NT |
| 110. | 100 | 100 | NT |
| 111. | 100 | 100 | NT |
| 112. | 100 | 100 | NT |
| 113. | 100 | 100 | NT |
| 114. | 100 | 100 | NT |
| 115. | 100 | 100 | NT |
| 116. | 100 | 100 | NT |
| 117. | 100 | 100 | NT |
| 118. | 100 | 100 | NT |
| 119. | 100 | 100 | NT |
| 120. | 100 | 100 | NT |
| 121. | 100 | 100 | NT |
| 122. | 100 | 100 | NT |
| 123. | 100 | 100 | NT |
| 124. | 100 | 100 | NT |
| 125. | 100 | 100 | NT |
| 126. | 100 | 100 | NT |
| 127. | 100 | 100 | NT |
| 128. | 100 | 100 | NT |
| 129. | 100 | 100 | NT |
| 130. | 100 | 100 | NT |
| 131. | 100 | 100 | NT |
| 132. | 90 | 50 | NT |
| 133. | 100 | 100 | NT |
| 134. | 100 | 100 | NT |
| 135. | 100 | 100 | NT |
| 136. | 100 | 100 | NT |
| 137. | 100 | 100 | NT |
| 138. | 100 | 100 | NT |
| 139. | 100 | 100 | NT |
| 140. | 100 | 100 | NT |
| 141. | 100 | 100 | NT |
| 142. | 100 | 100 | NT |
| 143. | 100 | 100 | NT |
| 144. | 100 | 100 | NT |
| 145. | 100 | 100 | NT |
| 146. | 100 | 100 | NT |
| 147. | 100 | 100 | NT |
| 148. | 100 | 100 | NT |
| 149. | 100 | 100 | NT |
| 150. | 100 | 100 | NT |
| 151. | 100 | 100 | NT |
| 152. | 100 | 100 | NT |
| 153. | 100 | 100 | NT |
| 154. | 100 | 100 | NT |
| 155. | 100 | 100 | NT |
| 156. | 100 | 50 | NT |
| 157. | 100 | 100 | NT |
| 158. | 100 | 100 | NT |
| 159. | 100 | 100 | NT |
| 160. | 100 | 100 | NT |
| 161. | 100 | 100 | NT |
| 162. | 100 | 100 | NT |
| 163. | 100 | 100 | NT |
| 164. | 100 | 100 | NT |
| 165. | 100 | 100 | NT |
| 166. | 100 | 100 | NT |
| 167. | 100 | 100 | NT |
| 168. | 100 | 100 | NT |
| 169. | 100 | 100 | NT |
| 170. | 100 | 100 | NT |
| 171. | 100 | 100 | NT |
| 172. | 100 | 100 | NT |
| 173. | 100 | 100 | NT |
| 174. | 100 | 100 | NT |
| 175. | 100 | 100 | NT |
| 176. | 100 | 100 | NT |
| 177. | 100 | 100 | NT |
| 178. | 100 | 100 | NT |
| 179. | 100 | 100 | NT |
| 180. | 100 | 100 | NT |
| 181. | 100 | 100 | NT |
| 182. | 100 | 100 | NT |
| 183. | 100 | 100 | NT |
| 184. | 100 | 100 | NT |
| 185. | 100 | 100 | NT |
| 186. | 100 | 100 | NT |
| 187. | 100 | 100 | NT |
| 188. | 100 | 100 | NT |
| 189. | 100 | 100 | NT |
| 190. | 100 | 100 | NT |
| 191. | 100 | 100 | NT |
| 192. | 100 | 100 | NT |
| 193. | 100 | 100 | NT |
| 194. | 100 | 100 | NT |

TABLE V-continued

Biological Evaluations
Percent kill at 600 ppm

| Compound No. | Insect Species | | |
|---|---|---|---|
| | SAW | MBB | BW |
| 195. | 100 | 100 | NT |
| 196. | 100 | 100 | NT |
| 197. | 100 | 100 | NT |
| 199. | 100 | 100 | NT |
| 200. | 100 | 100 | NT |
| 201. | 100 | 100 | NT |
| 202. | 100 | 100 | NT |
| 203. | 100 | 100 | NT |
| 204. | 100 | 100 | NT |
| 205. | 100 | 100 | NT |
| 206. | 90 | 100 | NT |
| 207. | 100 | 100 | NT |
| 208. | 100 | 100 | NT |
| 209. | 100 | 100 | NT |
| 210. | 100 | 100 | NT |
| 211. | 100 | 100 | NT |
| 212. | 100 | 100 | NT |
| 213. | 100 | 100 | NT |
| 214. | 100 | 100 | NT |
| 215. | 100 | 100 | NT |
| 216. | 40 | 100 | NT |
| 217. | 50 | 80 | NT |
| 218. | 100 | 100 | NT |
| 219. | 100 | 100 | NT |
| 220. | 100 | 100 | NT |
| 221. | 100 | 100 | NT |
| 222. | 100 | 100 | NT |
| 223. | 100 | 100 | NT |
| 224. | 100 | 100 | NT |
| 225. | 100 | 100 | NT |
| 226. | 100 | 100 | NT |
| 227. | 100 | 100 | NT |
| 228. | 100 | 100 | NT |
| 229. | 100 | 100 | NT |
| 230. | 100 | 100 | NT |
| 231. | 100 | 100 | NT |
| 232. | 100 | 100 | NT |
| 233. | 100 | 100 | NT |
| 234. | 100 | 100 | NT |
| 235. | 100 | 100 | NT |
| 236. | 100 | 100 | NT |
| 237. | 100 | 100 | NT |
| 238. | 100 | 100 | NT |
| 239. | 100 | 100 | NT |
| 240. | 100 | 100 | NT |
| 241. | 100 | 100 | NT |
| 242. | 100 | 100 | NT |
| 243. | 100 | 100 | NT |
| 244. | 100 | 100 | NT |
| 245. | 0 | 100 | NT |
| 246. | 100 | 100 | NT |
| 247. | 100 | 100 | NT |
| 248. | 100 | 100 | NT |
| 249. | 100 | 100 | NT |
| 250. | 100 | 100 | NT |
| 251. | 100 | 100 | NT |
| 252. | 100 | 100 | NT |
| 253. | 100 | 100 | NT |
| 254. | 100 | 100 | NT |
| 255. | 100 | 100 | NT |
| 256. | 100 | 100 | NT |
| 257. | 100 | 100 | NT |
| 258. | 100 | 100 | NT |
| 259. | 100 | 100 | NT |
| 260. | 100 | 100 | NT |
| 261. | 100 | 100 | NT |
| 262. | 100 | 100 | NT |
| 263. | 100 | 100 | NT |
| 264. | 100 | 100 | NT |
| 265. | 100 | 100 | NT |
| 266. | 100 | 100 | NT |
| 267. | 100 | 100 | NT |
| 268. | 100 | 100 | NT |
| 269. | 100 | 100 | NT |
| 270. | 100 | 100 | NT |
| 271. | 100 | 100 | NT |
| 272. | 20 | 100 | NT |
| 273. | 100 | 100 | NT |
| 274. | 0 | 100 | NT |
| 275. | 100 | 100 | NT |
| 276. | 100 | 100 | NT |
| 277. | 100 | 100 | NT |
| 278. | 100 | 100 | NT |
| 279. | 100 | 100 | NT |
| 280. | 100 | 100 | NT |
| 281. | 100 | 100 | NT |
| 282. | 100 | 100 | NT |
| 283. | 100 | 100 | NT |
| 284. | 100 | 100 | NT |
| 285. | 100 | 100 | NT |
| 286. | 100 | 100 | NT |
| 287. | 100 | 100 | NT |
| 288. | 100 | 100 | NT |
| 289. | 100 | 100 | NT |
| 290. | 40 | 100 | NT |
| 291. | 100 | 100 | NT |
| 292. | 100 | 100 | NT |
| 293. | 100 | 100 | NT |
| 294. | 100 | 100 | NT |
| 295. | 100 | 100 | NT |
| 296. | 100 | 100 | NT |
| 297. | 100 | 100 | NT |
| 298. | 100 | 100 | NT |
| 299. | 100 | 100 | NT |
| 300. | 100 | 100 | NT |
| 301. | 70 | 100 | NT |
| 302. | 100 | 100 | NT |
| 303. | 100 | 100 | NT |
| 304. | 0 | 100 | NT |
| 305. | 100 | 100 | NT |
| 306. | 100 | 100 | NT |
| 307. | 100 | 100 | NT |
| 308. | 100 | 100 | NT |
| 309. | 100 | 100 | NT |
| 310. | 100 | 100 | NT |
| 311. | 100 | 100 | NT |
| 312. | 100 | 100 | NT |
| 313. | 10 | 50 | NT |
| 314. | 100 | 100 | NT |
| 315. | 100 | 100 | NT |
| 316. | 100 | 100 | NT |
| 317. | 0 | 100 | NT |
| 318. | 0 | 100 | NT |
| 319. | 100 | 100 | NT |
| 320. | 10 | 100 | NT |
| 321. | 100 | 100 | NT |
| 322. | 0 | 100 | NT |
| 323. | 0 | 100 | NT |
| 324. | 0 | 100 | NT |
| 325. | 100 | 100 | NT |
| 326. | 100 | 100 | NT |
| 327. | 100 | 100 | NT |
| 328. | 100 | 100 | NT |
| 329. | 100 | 100 | NT |
| 330. | 100 | 100 | NT |
| 331. | 100 | 100 | NT |
| 332. | 100 | 100 | NT |
| 333. | 100 | 100 | NT |
| 334. | 100 | 100 | NT |
| 335. | 100 | 100 | NT |
| 336. | 100 | 100 | NT |
| 337. | 100 | 100 | NT |
| 338. | 100 | 100 | NT |
| 339. | 100 | 100 | NT |

TABLE V-continued

Biological Evaluations
Percent kill at 600 ppm

| Compound No. | Insect Species | | |
|---|---|---|---|
| | SAW | MBB | BW |
| 340. | 100 | 100 | NT |
| 341. | 100 | 100 | NT |
| 342. | 100 | 100 | NT |
| 343. | 100 | 100 | NT |
| 344. | 100 | 100 | NT |
| 345. | 100 | 100 | NT |
| 346. | 100 | 100 | NT |
| 347. | 100 | 100 | NT |
| 348. | 100 | 100 | NT |
| 349. | 100 | 100 | NT |
| 350. | 100 | 0 | NT |
| 351. | 100 | 100 | NT |
| 352. | 100 | 100 | NT |
| 353. | 100 | 100 | NT |
| 354. | 100 | 100 | NT |
| 355. | 100 | 100 | NT |
| 356. | 100 | 100 | NT |
| 357. | 100 | 100 | NT |
| 358. | 100 | 100 | NT |
| 359. | 100 | 100 | NT |
| 360. | 100 | 100 | NT |
| 361. | 100 | 100 | NT |
| 362. | 100 | 100 | NT |
| 363. | 100 | 100 | NT |
| 364. | 100 | 100 | NT |
| 365. | 100 | 100 | NT |
| 366. | 100 | 100 | NT |
| 367. | 100 | 100 | NT |
| 368. | 100 | 100 | NT |
| 369. | 100 | 100 | NT |
| 370. | 0 | 20 | NT |
| 371. | 100 | 100 | NT |
| 372. | 100 | 100 | NT |
| 373. | 100 | 100 | NT |
| 374. | 0 | 100 | NT |
| 375. | 100 | 100 | NT |
| 376. | 100 | 100 | NT |
| 377. | 100 | 100 | NT |
| 378. | 100 | 100 | NT |
| 379. | 100 | 100 | NT |
| 380. | 100 | 100 | NT |
| 381. | 100 | 100 | NT |
| 382. | 100 | 100 | NT |
| 383. | 0 | 20 | NT |
| 384. | 100 | 100 | NT |
| 385. | 100 | 100 | NT |
| 386. | 100 | 100 | NT |
| 387. | 100 | 100 | NT |
| 388. | 100 | 100 | NT |
| 389. | 100 | 100 | NT |
| 390. | 100 | 100 | NT |
| 391. | 100 | 100 | NT |
| 392. | 100 | 100 | NT |
| 393. | 100 | 100 | NT |
| 394. | 100 | 100 | NT |
| 395. | 100 | 100 | NT |
| 396. | 100 | 100 | NT |
| 397. | 100 | 100 | NT |
| 398. | 100 | 100 | NT |
| 399. | 100 | 100 | NT |
| 400. | 100 | 100 | NT |
| 401. | 100 | 100 | NT |
| 402. | 100 | 100 | NT |
| 403. | 100 | 100 | NT |
| 404. | 100 | 100 | NT |
| 405. | 100 | 100 | NT |
| 406. | 100 | 100 | NT |
| 407. | 100 | 100 | NT |
| 408. | 100 | 100 | NT |
| 409. | 100 | 100 | NT |
| 410. | 100 | 100 | NT |
| 411. | 100 | 100 | NT |
| 412. | 100 | 100 | NT |
| 413. | 100 | 100 | NT |
| 414. | 100 | 100 | NT |
| 415. | 100 | 100 | NT |
| 416. | 100 | 100 | NT |
| 417. | 100 | 100 | NT |
| 418. | 100 | 100 | NT |
| 419. | 100 | 100 | NT |
| 420. | 100 | 100 | NT |
| 421. | 100 | 100 | NT |
| 422. | 60 | 100 | NT |
| 423. | 100 | 100 | NT |
| 424. | 100 | 100 | NT |
| 425. | 100 | 100 | NT |
| 426. | 100 | 100 | NT |
| 427. | 100 | 100 | NT |
| 428. | 100 | 100 | NT |
| 429. | 100 | 100 | NT |
| 430. | 100 | 100 | NT |
| 431. | 100 | 100 | NT |
| 432. | 0 | 40 | NT |
| 433. | 100 | 100 | NT |
| 434. | 100 | 100 | NT |
| 435. | 100 | 100 | NT |
| 436. | 100 | 100 | NT |
| 437. | 100 | 100 | NT |
| 438. | 100 | 100 | NT |
| 439. | 100 | 100 | NT |
| 440. | 100 | 100 | NT |
| 441. | 100 | 100 | NT |
| 442. | 10 | 100 | NT |
| 443. | 0 | 0 | NT |
| 444. | 100 | 100 | NT |
| 445. | 100 | 100 | NT |
| 446. | 100 | 100 | NT |
| 447. | 100 | 100 | NT |
| 448. | 100 | 100 | NT |
| 449. | 100 | 100 | NT |
| 450. | 100 | 100 | NT |
| 451. | 100 | 100 | NT |
| 452. | 100 | 100 | NT |
| 453. | 100 | 100 | NT |
| 454. | 0 | 100 | NT |
| 455. | 100 | 100 | NT |
| 456. | 100 | 100 | NT |
| 457. | 100 | 100 | NT |
| 458. | 100 | 100 | NT |
| 459. | 100 | 100 | NT |
| 460. | 100 | 100 | NT |
| 461. | 100 | 100 | NT |
| 462. | 100 | 100 | NT |
| 463. | 100 | 100 | NT |
| 464. | 100 | 100 | NT |
| 465. | 100 | 100 | NT |
| 466. | 100 | 100 | NT |
| 467. | 100 | 100 | NT |
| 468. | 0 | 100 | NT |
| 469. | 100 | 100 | NT |
| 470. | 100 | 100 | NT |
| 471. | 100 | 100 | NT |
| 472. | 100 | 100 | NT |
| 473. | 100 | 100 | NT |
| 474. | 100 | 100 | NT |
| 475. | 100 | 100 | NT |
| 476. | 100 | 100 | NT |
| 477. | 100 | 100 | NT |
| 478. | 100 | 100 | NT |
| 479. | 100 | 100 | NT |
| 480. | 100 | 100 | NT |
| 481. | 100 | 100 | NT |
| 482. | 100 | 100 | NT |
| 483. | 100 | 100 | NT |

TABLE V-continued

Biological Evaluations
Percent kill at 600 ppm

| Compound No. | Insect Species | | |
|---|---|---|---|
| | SAW | MBB | BW |
| 484. | 100 | 100 | NT |
| 485. | 100 | 100 | NT |
| 486. | 100 | 100 | NT |
| 487. | 100 | 100 | NT |
| 488. | 100 | 100 | NT |
| 489. | 100 | 0 | NT |
| 490. | 100 | 100 | NT |
| 491. | 100 | 100 | NT |
| 492. | 100 | 100 | NT |
| 493. | 100 | 100 | NT |
| 494. | 100 | 100 | NT |
| 495. | 100 | 100 | NT |
| 496. | 100 | 100 | NT |
| 497. | 100 | 100 | NT |
| 498. | 100 | 100 | NT |
| 499. | 100 | 100 | NT |
| 500. | 100 | 100 | NT |
| 501. | 100 | NT | NT |
| 502. | 100 | NT | NT |
| 503. | 100 | NT | NT |
| 504. | 100 | NT | NT |
| 505. | 100 | NT | NT |
| 506. | 100 | NT | NT |
| 507. | 100 | NT | NT |
| 508. | 100 | NT | NT |
| 509. | 100 | 0 | NT |
| 510. | 100 | 100 | NT |
| 511. | 0 | 0 | NT |
| 512. | 100 | 100 | NT |
| 513. | 100 | 100 | NT |
| 514. | 100 | 100 | NT |
| 515. | 100 | 100 | NT |
| 516. | 100 | 100 | NT |
| 517. | 100 | 100 | NT |
| 518. | 100 | 100 | NT |
| 519. | 100 | 100 | NT |
| 520. | 100 | 100 | NT |
| 521. | 100 | 100 | NT |
| 522. | 100 | 100 | NT |
| 523. | 100 | NT | NT |
| 524. | 100 | NT | NT |
| 525. | 100 | NT | NT |
| 526. | 100 | NT | NT |
| 527. | 100 | 100 | NT |
| 528. | 100 | 100 | NT |
| 529. | 100 | 100 | NT |
| 530. | 100 | 100 | NT |
| 531. | 100 | 100 | NT |
| 532. | 100 | 100 | NT |
| 533. | 100 | 100 | NT |
| 534. | 100 | 100 | NT |
| 535. | 100 | 100 | NT |
| 536. | 100 | 100 | NT |
| 537. | 100 | 100 | NT |
| 538. | 100 | 100 | NT |
| 539. | 100 | 100 | NT |
| 540. | 100 | 100 | NT |
| 541. | 100 | 100 | NT |
| 542. | 80 | 0 | NT |
| 543. | 80 | 100 | NT |
| 544. | 0 | 100 | NT |
| 545. | 40 | 100 | NT |
| 546. | 100 | 100 | NT |
| 547. | 100 | 100 | NT |
| 548. | 100 | 100 | NT |
| 549. | 80 | 100 | NT |
| 550. | 0 | 20 | NT |
| 551. | 1D0 | 100 | NT |
| 552. | 100 | 100 | NT |
| 553. | 100 | 100 | NT |
| 554. | 100 | 100 | NT |
| 555. | 100 | 100 | NT |
| 556. | 0 | 100 | NT |
| 557. | 100 | 100 | NT |
| 558. | 100 | 100 | NT |
| 559. | 100 | 100 | NT |
| 560. | 100 | 100 | NT |
| 561. | 100 | 100 | NT |
| 562. | 100 | 100 | NT |
| 563. | 100 | 100 | NT |
| 564. | 100 | 100 | NT |
| 565. | 100 | 100 | NT |
| 566. | 100 | 100 | NT |
| 567. | 100 | 100 | NT |
| 568. | 100 | 100 | NT |
| 569. | 100 | 100 | NT |
| 570. | 100 | 100 | NT |
| 571. | 100 | 100 | NT |
| 572. | 100 | 100 | NT |
| 573. | 100 | 100 | NT |
| 574. | 100 | 100 | NT |
| 575. | 40 | 100 | NT |
| 576. | 80 | 100 | NT |
| 577. | 0 | 100 | NT |
| 578. | 100 | 100 | NT |
| 579. | 100 | 100 | NT |
| 580. | 0 | 0 | NT |
| 581. | 100 | 100 | NT |
| 582. | 100 | 100 | NT |
| 583. | 100 | 100 | NT |
| 584. | 100 | 0 | NT |
| 585. | 100 | 0 | NT |
| 586. | 100 | 100 | NT |
| 587. | 100 | 100 | NT |
| 588. | 100 | 100 | NT |
| 589. | .100 | 100 | NT |
| 590. | 100 | 100 | NT |
| 591. | 100 | 100 | NT |
| 592. | 100 | 100 | NT |
| 593. | 100 | 100 | NT |
| 594. | 100 | 100 | NT |
| 595. | 100 | 100 | NT |
| 596. | 100 | 100 | NT |
| 597 | 100 | 100 | NT |
| 598. | 100 | 100 | NT |
| 599. | 100 | 100 | NT |
| 600. | 100 | 100 | NT |
| 601. | 100 | 100 | NT |
| 602. | 100 | NT | NT |
| 603. | 100 | NT | NT |
| 604. | 100 | NT | NT |
| 605. | 100 | NT | NT |
| 606. | 100 | NT | NT |
| 607. | 100 | NT | NT |
| 608. | 100 | 100 | NT |
| 609. | 100 | 100 | NT |
| 610. | 100 | 100 | NT |
| 611. | 100 | 100 | NT |
| 612. | 80 | 0 | NT |
| 613. | 100 | 100 | NT |
| 614. | 100 | 100 | NT |
| 615. | 100 | 100 | NT |
| 616. | 100 | 100 | NT |
| 617. | 100 | 100 | NT |
| 618. | 100 | 100 | NT |
| 619. | 100 | 100 | NT |
| 620. | 100 | 100 | NT |
| 621. | 100 | 100 | NT |
| 622. | 100 | 100 | NT |
| 623. | 100 | 100 | NT |
| 624. | 100 | 100 | NT |
| 625. | 100 | 100 | NT |
| 626. | 100 | 100 | NT |
| 627. | 100 | 100 | NT |

TABLE V-continued

Biological Evaluations
Percent kill at 600 ppm

| Compound No. | Insect Species | | |
|---|---|---|---|
| | SAW | MBB | BW |
| 628. | 100 | 100 | NT |
| 629. | 0 | 40 | NT |
| 630. | 100 | 100 | NT |
| 631. | 100 | 100 | NT |
| 632. | 100 | 100 | NT |
| 633. | 100 | 100 | NT |
| 634. | 0 | 40 | NT |
| 635. | 100 | 100 | NT |
| 636. | 100 | 100 | NT |
| 637. | 100 | 100 | NT |
| 638. | 80 | 100 | NT |
| 639. | 100 | 100 | NT |
| 640. | 100 | 100 | NT |
| 641. | 100 | 100 | NT |
| 642. | 100 | 100 | NT |
| 643. | 100 | 100 | NT |
| 644. | 100 | 100 | NT |
| 645. | 100 | 100 | NT |
| 646. | 100 | 100 | NT |
| 647. | 100 | 100 | NT |
| 648. | 100 | 100 | NT |
| 649. | 100 | 100 | NT |
| 650. | 100 | 100 | NT |
| 651. | 100 | 100 | NT |
| 652. | 100 | 100 | NT |
| 653. | 100 | 100 | NT |
| 654. | 100 | 100 | NT |
| 655. | 100 | 100 | NT |
| 656. | 100 | 100 | NT |
| 657. | 100 | 100 | NT |
| 658. | 100 | 100 | NT |
| 659. | 0 | 100 | NT |
| 660. | 70 | 0 | NT |
| 661. | 100 | 100 | NT |
| 662. | 100 | 100 | NT |
| 663. | 100 | 100 | NT |
| 664. | 100 | 100 | NT |
| 665. | 100 | 100 | NT |
| 666. | 100 | 100 | NT |
| 667. | 100 | 100 | NT |
| 668. | 100 | 100 | NT |
| 669. | 100 | 100 | NT |
| 670. | 70 | 100 | NT |
| 671. | 100 | 100 | NT |
| 672. | 100 | 100 | NT |
| 673. | 100 | 100 | NT |
| 674. | 100 | 100 | NT |
| 675. | 100 | 100 | NT |
| 676. | 100 | 100 | NT |
| 677. | 100 | 100 | NT |
| 678. | 100 | 100 | NT |
| 679. | 100 | 100 | NT |
| 680. | 100 | 100 | NT |
| 681. | 100 | 100 | NT |
| 682. | 100 | 100 | NT |
| 683. | 100 | 100 | NT |
| 684. | 100 | 100 | NT |
| 685. | 100 | 100 | NT |
| 686. | 100 | 100 | NT |
| 687. | 100 | 100 | NT |
| 688. | 100 | 100 | NT |
| 689. | 100 | 100 | NT |
| 690. | 100 | 100 | NT |
| 691. | 100 | 100 | NT |
| 692. | 100 | 100 | NT |
| 693. | 100 | 100 | NT |
| 694. | 100 | 100 | NT |
| 695. | 100 | 100 | NT |
| 696. | 100 | 100 | NT |
| 697. | 100 | 100 | NT |
| 698. | 100 | 100 | NT |
| 699. | 100 | 100 | NT |
| 700. | 100 | 100 | NT |
| 701. | 100 | 100 | NT |
| 702. | 100 | 100 | NT |
| 703. | 100 | 100 | NT |
| 704. | 100 | 100 | NT |
| 705. | 100 | 100 | NT |
| 706. | 100 | 100 | NT |
| 707. | 100 | 100 | NT |
| 708. | 100 | 100 | NT |
| 709. | 100 | 100 | NT |
| 710. | 100 | 100 | NT |
| 711. | 100 | 100 | NT |
| 712. | 100 | 100 | NT |
| 713. | 100 | 100 | NT |
| 714. | 100 | 100 | NT |
| 715. | 100 | 100 | NT |
| 716. | 100 | 100 | NT |
| 717. | 100 | 100 | NT |
| 718. | 100 | 100 | NT |
| 719. | 100 | 100 | NT |
| 720. | 100 | 100 | NT |
| 721. | 100 | 100 | NT |
| 722. | 100 | 100 | NT |
| 723. | 100 | 100 | NT |
| 724. | 100 | NT | NT |
| 725. | 100 | NT | NT |
| 726. | 100 | NT | NT |
| 727. | 100 | NT | NT |
| 728. | 100 | NT | NT |
| 729. | 100 | NT | NT |
| 730. | 100 | NT | NT |
| 731. | 100 | NT | NT |
| 732. | 100 | NT | NT |
| 733. | 100 | NT | NT |
| 734. | 100 | NT | NT |
| 735. | 100 | NT | NT |
| 736. | 100 | NT | NT |
| 737. | 100 | NT | NT |
| 738. | 100 | NT | NT |
| 739. | 100 | NT | NT |
| 740. | 100 | NT | NT |
| 741. | 100 | NT | NT |
| 742. | 100 | NT | NT |

= Not Tested

It is to be understood that changes and variations may be made without departing from the spirit and scope of the invention as defined by the appended claims.

I claim:

1. A compound of the formula

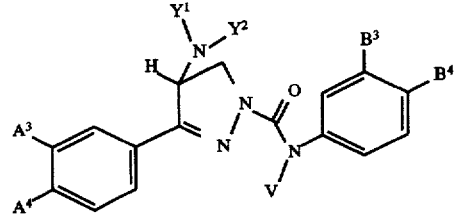

wherein $A^3$ and $A^4$ are each independently a hydrogen atom, alkyl, halo, haloalkyl, polyhaloalkyl, alkoxy, haloalkoxy, polyhaloalkoxy, alkoxyalkoxy, alkoxycarbonyl or nitro;

$B^3$ is a hydrogen atom, halo, haloalkyl, polyhaloalkyl, haloalkoxy or polyhaloalkoxy;

$B^4$ is halo, haloalkyl, polyhaloalkyl, haloalkoxy or polyhaloalkoxy;

V is a hydrogen atom, alkyl, alkylcarbonyl, alkoxycarbonyl or formyl;

$Y^1$ is a hydrogen atom, alkyl, alkenyl, alkynyl, phenyl, halophenyl, alkoxyalkyl, alkoxycarbonylalkyl or cyanoalkyl;

$Y^2$ is a hydrogen atom, alkyl, alkoxycarbonyl, phenalkoxycarbonyl, phenoxycarbonyl, haloalkoxycarbonyl, polyhaloalkoxycarbonyl, alkoxyalkoxycarbonyl, alkenyloxycarbonyl, alkynyloxycarbonyl, formyl, alkylcarbonyl, haloalkylcarbonyl, polyhaloalkylcarbonyl, benzoyl, alkenylcarbonyl, polyhaloalkenylcarbonyl, alkylcarbonylcarbonyl, alkoxycarbonylcarbonyl, alkylthiocarbonyl, alkylsulfonyl, phenylsulfonyl, halophenylsulfonyl, phenylaminocarbonyl, polyhaloalkoxyphenylaminocarbonyl, cyano, monoalkylaminocarbonyl or dialkylaminocarbonyl, dialkylphosphoryl or dialkylthiophosphoryl wherein the alkyl groups are the same or different; or agronomically acceptable salt thereof.

2. The compound of claim 1 wherein $A^3$ and $A^4$ are each independently a hydrogen atom, ($C_1$-$C_6$)alkyl, fluoro, chloro, bromo, polyhalo($C_1$-$C_2$) alkyl wherein the halo is independently selected from fluoro, chloro and bromo, ($C_1$-$C_6$)alkoxy, polyhalo ($C_1$-$C_4$)alkoxy wherein the halo is independently selected from fluoro, chloro and bromo, ($C_1$-$C_2$)alkoxy ($C_1$-$C_6$)alkoxy, ($C_1$-$C_4$)alkoxycarbonyl or nitro;

$B^3$ is a hydrogen atom, chloro, fluoro, bromo, polyhalo ($C_1$-$C_2$)alkyl wherein the halo is independently selected from fluoro, chloro and bromo, or polyhalo ($C_1$-$C_4$)alkoxy wherein the halo is independently selected from fluoro, chloro and bromo;

$B^4$ is chloro, bromo, polyhalo($C_1$-$C_2$)alkyl wherein the halo is independently selected from fluoro, chloro and bromo, or polyhalo($C_1$-$C_4$)alkoxy wherein the halo is independently selected from fluoro, chloro and bromo;

V is a hydrogen atom, ($C_1$-$C_2$)alkyl, ($C_1$-$C_2$) alkylcarbonyl, ($C_1$-$C_2$)alkoxycarbonyl or formyl;

$Y^1$ is a hydrogen atom, ($C_1$-$C_6$)alkyl, ($C_2$-$C_4$)alkenyl, ($C_2$-$C_4$)alkynyl, phenyl, 4-halophenyl, ($C_1$-$C_4$)alkoxy ($C_1$-$C_4$)alkyl or cyano($C_1$-$C_3$)alkyl; and $Y^2$ is a hydrogen atom, ($C_1$-$C_6$)alkyl, ($C_1$-$C_6$) alkoxycarbonyl, phen($C_1$-$C_2$)alkoxycarbonyl, phenoxycarbonyl, halo($C_1$-$C_4$)alkoxycarbonyl wherein the halo is independently selected from fluoro, chloro and bromo, polyhalo($C_1$-$C_3$)alkoxycarbonyl wherein the halo is independently selected from fluoro, chloro and bromo, ($C_1$-$C_2$)alkoxy($C_1$-$C_3$) alkoxycarbonyl, ($C_2$-$C_4$)alkenyloxycarbonyl, ($C_2$-$C_4$) alkynyloxycarbonyl, formyl, ($C_1$-$C_6$)alkylcarbonyl, polyhalo($C_1$-$C_2$)alkylcarbonyl wherein the halo is independently selected from fluoro, chloro and bromo, benzoyl, ($C_2$-$C_4$)alkenylcarbonyl, polyhalo($C_2$-$C_4$) alkenylcarbonyl, ($C_1$-$C_2$)alkylcarbonylcarbonyl, ($C_1$-$C_3$)alkylthiocarbonyl, ($C_1$—$C_3$)alkylsulfonyl, phenylsulfonyl, 4-halophenylsulfonyl, phenylaminocarbonyl, 4-(polyhalo($C_1$-$C_2$)alkoxy) phenylaminocarbonyl, cyano, mono($C_1$-$C_2$) alkylaminocarbonyl or di($C_{1-2}$)alkylaminocarbonyl, di($C_1$-$C_2$)alkylphosphoryl or di($C_1$-$C_2$) alkylthiophosphoryl wherein the alkyl groups are the same or different.

3. The compound of claim 2 wherein $A^3$ and $A^4$ are each independently a hydrogen atom, methyl, ethyl, n-propyl, n-butyl, fluoro, chloro, bromo, trifluoromethyl, methoxy, ethoxy, n-propoxy, n-butoxy, trifluoromethoxy, difluoromethoxy, 1,1,2,2-tetrafluoroethoxy, 1,1,2,3,3,3-hexafluoropropoxy, 2-chloro-1,1,2-trifluoroethoxy, bromodifluoromethoxy, 2-bromo-1,1,2,2-tetrafluoroethoxy, 2-methoxyethoxy, methoxycarbonyl, ethoxycarbonyl or nitro.

4. The compound of claim 2 wherein $B^3$ is a hydrogen atom, chloro, fluoro, bromo, trifluoromethyl, trifluoromethoxy, difluoromethoxy or 1,1,2,2-tetrafluoroethoxy.

5. The compound of claim 2 wherein $B^4$ is chloro, bromo, trifluoromethyl, trifluoromethoxy, difluoromethoxy, 1,1,2,2-tetrafluoroethoxy, 1,1,2,3,3,3-hexafluoropropoxy, 2-chloro-1,1,2-trifluoroethoxy, bromodifluoromethoxy, or 2-bromo-1,1,2,2-tetrafluoroethoxy.

6. The compound of claim 2 wherein V is a hydrogen atom, methyl, methylcarbonyl, methoxycarbonyl or formyl.

7. The compound of claim 2 wherein $Y^1$ is a hydrogen atom, methyl, ethyl, n-propyl, isopropyl, n-butyl, allyl or propargyl.

8. The compound of claim 2 wherein $Y^2$ is a hydrogen atom, methoxycarbonyl, ethoxycarbonyl, n-propoxycarbonyl, isopropoxycarbonyl, tert-butoxycarbonyl, benzyloxycarbonyl, phenoxycarbonyl, chloromethoxycarbonyl, bromomethoxycarbonyl, 2-chloroethoxycarbonyl, 2-bromoethoxycarbonyl, 3-chloro-1-propoxycarbonyl, 3-bromo-1-propoxycarbonyl, 2,2,2-trifluoroethoxycarbonyl, 2-methoxyethoxycarbonyl, allyloxycarbonyl, propargyloxycarbonyl, formyl, methylcarbonyl, ethylcarbonyl, isopropylcarbonyl, tert-butylcarbonyl, trifluoromethylcarbonyl, benzoyl, vinylcarbonyl, isopropenylcarbonyl, methylcarbonylcarbonyl, methylthiocarbonyl, ethylthiocarbonyl, methylsulfonyl, ethylsulfonyl, phenylsulfonyl, methylaminocarbonyl, dimethylaminocarbonyl, diethylphosphoryl or diethylthiophosphoryl.

9. The compound of claim 3 wherein $A^3$ is a hydrogen atom, chloro, methoxy, difluoromethoxy, n-propoxy, methyl or n-propyl.

10. The compound of claim 3 wherein $A^4$ is chloro, trifluoromethyl, difluoromethoxy, n-propoxy or n-propyl.

11. The compound of claim 4 wherein $B^3$ is a hydrogen atom or chloro.

12. The compound of claim 5 wherein $B^4$ is trifluoromethyl, trifluoromethoxy or 1,1,2,2-tetrafluoroethoxy.

13. The compound of claim 6 wherein V is a hydrogen atom.

14. The compound of claim 7 wherein $Y^1$ is a hydrogen atom, methyl or n-propyl.

15. The compound of claim 8 wherein $Y^2$ is a hydrogen atom, methoxycarbonyl, formyl or methylcarbonyl.

16. The compound of claim 2 wherein $A^3$ and $A^4$ are each independently a hydrogen atom, methyl, ethyl, n-propyl, n-butyl, fluoro, chloro, bromo, trifluoromethyl, methoxy, ethoxy, n-propoxy, n-butoxy, trifluoromethoxy, difluoromethoxy, 1,1,2,2-tetrafluoroethoxy, 1,1,2,3,3,3-hexafluoropropoxy, 2-chloro-1,1,2-trifluoroethoxy, bromodifluoromethoxy, 2-bromo-1,1,2,2-tetrafluoroethoxy, 2-methoxyethoxy, methoxycarbonyl, ethoxycarbonyl or nitro;

$B^3$ is a hydrogen atom, chloro, fluoro, bromo, trifluoromethyl, trifluoromethoxy, difluoromethoxy or 1,1,2,2-tetrafluoroethoxy;

$B^4$ is chloro, bromo, trifluoromethyl, trifluoromethoxy, difluoromethoxy, 1,1,2,2-tetrafluoroethoxy, 1,1,2,3,3,3-hexafluoropropoxy, 2-chloro-1,1,2-trifluoroethoxy, bromodifluoromethoxy or 2-bromo-1,1,2,2-tetrafluoroethoxy;

V is a hydrogen atom, methyl, methylcarbonyl, methoxycarbonyl or formyl;

$Y^1$ is a hydrogen atom, methyl, ethyl, n-propyl, isopropyl, n-butyl, allyl or propargyl; and $Y^2$ is a hydrogen atom, methoxycarbonyl, ethoxycarbonyl, n-propoxycarbonyl, isopropoxycarbonyl, tert-butoxycarbonyl, benzyloxycarbonyl, phenoxycarbonyl, chloromethoxycarbonyl, bromomethoxycarbonyl, 2-chloroethoxycarbonyl, 2-bromoethoxycarbonyl, 3-chloro-1-propoxycarbonyl, 3-bromo-1-propoxycarbonyl, 2,2,2-trifluoroethoxycarbonyl, 2-methoxyethoxycarbonyl, allyloxycarbonyl, propargyloxycarbonyl, formyl, methylcarbonyl, ethylcarbonyl, isopropylcarbonyl, tert-butylcarbonyl, trifluoromethylcarbonyl, benzoyl, vinylcarbonyl, isopropenylcarbonyl, methylcarbonylcarbonyl, methylthiocarbonyl, ethylthiocarbonyl, methylsulfonyl, ethylsulfonyl, phenylsulfonyl, methylaminocarbonyl, dimethylaminocarbonyl, diethylphosphoryl or diethylthiophosphoryl.

17. The compound of claim 16 wherein $A^3$ is a hydrogen atom, chloro, methoxy, difluoromethoxy, ethoxy, n-propoxy, methyl or n-propyl;

$A^4$ is chloro, trifluoromethyl, difluoromethoxy, n-propoxy or n-propyl;

$B^3$ is a hydrogen atom or chloro;

$B^4$ is trifluoromethyl, trifluoromethoxy or 1,1,2,2-tetrafluoroethoxy;

V is a hydrogen atom;

$Y^1$ is a hydrogen atom, methyl or n-propyl; and $Y^2$ is a hydrogen atom, methoxycarbonyl, formyl or methylcarbonyl.

18. An insecticidal composition which comprises an agriculturally acceptable carrier and an insecticidally effective amount of the compound of claim 1.

19. An insecticidal composition which comprises an agriculturally acceptable carrier and an insecticidally effective amount of the compound of claim 2.

20. A method of controlling insects which comprises contacting the insects with an insecticidally effective amount of the compound of claim 1.

21. A method of controlling insects which comprises contacting the insects with an insecticidally effective amount of the compound of claim 2.

22. The method of claims 20 or 21 wherein the compound is applied at a rate of from about 0.10 g to about 1000 g per hectare.

* * * * *